United States Patent
Garti et al.

(10) Patent No.: US 10,149,824 B2
(45) Date of Patent: Dec. 11, 2018

(54) REVERSE HEXAGONAL MESOPHASES ($H_{II}$) AND USES THEREOF

(75) Inventors: Nissim Garti, Ramat Ha Sharon (IL); Abraham Aserin, Jerusalem (IL); Dima Libster, Jerusalem (IL); Idit Amar-Yuli, Jerusalem (IL); Tehila Mishraki, Jerusalem (IL); Liron Bitan-Chervkovsky, Shoham (IL)

(73) Assignee: YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 1049 days.

(21) Appl. No.: 13/379,769

(22) PCT Filed: Jun. 24, 2010

(86) PCT No.: PCT/IL2010/000507
§ 371 (c)(1),
(2), (4) Date: Aug. 17, 2012

(87) PCT Pub. No.: WO2010/150262
PCT Pub. Date: Dec. 29, 2010

(65) Prior Publication Data
US 2013/0034538 A1 Feb. 7, 2013

Related U.S. Application Data

(60) Provisional application No. 61/220,398, filed on Jun. 25, 2009, provisional application No. 61/302,649, filed on Feb. 9, 2010.

(51) Int. Cl.
*A61K 9/127* (2006.01)
*A61K 9/00* (2006.01)
(Continued)

(52) U.S. Cl.
CPC .......... *A61K 9/1274* (2013.01); *A61K 9/0014* (2013.01); *A61K 9/0053* (2013.01);
(Continued)

(58) Field of Classification Search
CPC .................................................... A61K 9/1274
See application file for complete search history.

(56) References Cited

U.S. PATENT DOCUMENTS

| | | | | | |
|---|---|---|---|---|---|
| 5,143,934 A | * | 9/1992 | Lading | ................. | A61K 9/0063 424/423 |
| 2005/0077497 A1 | * | 4/2005 | Anderson | ............ | A61K 9/1274 252/299.1 |

(Continued)

FOREIGN PATENT DOCUMENTS

| WO | 9713528 A1 | 4/1997 |
|---|---|---|
| WO | 9810747 A1 | 3/1998 |

(Continued)

OTHER PUBLICATIONS

Libster et al. (2007). An Hii liquid crystal-based delivery system for cyclosporin A: Physical characterization. Journal of Colloid and Interface Science, 308: 514-524.*

(Continued)

*Primary Examiner* — Isaac Shomer
(74) *Attorney, Agent, or Firm* — Browy and Neimark, PLLC

(57) ABSTRACT

Reverse hexagonal mesophase ($H_{II}$) liquid crystals provide multi-component hexagonal systems for use in solubilizing and/or protecting from degradation one or more bio-macromolecule and/or active material, and relates to therapeutic and non-therapeutic applications, such as an oral delivery system, where the mesophase is adapted for oral administration. The present invention provides the formation of mesophase systems of ternary glycerol monooleate (GMO)/

(Continued)

Lattice parameter water combinations which comprise at least one triglyceride or an equivalent thereof. At least one biomacromolecule or drug is incorporated in the mesophase of a pharmaceutical composition or oral delivery system.

17 Claims, 53 Drawing Sheets

(51) Int. Cl.
    *A61K 38/13*      (2006.01)
    *A61K 38/28*      (2006.01)
    *A61K 38/31*      (2006.01)

(52) U.S. Cl.
    CPC .............. *A61K 38/13* (2013.01); *A61K 38/28* (2013.01); *A61K 38/31* (2013.01)

(56) References Cited

U.S. PATENT DOCUMENTS

| 2007/0176143 | A1* | 8/2007 | Garti | ................... | B01F 17/0064 |
| | | | | | 252/299.01 |
| 2008/0161276 | A1* | 7/2008 | Johnsson | ............. | A61K 9/1274 |
| | | | | | 514/178 |

FOREIGN PATENT DOCUMENTS

| WO | 9847487 A1 | 10/1998 | | |
| WO | WO 9847487 A1 * | 10/1998 | ........... | A61K 9/1274 |
| WO | 0009117 A1 | 2/2000 | | |
| WO | 2005046642 A1 | 5/2005 | | |
| WO | WO 2007139854 A2 * | 12/2007 | ............... | A61K 9/06 |

OTHER PUBLICATIONS

Wallin et al. (1993). "The Activity of Lipase at the Cubiv Liquid-Crystalline Phase/Water Interface". Journal of Colloid and Interface Science, 164: 16-20.*
Amar-Yuli, I. and Garti, N. (2005). "Transitions induced by solubilized fat into reverse hexagonal mesophases." Colloids and Surfaces B: Biointerfaces, 43: 72-82.*
T Kamo, M Nakano, W Leesajakul, A Sugita, H Matsuoka, T Handa. "Nonlamellar Liquid Crystalline Phases and Their Particle Formation in the Egg Yolk Phosphatidylcholine/Diolein System." Langmuir, vol. 19, 2003, pp. 9191-9195.*
I Amar-Yuli, N Garti. "Transitions induced by solubilized fat into reverse hexagonal mesophases." Colloids and Surfaces B: Biointerfaces, vol. 43, 2005, pp. 72-82. (Year: 2005).*
D Libster, A Aserin, N Garti. "Interactions of biomacromolecules with reverse hexagonal liquid crystals: Drug delivery and crystallization applications." Journal of Colloid and Interface Science, vol. 356, 2011, pp. 375-386. (Year: 2011).*
I-H Kim, C-S Yoon, S-H Cho, K-W Lee, S-H Chung, B-S Tae. "Lipase-Catalyzed Incorporation of Conjugated Linoleic Acid into Tricaprylin." Journal of the American Oil Chemists Society, vol. 78 No. 5, 2001, pp. 547-551. (Year: 2001).*
Idit Amar-Yuli, Ellen Wachtel, Einav Ben Shoshan, Dganit Danino, Abraham Aserin, and Nissim Garti, Hexosome and Hexagonal Phases Mediated by Hydration and Polymeric Stabilizer, Langmuir, 2007, pp. 3637-3645 vol. 23, No. 7, American Chemical Society, United States.
Dima Libster, Paul Ben Ishai, Abraham Aserin, Gil Shoham, and Nissim Garti, From the Microscopic to the Mesoscopic Properties of Lyotropic Reverse Hexagonal Liquid Crystals, Langmuir, 2008, pp. 2118-2127, vol. 24, No. 5, American Chemical Society, United States.
Idit Amar-Yuli, Nissim Garti, Transitions induced by solubilized fat into reverse hexagonal mesophases, Colloids and Surfaces B: Biointerfaces, 2005, pp. 72-82, vol. 43, Elsevier B.V.
Dima Libster, Abraham Aserin, Ellen Wachtel, Gil Shoham, Nissim Garti, An HII liquid crystal-based delivery system for cyclosporin A: Physical characterization, Journal of Colloid and Interface Science, 2007, pp. 514-524, vol. 308, Elsevier B.V.
Bodil Ericsson, Kare Larsson, Krister Fontell, A cubic protein-monoolein-water phase, Biochimica et Biophysica Acta, 1983, pp. 23-27, vol. 729, Elsevier Biomedical Press.
Idit Amar-Yuli, Ellen Wachtel, Deborah E. Shalev, Abraham Aserin, and Nissim Garti, Low Viscosity Reversed Hexagonal Mesophases Induced by Hydrophilic Additives, J. Phys. Chem. B 2008, pp. 3971-3982, vol. 112, American Chemical Society, United States.
M.G. Carr, J. Corish, O.I. Corrigan, Drug delivery from a liquid crystalline base across Visking and human stratum corneum, International Journal of Pharmaceutics, 1997, pp. 35-42, vol. 157, Elsevier Science B.V.
Jaehwi Lee, Ian W. Kellaway, Buccal permeation of [D-Ala2, D-Leu5] enkephalin from liquid crystalline phases of glyceryl monooleate, International Journal of Pharmaceutics, 2000, pp. 35-38, vol. 195, Elsevier Science B.V.
Jaehwi Lee, Ian W. Kellaway, Combined effect of oleic acid and polyethylene glycol 200 on buccal permeation of [D-Ala2, D-Leu5]enkephalin from a cubic phase of glyceryl monooleate, International Journal of Pharmaceutics, 2000, pp. 137-144, vol. 204, Elsevier Science B.V.
Idit Amar-Yuli, Abraham Aserin, and Nissim Garti, Solubilization of Nutraceuticals into Reverse Hexagonal Mesophases, J. Phys. Chem. B 2008, pp. 10171-10180, vol. 112, American Chemical Society, United States.
Calum J. Drummond and Celesta Fong, Surfactant self-assembly objects as novel drug delivery vehicles, Current Opinion in Colloid & Interface Science, 2000, pp. 449-456, vol. 4, Elsevier Science B.V.
J. Clogston and M. Caffrey, Controlling release from the lipidic cubic phase. Amino acids, peptides, proteins and nucleic acids, Journal of Controlled Release, 2005, pp. 97-111, vol. 107, Elsevier Science B.V.
Manish H. Shah, Anant Paradkar, Cubic liquid crystalline glyceryl monooleate matrices for oral delivery of enzyme, International Journal of Pharmaceutics, 2005, pp. 161-171, vol. 294, Elsevier Science B.V.
B. Ericsson, P. O. Eriksson, J. E. Löfroth, S. Engström, Cubic Phases as Delivery Systems for Peptide Drugs, 1991, pp. 251-265, Washington D.C., United States.
J. Kraineva, V. Smirnovas, R. Winter, Effects of Lipid Confinement on Insulin Stability and Amyloid Formation, Langmuir, 2007, pp. 7118-7126 vol. 23, American Chemical Society, United States.
F. Liu, R. N. A. H. Lewis, R. S. Hodges, R. N. McElhaney, A Differential Scanning Calorimetric and 31P NMR Spectroscopic Study of the Effect of Transmembrane R-Helical Peptides on the Lamellar-Reversed Hexagonal Phase Transition of Phosphatidylethanolamine Model Membranes, Biochemistry, 2001, pp. 760-768, vol. 40, American Chemical Society, United States.
W. Liu, M. J. Caffrey, Gramicidin structure and disposition in highly curved membranes, Journal of Structural Biology, 2005, pp. 23-40, vol. 150, Elsevier Inc.
L. B. Lopes, J. L. C. Lopes, D. C. R. Oliveira, J. A. Thomazini, M. T. J. Garcia, M. C. A. Fantini, J. H. Collett, M. V. L. B. Bentely,Liquid crystalline phases of monoolein and water for topical delivery of cyclosporin A: Characterization and study of in vitro and in vivo delivery, European Journal Pharmaceutics and Biopharmaceutics, 2006, pp. 146-155, vol. 63, Elsevier Science B.V.
D. Libster, P. Ben Ishai, A. Aserin, G. Shoham, N. Garti, Molecular interactions in reverse hexagonal mesophase in the presence of Cyclosporin A, International Journal of Pharmaceutics, 2009, pp. 115-126, vol. 367, Elsevier Science B.V.
D. Libster, A. Aserin, D. Yariv, G. Shoham, N. Garti, Concentration- and Temperature-Induced Effects of Incorporated Desmopressin on the Properties of Reverse Hexagonal Mesophase, J. Phys. Chem. B., 2009, pp. 6336-6346, vol. 113, American Chemical Society, United States.
P. Ben Ishai, D. Libster, A. Aserin, N. Garti, Y. Feldman, Molecular Interactions in Lyotropic Reverse Hexagonal Liquid Crystals: A

(56) References Cited

OTHER PUBLICATIONS

Dielectric Spectroscopy Study, J. Phys. Chem. B., 2009, pp. 12639-12647, vol. 113, American Chemical Society, United States.

V. Razumas, Z. Talaikyte, J. Barauskas, K. Larsson, Y. Miezis and T. Nylander, Effects of distearoylphosphatidylglycerol and lysozyme on the structure of the monoolein-water cubic phase: X-ray diffraction and Raman scattering studies, Chemistry and Physics of Lipids, 1996, pp. 123-138, vol. 84, Elsevier Science Ireland Ltd.

Dima Libster, Soft matter dispersions with ordered inner structures, stabilized by ethoxylated phytosterols, Colloids and Surfaces B: Biointerfaces, 2009, pp. 1-14, Elsevier Science B.V.

Amar-Yuli, Thermally Induced Fluid Reversed Hexagonal (HII) Mesophase, J. Phys. Chem. B 2007, pp. 13544-13553, vol. 111, American Chemical Society, United States.

Amar-Yuli, Solubilization of food bioactives within lyotropic liquid crystalline mesophases, Current Opinion in Colloid & Interface Science, 2009, pp. 21-32, vol. 14, Elsevier Ltd.

Johanna Born, Tommy Nylander, Ali Khan, Effect of Lipase on Different Lipid Liquid Crystalline Phases Formed by Oleic Acid Based Acylglycerols in Aqueous Systems, Langmuir, 2002, pp. 8972-8981, vol. 18, No. 23, American Chemical Society, United States.

Johanna Born, Tommy Nylander, Ali Khan, Effect of Lipase on Monoolein-Based Cubic Phase Dispersion (Cubosomes) and Vesicles, J. Phys. Chem. B, 2002, pp. 10492-10500, vol. 106, No. 40, American Chemical Society, United States.

Caboi, Lipase action on a monoolein/sodium oleate aqueous cubic liquid crystalline phase—a NMR and X-ray diffraction study, Colloids and Surfaces B: Biointerfaces, 2002, pp. 159-171, vol. 26, Elsevier Science B.V.

Wallin, The Activity of Lipase at the Cubic Liquid-Crystalline Phase/Water Interface, Journal of Colloid and Interface Science, 1994, pp. 16-20, vol. 164, Academic Press, Inc.

Chopineau, Self-evolving microstructured systems upon enzymatic catalysis, Biochimie 1998, pp. 421-435, vol. 80, Elsevier, Paris France.

Misinuas, Thermomyces lanuginosus lipase in the liquid-crystalline phases of aqueous phytantriol: X-ray diffraction and vibrational spectroscopic studies, Biophysical Chemistry, 2008, pp. 144-156, vol. 134, Elsevier Science B.V.

Interanational Search Report: Application No. PCT/IL2010/000507, dated 2011, Rijswijk, the Netherlands.

* cited by examiner

REVERSE HEXAGONAL MESOPHASES ($H_{II}$) AND USES THEREOF

FIELD OF THE INVENTION

The present invention relates to reverse hexagonal mesophase ($H_{II}$) liquid crystals and relating applications.

BACKGROUND OF THE INVENTION

Liquid crystalline mesophases based on glycerol monooleate (GMO, also known as monoolein, monoglyceride) are the subject of an ongoing scientific research due to their complex structural features and various potential applications. These systems are characterized by a high internal ordering and symmetry as well as by a vast interfacial area and the existence of both hydrophobic and hydrophilic domains. These structural properties make lyotropic liquid crystals (LLC) promising candidates for research and applications in drug delivery, food systems and the synthesis of template-ordered materials. The common and well-studied LLC phases are the lamellar ($L_\alpha$), hexagonal (normal, $H_I$ or inverted $H_{II}$) and normal or inverted cubic (bicontinuous or micellar) structures.

Significant progress has been made during the last decade in the characterization of interactions of proteins with cubic LLC, mainly for crystallographic and drug delivery purposes. Cubic phase was successfully used for entrapment and crystallization of several membrane proteins for single crystal X-ray crystallography goals. Hydrophilic proteins such as lysozyme, cytochrome C, hemoglobin and insulin were solubilized into the cubic phase.

While the mutual interplay of the cubic phase components, including the phase behavior and the structural conformations of the proteins, was demonstrated and discussed, the understanding of the interactions of proteins with reverse hexagonal mesophases ($H_{II}$) that are involved in different biological processes like membrane fusion, and might be found in cellular and intracellular membranes is lacking.

$H_{II}$ mesophases consist of cylindrical surfactant micelles arranged on a two-dimensional hexagonal lattice. These structures can accommodate hydrophilic, hydrophobic and amphiphilic guest molecules either within the aqueous compartments, composed of dense packed, straight water-filled cylinders, or by direct interaction within the lipid hydrophobic moieties, orientated radially outward from the centers of the water rods [1, 2]. Furthermore, lower viscosity of these mesophases, compared to the highly viscous cubic phase, is advantageous for practical applications.

While the $H_{II}$ mesophase based only on monoolein and water existed in elevated temperatures (the cubic phase is transformed into the $H_{II}$ mesophase only at ca. 85° C.) and hence could not have been used for solubilization of peptides and proteins, recently the ability of triacylglycerols (triglycerides, TAG) to promote existence of $H_{II}$ phases at room temperature was investigated. It was found that TAGs with medium-chain fatty acids transformed lamellar and cubic phases into a hexagonal mesophase that remains stable at room temperature [3]. This finding enabled the solubilization of biomacromolecules into the mesophase and their utilization as drug delivery vehicles and also as matrices for chemical and enzymatic reactions.

Physical properties of ternary GMO/tricaprylin/water $H_{II}$ mesophases were extensively studied. Furthermore, it was demonstrated that lipophilic peptide drug cyclosporine A and hydrophilic desmopressin were solubilized into the $H_{II}$ mesophases [4]. The effect of their incorporation on the mesophases, as well as the structural conformations of the peptides were studied both on a macroscopic and molecular levels.

REFERENCES

[1] I. Amar-Yuli, E. Wachtel, E. Ben Shoshan, D. Damino, A. Aserin and N. Garti, Langmuir 23 (2007) 3637-3645.
[2] D. Libster, P. Ben Ishai, A. Aserin, G. Shoham and N. Garti, Langmuir 24 (2008) 2118-2127.
[3] I. Amar-Yuli and N. Garti, Colloid Surf. B 43 (2005) 72-82.
[4] D. Libster, A. Aserin, E. Wachtel, G. Shoam and N. Garti, J. Colloid Interface Sci. 308 (2007) 514-524.
[5] B. Ericsson, K. Larsson and K. Fontell, Biochim. Biophys. Acta 729 (1983) 23-27, V. Razumas, Z. Talalkyle, J. Barauskas, K. Larsson, Y. Miezis and T. Nylander, Chem. and Phys. Lipids 84 (1996) 123-138.
[6] D. Libster, A. Aserin, E. Wachtel, G. Shoam and N. Garti, J. Colloid Interface Sci. 308 (2007) 514-524; I. Amar-Yuli, E. Wachtel, D. E. Shalev, A. Aserin and N. Garti, J. Phys. Chem. B 112 (2008) 3971-3982.
[7] M. G. Carr, J. Corish, O. I. Corrigan, Int. J. Pharm. 157 (1997) 35-42.
[8] J. Lee, I. W. Kellaway, Int. J. Pharm. 195 (2000) 35-8.
[9] J. Lee, I. W. Kellaway, Int J. Pharm. 204 (2000) 137-44.
[10] I. Amar-Yuli, A. Aserin, N. Garti, J. Phys. Chem. B 112 (2008) 10171-80.
[11] C. J. Drummond, C. Fong, Curr. Opin. Colloid Interface Sci. 4 (2000) 449-456.
[12] J. Clogston, M. J. Caffrey, Controlled Release 107 (2005) 97-111.
[13] M. H. Shah, A. Paradkar, Int. J. Pharm. 294 (2005) 161-171.
[14] B. Ericsson, P. O. Eriksson, J. E. Ldfroth, S. Engström, Am. Chem. Soc. Washington, D.C. (1991) 251-265.
[15] J. Kraineva, V. Smirnovas, R. Winter, Langmuir 23 (2007) 7118-7126.
[16] F. Liu, R. N. A. H. Lewis, R. S. Hodges, R. N. McElhaney, Biochemistry 40 (2001) 760-768.
[17] W. Liu, M. J. Caffrey, Structural Biol. 150 (2005) 23-40.
[18] L. B. Lopes, J. L. C. Lopes, D. C. R. Oliveira, J. A. Thomazini, M. T. J. Garcia, M. C. A. Fantini, J. H. Collett, M. V. L. B. Bentely, Eur. J. Pharm. Biopharm. 63 (2006) 146-155.
[19] D. Libster, A. Aserin, E. Wachtel, G. Shoham, N. J. Garti, Colloid. Interface Sci. 308 (2007) 514-524.
[20] D. Libster, P. Ben Ishai, A. Aserin, G. Shoham, N. Garti, Int. J. Pharm. 367 (2009) 367, 115-126.
[21] D. Libster, A. Aserin, D. Yariv, G. Shoham, N. Garti, J. Phys. Chem. B. 113 (2009) 6336-6346.
[22] P. Ben Ishai, D. Libster, A. Aserin, N. Garti, Y. Feldman, J. Phys. Chem. B. 113 (2009) 12639-12647.

SUMMARY OF THE INVENTION

It is the aim of the present application to provide multi-component hexagonal systems for use in solubilizing and/or protecting from degradation one or more bio-macromolecule and/or active material. Specifically, the invention provides the formation of mesophase systems of ternary GMO/water combinations which comprise at least one triglyceride (herein referred to as TAG) or an equivalent thereof.

In one aspect of the invention, there is provided a mesophase comprising at least one amphipathic molecule, at least one lipophilic compound and water, wherein said mesophase is adapted for oral administration.

In another aspect there is provided a pharmaceutical composition for oral delivery of at least one biomacromolecule, comprising a mesophase of at least one amphipathic molecule, at least one lipophilic compound and water, said at least one biomacromolecule being incorporated in said mesophase.

An oral delivery system is also provided for the delivery of at least one biomacromolecule, said system comprising a mesophase of at least one amphipathic molecule, at least one lipophilic compound and water, said at least one biomacromolecule being incorporated in said mesophase.

The oral delivery system may also be one wherein the mesophase is adapted to release the drug gradually over a period of time after administration.

In a further aspect there is provided an oral drug delivery system for the delivery of a drug, said system comprising a drug and an amphipathic/lipophilic/water mesophase or an extended form thereof, wherein said drug is contained within said mesophase, the mesophase being adapted to deliver the drug at a rate and/or concentration greater than the rate and/or concentration of the drug when contained in a system lacking or absenting said mesophase.

In yet another aspect, a delivery system is provided for the delivery of a drug, said system comprising a drug, a mesophase comprising at least one amphipathic molecule, at least one lipophilic compound and water, and an hydrolyzing agent, said drug being contained within said mesophase, the hydrolyzing agent being capable of (or being adapted to) causing degradation of said mesophase, thereby releasing the drug gradually over a period of time after administration.

Additionally, a mesophase is provided which comprises at least one amphipathic molecule, at least one lipophilic compound and water, wherein said at least one lipophilic compound is selected to minimize or prevent degradation of at least one solubilized material which is intercalated within said mesophase.

Also provided, within the scope of the present invention, is the use of a mesophase, as herein defined for solubilizing at least one material selected amongst hydrophobic and hydrophilic materials.

A method is also provided for protecting at least one compound from decomposition, said method comprising solubilizing said at least one compound in a mesophase as disclosed herein.

Also provided is a method for transport (cellular microinjection) of at least one material across a cell membrane, in vitro or in vivo, the method comprising solubilizing said at least one material in a mesophase, as disclosed, to obtain a mesophase/solute system, contacting said cell membrane with an amount of said system under conditions allowing transport of said material through the cell membrane.

GENERAL DESCRIPTION OF THE INVENTION

The multi-component reverse $H_{II}$ mesophase of cylindrical micelles is arranged on a 2-dimensional hexagonal lattice, as depicted in FIG. 1, with each cylindrical micelle being formed of at least one mono fatty acid ester, at least one lipophilic compound being selected to interact with said at least one mono fatty acid ester, and water, wherein said mesophase being capable of solubilizing at least one hydrophilic and/or hydrophobic material, e.g., within the densely-packed, straight water-filled cylindrical compartments and/or on their surface within the lipid hydrophobic moieties, orientated radially outward from the centers of the water cylinders.

It is the purpose of the present invention to provide numerous unexpected modifications of the reverse (inverted) hexagonal $H_{II}$ mesophase of the art which are particularly suitable and effectitious as reservoir vehicles for solubilization of molecules of various molecular weights, including biomolecules, biomacromolecules, bioactives and others as further disclosed hereinbelow. The system of the invention not only allows for solubilization of such molecules but also provides mechanism by which such molecules, being at times susceptible to oxidation/reduction and other degradations, maintain their stability and thus their activity.

For purposes of clarity and brevity, the mesophases of the invention will be related to by the following designation: amphipathic/lipophilic/water, wherein "amphipatic" is an amphipatic molecule having the tendency to form a hexagonal phase, e.g., a mono fatty acid ester derived from an acid addition of a long chain acid; the "lipophilic" is a compound selected to interact with said amphipatic molecule, forming together with water a ternary system. The ternary system may be extended to other multi-component systems having similarly 4, 5, 6 and further components, thus forming an extended system In one aspect of the present invention, there is provided a mesophase, as defined herein, wherein the at least one lipophilic compound is at least one antioxidant capable of minimizing or preventing degradation, e.g., through any degrading mechanism including oxidation, of at least one solubilized material which is intercalated, housed, contained or solubilized within the cylindrical cavities or on their surface. Thus, the invention provides a ternary or extended ternary amphipathic/lipophilic/water mesophase being in the general form amphipathic/antioxidant/water (where the antioxidant replaces said at least one lipophilic compound) or amphipathic/lipophilic/antioxidant/water (where the antioxidant is introduced in addition to the lipophilic compound).

In some embodiments, the at least one amphipathic molecule is an organic or inorganic mono fatty acid ester derived from unsaturated fatty acids having between 10 and 24 carbon atoms and at least one carbon-carbon double bond. In some embodiments, the ester is derived from an acid having 16 or 18 carbon atoms and at least one carbon-carbon double bond.

Non-limiting examples of such acids are myristoleic acid (14:1), palmitoleic acid (16:1), oleic acid (18:1), cis-vaccenic acid (18:1), elaidic acid (18:1), linoleic acid (18:2), alpha-linolenic acid (18:3), gamma-linolenic acid (18:3), stearidonic acid (18:4), dihomo-gamma-linolenic acid (20:3), archidonic acid (20:4), eicosapentaenoic acid (20:5), erucic acid (22:1), erucic acid (22:1), docosahexaenoic acid (22:6), and nervonic acid (24:1).

In some embodiments, the at least one mono fatty acid ester is derived from an unsaturated fatty acid selected from palmitoleic acid (16:1), oleic acid (18:1), cis-vaccenic acid (18:1), elaidic acid (18:1), linoleic acid (18:2), alpha-linolenic acid (18:3), gamma-linolenic acid (18:3), and stearidonic acid (18:4).

In some further embodiments, the at least one mono fatty acid ester is selected amongst glycerol esters and phospholipids of one or more unsaturated acids as defined above.

The glycerol esters may be selected from: a monoglyceride of one unsaturated fatty acid, being connected at the C-1 or C-2 position of the glycerol; a diglyceride of at least one unsaturated fatty acid, being connected at the C-1 and C-2 or C-1 and C-3 positions of the glycerol; and a triglyceride of at least one unsaturated fatty acid.

The diglyceride ester may be composed of two identical unsaturated fatty acids or two different unsaturated fatty acids. The diglyceride ester may alternatively be composed of one unsaturated fatty acid and one acid selected from saturated fatty acid or short chain saturated or unsaturated acid. Similarly, the triglyceride ester may be composed of three identical unsaturated fatty acids, three different unsaturated fatty acids or any combination with a saturated or short chain unsaturated acid, provided that at least one of the esters is of an unsaturated fatty acid having between 10 and 24 carbon atoms.

Where the ester is composed of one or more saturated fatty or short chain linear acids, the saturated acid may be selected from butyric acid (butanoic acid, 4:0), valeric acid (pentanoic acid, 5:0), caproic acid (hexanoic acid, 6:0), caprylic acid (octanoic acid, 8:0), capric acid (decanoic acid, 10:0), lauric acid (dodecanoic acid, 12:0), myristic acid (tetradecanoic acid, 14:0), palmitic acid (hexadecanoic acid, 16:0), stearic acid (octadecanoic acid, 18:0), arachidic acid (eicosanoic acid, 20:0), behenic acid (docosanoic acid, 22:0), and lignoceric acid (tetracosanoic acid, 24:0).

Where the ester is composed of one or more short chain saturated or unsaturated, linear or branched acid, the acid may be selected from acetic acid, propionic acid, butyric acid, pentanoic acid, hexanoic acid, citric acid, lactic acid, tartaric acid, acrylic acid, salicylic acid, adipic acid, glutaric acid, aconitic acid, glycolic acid, and one or more amino acids as known in the art.

The phospholipids are glycerophospholipids being selected from mono-phosphatidyl glycerols, bis-phosphatidyl glycerols, and tris-phosphatidyl glycerols. Non-limiting examples of such phospholipids are phosphatidyl choline (PC), dipalmitoylphosphatidylcholine, phosphatidyl ethanolamine (cephalin), phosphatidyl inositol, phosphatidyl serine, cardiolipin, plasmalogen, lysophosphatidic acid, phosphatidylinositol (3,4)-bisphosphate, phosphatidylinositol (3,5)-bisphosphate, phosphatidylinositol (4,5)-bisphosphate, phosphatidylinositol 4-phosphate, phosphatidylinositol (3,4,5)-trisphosphate, and phosphatidylinositol 3-phosphate.

In some embodiments, the at least one mono fatty acid ester is a mixture of two or more such esters.

The at least one mono fatty acid ester mixture employed in the hexagonal mesophase of the invention may be one or more of a variety of mixtures. In some embodiments, the mixture is of monoglycerides, diglycerides and/or triglycerides of unsaturated fatty acids. The following are some non-limiting mixtures:

1. a mixture of monoglycerides of the same acid and diglycerides and/or triglycerides of a different acid;
2. a mixture of monoglycerides and diglycerides and/or triglycerides, all of the same acid;
3. a mixture of monoglycerides of different acids and diglycerides of the same acids;
4. a mixture of monoglycerides or diglycerides with triglycerides of the same or different acid; and
5. a mixture of diglycerides wherein one ester is of an unsaturated fatty acid and the other may be derived from an unsaturated fatty acid and/or a saturated acid.

In some further embodiments, the glycerol ester is employed in a mixture with glycerol. In further embodiments, the mixture comprises at least one glycerol ester and at least one ester derived from a mono-ol, a di-ol and/or a tri-ol being different from glycerol.

In yet further embodiments, the mixture comprises at least one phospholipid and at least one glycerol ester.

In some embodiments, the mixture as exemplified comprises at least 92% of a monoglyceride derived from an unsaturated fatty acid having between 10 and 24 carbon atoms and at least one carbon-carbon double bond.

In some embodiments, the at least one glyceride is glycerol monooleate (GMO) or mixtures comprising thereof. In other embodiments, the at least one glyceride is a glycerophospholipid.

The at least one lipophilic compound employed may be itself at least one antioxidant or be present in the mesophase in addition to said at least one antioxidant. Generally speaking, the lipophilic compound (or antioxidant) is first selected to interact, typically via Van der Waals interactions, with the hydrophobic residue of the mono fatty acid esters, e.g., the glycerol mono esters, to thereby impose at least one structural modification on the hexagonal mesophase. The structural modification may involve modulation (increase or decrease) of one or more parameters such as the size of the spacing between the hydrophobic residues of the mono fatty acid esters, the lattice parameter, the radius and/or length of the cylindrical micelle and others. Such modifications enable efficient intercalation of the protein or any other biomacromolecule (bioactive) within the cylindrical compartments and/or on their surface, even where such intercalation is structurally unexpected, as further demonstrated.

The lipophilic component may, thus, be selected to provide, maintain, enhance or diminish one or more structural property of the mesophase, such property may be selected amongst properties of the system such as the thermal stability of the mesophase and its cell-membrane fusion abilities, the stability of a chemical entrapped within the cylindrical cavity or intercalated on its outer surface and maintain activity of labile chemicals solubilized in the mesophase.

The lipophilic compounds may be selected from a triacylglycerol (TAGs), vitamin E (VE, alpha-tocopherol) and a phosphatidyl ester (as above). In some embodiments, the at least one lipophilic compound is at least one TAG derived from a fatty acid having between 2 and 18 carbon atoms. Non-limiting examples include triacetin, tributyrin, tricaprylin, trilaurin, trimyristin and tristearin.

The lipophilic antioxidant, which may be present in the mesophase in place of the lipophilic compound, as defined, or in addition thereto, may be selected from vitamin E (alpha-tocopherol); cholesterol; phytosterol; lycopen; beta-carotene; carnosic acid; beta-tocopherol; gamma-tocopherol; delta-tocopherol; epsilon-tocopherol, zeta 1-tocopherol; zeta 2-tocopherol; eta-tocopherol and 1-ascorbic acid 6-palmitate.

In some embodiments, the antioxidant is vitamin E and the extended ternary mesophase is one of amphipathic/lipophilic/vitamin E/water, amphipatic/vitamin E/water, GMO/vitamin E/water, GMO/lipophilic/vitamin E/water, GMO/vitamin E/alcohol/water and GMO/lipophilic/vitamin E/alcohol/water, wherein the alcohol is selected from ethanol and transcutol.

In some embodiments, the at least one lipophilic compound is a medium length TAG such as tricaprylin.

In some embodiments, the mesophases of the invention comprise between 10 and 25 wt % water. In some embodiments, the mesophases comprise between 13 and 23 wt % water, between 10 and 15% water, between 13 and 20% water, between 15 and 20% water or between 15 and 25% water.

In some further embodiments, the mesophases of the invention comprise between 68 and 80% of a mono fatty acid ester, between 7 and 10% of the at least one lipophilic compound and between 10 and 25% water.

In other embodiments, the mesophases comprise between 63 and 73% of a mono fatty acid ester, between 12 and 14% of the at least one lipophilic compound and between 10 and 25% water.

In other embodiments, the mesophases comprise between 71 and 85% GMO, between 4 and 5% tricaprylin and between 10 and 25% water.

As known in the art, one of the limiting factors in the pharmacokinetic behavior of many therapeutic bioactives is their uptake by target cells. Small, uncharged bioactives may permeate across the cell membrane easily. However, for a variety of larger and/or charged bioactives, such as proteins, nucleic acids, and highly water-soluble charged organic compounds, passive uptake cell by permeation across the cell membrane may be so limited as to effectively block uptake into the cells.

The present invention is thus aimed also at providing an extended mesophase system which comprises at least one amphipathic phospholipid to induce a structural change in a lipid membrane upon contact (fusion), said structural change may be one or more of alteration of membrane curvature, modification of surface charge, promotion of nonbilayer lipid phases, and altered phospholipid headgroup spacing within the bilayer.

Thus, the extended ternary mesophase of the invention comprises at least one amphipathic molecule, e.g., a mono fatty acid ester, at least one lipophilic compound and/or at least one antioxidant, at least one phospholipid and at least one organic polar solvent such as an alcohol, such as [amphipathic/lipophilic/antioxidant/phospholipid/alcohol/water].

In some embodiments, the phospholipid is a glycerophospholipid being selected from mono-phosphatidyl glycerols, bis-phosphatidyl glycerols, and tris-phsophatidyl glycerols. Non-limiting examples of such phospholipids are phosphatidyl choline (PC), dipalmitoylphosphatidylcholine, phosphatidyl ethanolamine (cephalin), phosphatidyl inositol, phosphatidyl serine, cardiolipin, plasmalogen, lysophosphatidic acid, phosphatidylinositol (3,4)-bisphosphate, phosphatidylinositol (3,5)-bisphosphate, phosphatidylinositol (4,5)-bisphosphate, phosphatidylinositol 4-phosphate, phosphatidylinositol (3,4,5)-trisphosphate, and phosphatidylinositol 3-phosphate.

In some embodiments, the phosphatidyl ester is phosphatidyl choline (PC), forming the extended ternary system amphipatic/lipophilic/antioxidant/phospholipid/alcohol/water. In some embodiments, the system is GMO/tricaprylin/antioxidant/phospholipid/alcohol/water. In other embodiments, the system is GMO/vitamin E/PC/alcohol/water and in other embodiments GMO/tricaprylin/vitamin E/PC/alcohol/water, wherein the alcohol is as defined above and any combination thereof. In all embodiments and unless otherwise specified, the alcohol may be replaced with a different organic polar solvent.

Thus, in some embodiments, the extended ternary mesophase is one of GMO/tricaprylin/vitamin E/PC/transcutol/water, GMO/tricaprylin/vitamin E/PC/ethanol/water and GMO/tricaprylin/vitamin E/PC/ethanol/transcutol/water.

The mesophase of the invention is capable of solubilizing a bioactive or a biomacromolecule and act as a vehicle for its delivery, e.g., orally or transdermally across a cell membrane. The ability to solubilize one or more hydrophobic and/or hydrophilic materials, permits the formation of a great variety of reservoir vehicles wherein the hydrophobic and/or hydrophilic material may be one or more of a biomacromolecule (bioactive) such as a peptide, a protein, a sugar, an enzyme, and a lipid and a great number of other materials including vitamins, food additives, coloring agents, flavoring agents, therapeutics and others.

Without wishing to be bound by theory and as will be further demonstrated below, solubilization of materials in the hexagonal mesophases may depend to some extent on the ability of the hexagonal mesophase to undergo structural modification, in terms of at least one change in one or more parameters, such as the size of the spacing between the hydrophobic residues of the mono fatty acid esters, the lattice parameter, the size of the cylindrical compartments, i.e., radius and/or length of the cylindrical compartments and expected interactions between the material to be solubilized and the environment. Solubilization may take on one or more of a variety of forms: the solubilized material may be entrapped within the water-rich compartments of the cylindrical micelles, alternatively may be intercalated with hydrophilic or hydrophobic spaces on the outer surface of the micelles, it may intimately interact with one or more moieties of the outer molecular structure of the micelle, or any combination thereof. The ability of the system to undergo structural modification(s) and at the same time provide a multitude of possible interaction environments, renders the mesophases of the invention with the ability of solubilizing hydrophilic materials which are typically water immiscible with the same ease and efficacy as do hydrophilics.

Clearly, the ability of the mesophase systems of the invention to solubilize biomacromolecules is surprising. The ternary mesophase GMO/tricaprylin/water is one such example, where the solubilized biomacromolecule is a protein. Similarly, other hydrophobic and/or hydrophilic materials such as peptides, hormones, proteins, etc, may be solubilized. In some embodiments, the solubilized material is a hydrophilic material being selected amongst vitamins, food additives and therapeutics. In some other embodiments, the hydrophilic material is a hydrophilic antioxidant being selected from vitamin C (ascorbic acid, AA) and esters thereof, carnazol, and folic acid.

In other embodiments, the biomacromolecule, solubilized in a mesophase of the general form amphipathic/lipophilic/water, is selected amongst hydrophilic or hydrophobic peptides, hormones, proteins and other high molecular weight biological materials. In some embodiments, the bioactive is selected from insulin, desmopressin, lysine vasopressin, somatostatin, Renin inhibitor, cytochrome C, myoglobin, lysozyme (LSZ), cyclosporine A (CSA) and chemotripsinogen A; In addition, were solubilized Arixtra (Fondaparinux Sodium), low molecular weight heparin (LMWH) and other drugs.

In some embodiments, the mesophases of the invention or the compositions comprising them comprise at least one pharmaceutically acceptable agent which facilitates release of the biomacromolecule from the mesophase and which may optionally further increase absorption of said biomacromolecule from the gastrointestinal (GI) tract in applications for oral administration. The agent may be contained within the hexagonal mesophase or outside of the mesophase, as further disclosed herein. In some embodiments, the mesophase comprises said at least one agent. In some embodiments, said agent is a hydrolyzing agent. In other embodiments, said hydrolyzing agent is an enzyme, e.g., a lipase.

The present invention therefore additionally provides mesophases as disclosed, and [mesophase]/solute systems as described herein. In some embodiments, the [mesophase]/solute is a system selected from:

[amphipathic/lipophilic/antioxidant/water]/solute
[amphipathic/lipophilic/antioxidant/alcohol/water]/solute
[amphipathic/lipophilic/antioxidant/phospholipid/alcohol/water]/solute
[amphipathic/antioxidant/water]/solute
[amphipathic/antioxidant/alcohol/water]/solute
[amphipathic/antioxidant/phospholipid/alcohol/water]/solute [GMO/vitamin E/water]/solute
[GMO/vitamin E/PC/water]/solute
[GMO/vitamin E/PC/alcohol/water]/solute
[GMO/vitamin E/PC/ethanol/water]/solute
[GMO/vitamin E/PC/transcutol/water]/solute
[GMO/vitamin E/PC/ethanol/transcutol/water]/solute
[GMO/vitamin E/water]/vitamin C
[GMO/vitamin E/PC/water]/vitamin C
[GMO/vitamin E/PC/alcohol/water]/vitamin C
[GMO/vitamin E/PC/ethanol/water]/vitamin C
[GMO/vitamin E/PC/transcutol/water]/vitamin C
[GMO/vitamin E/PC/ethanol/transcutol/water]/vitamin C
[amphipathic/lipophilic/water]/bioactive
[amphipathic/lipophilic/alcohol/water]/bioactive
[amphipathic/lipophilic/phospholipid/alcohol/water]/bioactive
[GMO/TAG/water]/bioactive
[GMO/TAG/alcohol/water]/bioactive
[GMO/TAG/phospholipid/alcohol/water]/bioactive
[GMO/TAG/PC/alcohol/water]/bioactive
[GMO/TAG/PC/ethanol/labrasol/water]/bioactive
[GMO/TAG/phospholipid/alcohol/water/enzyme]/bioactive, and
[GMO/TAG/PC/ethanol/labrasol/water/enzyme]/bioactive;

the labrasol being a caprylocaproyl macrogolglyceride.

In another of its aspects, the invention provides a process for forming a reverse hexagonal mesophase system, said process comprising mixing together at least one amphipathic compound (or a mixture comprising same), at least one lipophilic compound (oil, or a mixture comprising same), and/or (optionally) at least one antioxidant, and optionally at least one additive, in water over a period of time and temperature enabling self-assembly of said reverse hexagonal mesophase. The at least one amphipathic compound, at least one lipophilic compound and the at least one antioxidant (optionally present) are as defined hereinabove.

In some embodiments, the ratio between said at least one amphipatic compound, e.g., a mono fatty acid ester to said at least one lipophilic (antioxidant) compound is between 60:40 and 95:5 (wt %), respectively. In some embodiments, the ratio is between 70:30 and 90:10. In further embodiments, the ratio is 90:10. The water concentration was between 10 and 25%.

The at least one additive which may optionally be added in the process for forming the mesophase is one or more of at least one organic polar solvent (alcohol), at least one hydrophobic material, at least one hydrophilic material, at least one phospholipids, and at least one other material, as disclosed hereinabove.

The period and temperature over which the self-assembly reached steady state varied based on one or more of the quantities of ingredients employed, whether or not the medium was water or a mixture of a polar organic solvent, e.g., alcohol and water, the nature of each of the ingredients, e.g., long chain triglycerides required longer time periods to reach equilibrium, and others. Typically, the assembly was allowed to form over a period of between a few hours and a few days, i.e., 2 hours to about a week, at a temperature between 10 and 80° C.

In another aspect of the present invention, there is provided a pharmaceutical composition for oral delivery comprising a mesophase of the form amphipathic/lipophilic/water or an extended form thereof, as defined above, incorporating at least one biomacromolecule (bioactive) selected from a peptide, a protein, an antibody, a hormone and a synthetic or semi-synthetic drug.

In some embodiments, the hormone is a peptide hormone such as insulin.

The invention also provides an oral delivery system for the delivery of at least one biomacromolecule (bioactive), said system comprising a mesophase of the form amphipathic/lipophilic/water or an extended form thereof, as defined above, and at least one bioactive.

The compositions for oral administration of insulin, comprises an amount of insulin, which is effective for the treatment of diabetes, for the treatment of impaired glucose tolerance, for the purpose of achieving glucose homeostasis, for the treatment of early stage diabetes, for the treatment of late stage diabetes, and/or to serve as replacement therapy for type I diabetic patients. The oral compositions may also be used in methods for prophylactically sparing pancreatic beta cell function and for preventing beta cell death or dysfunction in a mammal that has impaired glucose tolerance or early stage diabetes.

The oral compositions comprising a bioactive such as insulin, may be adapted, as disclosed herein, for long term, immediate or suspended release of the bioactive, e.g., insulin. The compositions of the invention suitable for the treatment of, e.g., diabetes, may be in the form of unit doses.

As used herein, "insulin" refers to insulin from a variety of sources. Naturally occurring insulin and structurally similar bioactive equivalents (insulin analogues including short acting and analogues with protracted action) may be used. Insulin useful in the invention may be obtained by isolating it from natural source, such as different species of mammal. Animal insulin extracted from bovine or porcine pancreas may be used. Insulin analogues, fragments, mimetics or PEG-modified and bioequivalents thereof may also be used. Also, the insulin may be synthetic or semi-synthetic insulin obtained by employing protein chemistry techniques such as peptide synthesis, or by using the techniques of molecular biology to produce recombinant insulin in bacteria or eukaryotic cells. The physical form of insulin may include crystalline and/or amorphous solid forms. In addition, dissolved insulin may be used.

In some embodiments, the insulin is human recombinant insulin, having optionally counter ions including zinc, sodium, calcium and ammonium or any combination thereof.

The invention also provides, in another of its aspects, pharmaceutical compositions for transdermal delivery of bioactives, the compositions comprising a mesophase of the form amphipathic/lipophilic/water or an extended form thereof, as defined above, and at least one biomacromolecule, as defined hereinabove.

The compositions may be suitable for any type of administration, including oral, transdermal, aerosol, parenteral, subcutaneous, intravenous, intramuscular, interperitoneal, rectal, and vaginal administrations.

The compositions of the invention, e.g., for oral or transdermal administration, may be formulated as immediate release formulations, sustained release formulations, as controlled release formulation, and as gradual (step-wise dose) release formulations.

Thus, in another aspect, the invention provides a sustained and/or controlled release drug delivery system comprising a mesophase of the form amphipathic/lipophilic/water or an extended form thereof, as defined above, and a drug contained therein, wherein the mesophase is adapted to release the drug gradually over a period of time after administration. In some embodiments, the system is an oral dose form.

The invention also provides a drug delivery system comprising a mesophase of the form amphipathic/lipophilic/water or an extended form thereof, as defined above, a drug and an enzyme, said drug being contained within said mesophase, wherein the enzyme is adapted to cause degradation of said mesophase, thereby releasing the drug gradually over a period of time after administration. The enzyme may or may not be contained within the mesophase. In some embodiments, the enzyme is contained in the formulation, however, outside of the mesophase.

In some embodiments, the delivery system comprises the enzyme in a separate formulation which does not come into contact with the mesophase until both are administered. In other embodiments, the delivery system comprises the enzyme and the mesophase in a water poor (or dry) environment. The activation of this water-poor (or dry) environment begins when water is introduced and activates the function of the enzyme.

In some embodiments, the drug delivery system is a sustained and/or controlled release system. In some embodiments, the system is an oral dose form.

In another aspect, there is provided a transdermal enhanced drug delivery system comprising a mesophase of the form amphipathic/lipophilic/water or an extended form thereof, as defined above, and a drug contained therein, wherein the mesophase is adapted to deliver the drug transdermally at a rate and/or concentration greater than the rate and/or concentration of the drug when contained in a system different from said mesophase.

The invention also provides an oral drug delivery system comprising a mesophase of the form amphipathic/lipophilic/water or an extended form thereof, as defined above, and a drug contained therein, wherein the mesophase is adapted to deliver the drug orally at a rate and/or concentration greater than the rate and/or concentration of the drug when contained in a system different from said mesophase.

As used herein the term "sustained release" has its ordinary meaning as understood by the skilled in the art, namely the controlled release of a drug from a dosage form over an extended period of time. In some embodiments, sustained-release dosage forms are those that have a release rate that is substantially longer than that of a comparable immediate release form, i.e., the release of a drug from a dosage form in a relatively brief period of time after administration.

The term "release rate" or any lingual equivalent thereof, refers to a characteristic related to the amount of an active ingredient released per unit time as defined by in vitro or in vivo testing.

In accordance with the above, the invention also provides a method of treatment or prevention of diabetes in a subject (human or non-human), comprising orally administering one or more unit doses of the dosage forms described herein.

In some embodiments, the oral insulin composition of the invention is administered to such subjects on a chronic basis and may be administered for the life of the patient.

The invention further provides a process for solubilizing a material, said process comprising providing a reverse hexagonal mesophase system as disclosed herein and admixing at a suitable temperature at least one material.

The mesophase systems of the invention may be utilized for a great variety of applications. Thus, the invention further provides the use of a mesophase system according to the present invention for the solubilization of at least one solute material for the preparation of a composition. The composition may be a pharmaceutical composition or a non-pharmaceutical composition such as a cosmetic composition, a food additive composition, an antioxidant composition, a preservative composition and others.

The invention further provides a method for protecting at least one compound from decomposition, e.g., oxidation; said method comprising solubilizing said at least one compound in a mesophase according to the invention.

In some embodiments, the composition comprising the mesophase/solute system is a pharmaceutical composition for cellular microinjection, i.e., the delivery of the intercalated solute across a cell membrane, in vitro or in vivo. The presence of a molecule which has a tendency to form hexagonal mesophase, as disclosed herein, greatly enhances this fusion process. As used herein, the cell membrane may be that of a living organism, plant or animal; unicellular organisms such as yeasts, algae, fungi, bacteria and the like as well as multicellular organisms or systems including cell cultures and whole animals such as mammals (including humans), reptiles, birds, and the like.

The invention is therefore also directed at providing a method of inserting a foreign material (i.e., the solute material of the mesophase system) into a cell, in vitro or in vivo, said method comprising providing a mesophase composition according to the present invention, intercalating said foreign material and contacting said cell with said mesophase composition, whereby insertion occurs.

The invention is also directed at non-pharmaceutical compositions.

In some embodiment, the composition comprising the mesophase/solute system is suitable for solubilization and protection of at least one food supplement for inclusion thereof into at least one food product or beverage.

In other embodiments, the mesophase may be used as a template for the synthesis of nanostructures. As known, liquid crystals are ideal candidates for controlled nanoparticle synthesis (e.g. metallic nanoparticles and nanostructured conducting polymers). A notable concern in nanoparticle synthesis is the ability to prepare air- and thermally-stable particles of controlled size and dispersity. These nanoparticles may also be repeatedly isolated and re-dissolved in organic solvents without irreversible aggregation and decomposition. The hexagonal columnar phases can be used as templates for the synthesis of mesoporous nanostructures. This results in porous inorganic replicates of the original LLC (upon calcinations). The procedure allows for the production of materials with uniform pore size, morphology, and distribution, in addition to obtaining control over their properties and macroscopic shape.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 6b presents the ratio of the hydrogen-bonded carbonyl groups peak area to the 'free' carbonyls peak area which measured after Gaussian fitting, as a function of lysozyme concentration (wt %) at (○) 13, (▲) 16, (◇) 20 and (■) 23 wt % water in $H_{II}$ mesophase.

FIG. 26A—Below T=35° C., interfacial water stabilizes the lipid layer via its interaction with the GMO head γ OH group. Consequently, the TAG molecule remains intercalated between the tails. Dangling tails of the PC group give rise to counter ion movement and also TAG dipolar relaxation. FIG. 26B—Above T=307 K, the interface is destabilized by the breakdown of the interfacial water layer. The perturbation of the PC heads leads to greater dangling, enabling diffusive movement of the TAG molecule through the tails.

FIG. 27A is a schematic presentation of the supramolecular organization of $H_{II}$ mesophase, showing the cylinders' packing. FIG. 27B is a schematic illustration focused on one cylinder of the mixed surfactant (GMO and PC) hexagonal system organization. Note that GMO and PC polar moieties are hydrated, but that TAG is located between the lipophilic chains of the surfactants.

FIG. 32a Random coil, FIG. 32b α helix and FIG. 32c β-sheet content of calcitonin when incorporated into the $H_{II}$ mesophase (as function of time at pH of 3, 5, 7 and 9).

FIG. 33a (■) control-untreated rats, and FIG. 33b (●) via hexagonal liquid crystals.

DETAILED DESCRIPTION OF EMBODIMENTS

Generally, mesophases of the form amphipathic/lipophilic/water or extended forms thereof have been prepared by mixing together at least one amphipathic compound (or a mixture comprising same), at least one lipophilic compound (oil, or a mixture comprising same), optionally at least one antioxidant (introduced in addition to or in place of said at least one lipophilic compound), and optionally at least one additive in water over a period of time and temperature enabling self-assembly of the reverse hexagonal mesophase. The at least one amphipathic compound, at least one lipophilic compound, the at least one antioxidant (optionally present) and the at least one additive are as defined hereinabove.

Typically, the ratio between the at least one amphipathic compound, e.g., a mono fatty acid ester to said at least one lipophilic (antioxidant) compound is between 60:40 and 95:5 (wt %), respectively. Other ratios such as any such ratio between 70:30 and 90:10 have also been used. The water concentration was typically between 10 and 25% of the total weight of the formulation.

The at least one additive which may optionally be added in the process for forming the mesophase is one or more of at least one organic polar solvent (alcohol), at least one hydrophobic material, at least one hydrophilic material, at least one phospholipids, at least one other material as disclosed hereinabove, e.g., an enzyme.

The period and temperature over which the self-assembly reached steady state varied based on one or more of the quantities of ingredients employed, whether or not the medium was water or a mixture of a polar organic solvent, e.g., alcohol and water, the nature of each of the ingredients, e.g., long chain triglycerides required longer time periods to reach equilibrium, and others. Typically, the assembly was allowed to form over a period of between a few hours and a few days, i.e., 2 hours to about a week, at a temperature between 10 and 80° C.

In the following examples, specific embodiments of the invention are demonstrated. As a person skilled in the art would appreciate, the examples provided are mere examples of the scope and versatility of the herein disclosed invention and therefore should not be taken as limiting the scope of protection.

A. GMO/Tricaprylin/Water Mesophase

Distilled glycerol monooleate comprising of 97.1 wt % monoglyceride and 2.5 wt % diglyceride and free glycerol (0.4%) (acid value 1.2, iodine value 68.0, melting point 37.5° C.) were purchased from Riken (Tokyo, Japan).

Tricaprylin (triacylglycerols, TAG; assay 97-98%) was obtained from Sigma Chemical Co. (St. Louis, Mo., USA). Water was double distilled.

All ingredients were used without further purification.

Figure 23:
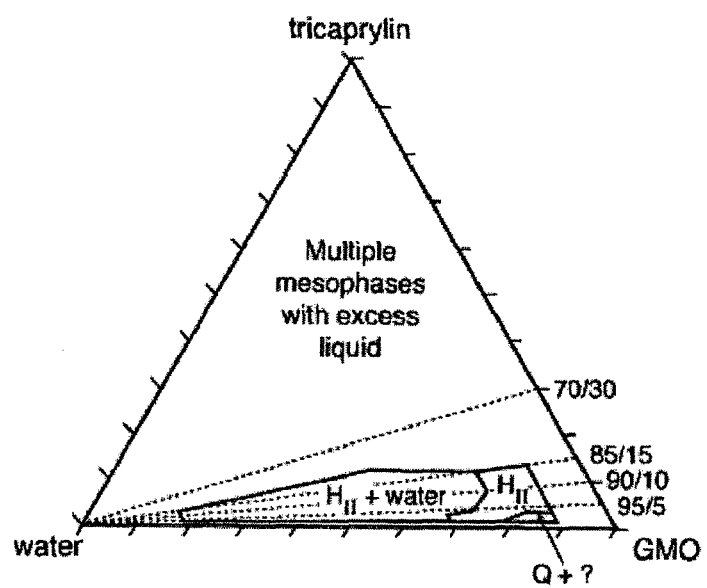
FIG. 23 presents the ternary phase diagram of GMO/tricaprylin/water at 25° C. The dilution lines represent the surfactant/oil weight ratio.

The GMO/tricaprylin/water hexagonal liquid crystalline samples were formed by mixing all the components while heating to ~70° C. in sealed tubes under nitrogen (to avoid oxidation of the GMO) for ca. 15 min. The phase diagram (FIG. 23) was divided into dilution lines which represented a constant weight ratio between the GMO and tricaprylin, i.e., dilution line 90/10 means 90 wt % GMO and 10 wt % tricaprylin. All samples were stirred and kept in a 25±0.5° C. water bath.

B. GMO/tricaprylin/water Mesophase Solubilizing Biomacromolecules

The elucidation of the mode of entrapment and interactions of a biomacromolecule, e.g., a protein such as LSZ, as well as others as further demonstrated below, with the mesophase components, conformation of the protein and its stability under varying pH and denaturation conditions and structural changes in the hexagonal mesophase, using SAXS, ATR-FTIR, and rheological methods are disclosed.

Lysozyme, LSZ, (14.4 KDa) is a hydrophilic protein that has been well characterized and widely used as a model for numerous scientific studies, such as enzymatic reactivity, protein stability, and crystallization. Its solubilization in the cubic phase was also investigated, showing that the cubic phase did not destroy the enzyme activity. Examination of the physical properties of the cubic phase indicated that the LSZ was embedded in the water channels of the structures [5].

Lysozyme was solubilized in water in the range of 1-25 wt %, and the solution pH was adjusted to 4.5 with an appropriate amount of NaOH and/or HCl. The GMO/tricaprylin/LSZ/water hexagonal liquid crystals were prepared by mixing weighed quantities of GMO and tricaprylin (9:1 weight ratio) with LSZ solution while heating to 40° C. It should be noted that as a result of lysozyme solubilization the concentrations of GMO and tricaprylin were decreased, keeping their weight ratio of GMO/tricaprylin (9:1) and water content constant.

Lysozyme was solubilized into the $H_{II}$ mesophases of GMO/tricaprylin/water containing, in some specific examples, 13, 16, 20 and 23 wt % water. The solubilization of the protein into the structures was found to be water concentration-dependent. The samples containing 13 or 16 wt % were able to accommodate only 1 and 2 wt % LSZ, respectively, while 3-3.5 wt % protein were solubilized into the water-richer structures (20 and 23 wt %).

The mesophases were classified according the degree of order, categorized as less ordered at a relatively low (<20 wt %) water content and as well-ordered structures at a higher (>20 wt %) water content. Due to the high hydrophilicity of LSZ, it seems reasonable to suggest, with no intent of being bound to a specific mode of action or mechanistic analysis, that the protein is embedded within the water cylinders of the hexagonal structure. This could be correlated with previous studies which indicated that the protein was located in the water channel system of the cubic phase of GMO and water. Therefore, with the mesophases of the present invention having larger lattice parameter (and thus increased radius of cylindrical water micelles) and a higher degree of order, a better solubilization capacity is expected and indeed demonstrated.

Figure 1:
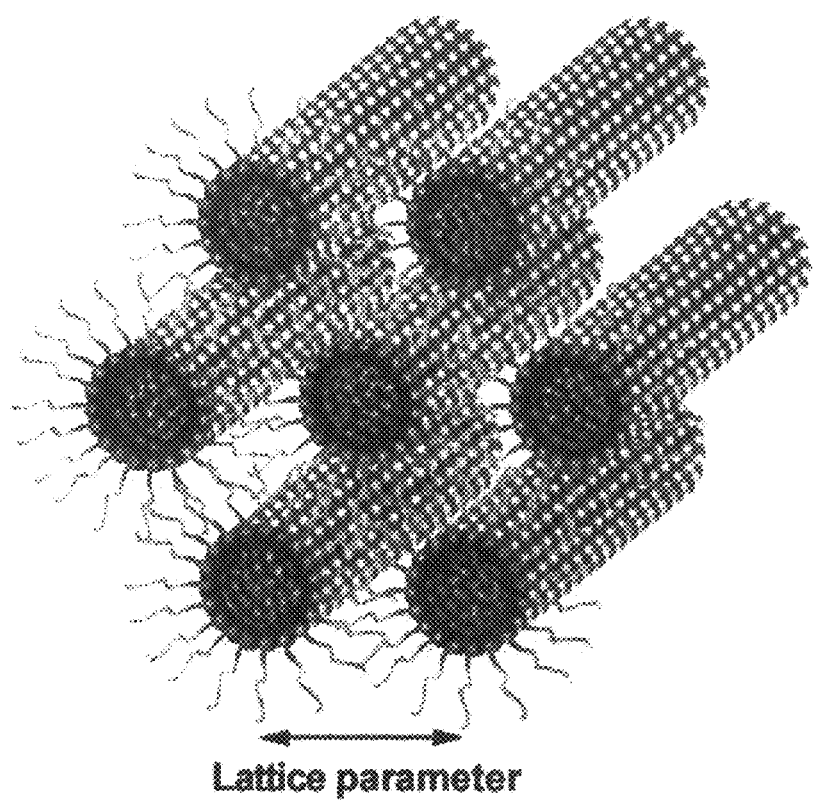
FIG. 1 is a schematic representation of the $H_{II}$ mesophase structure.
Figure 2A:
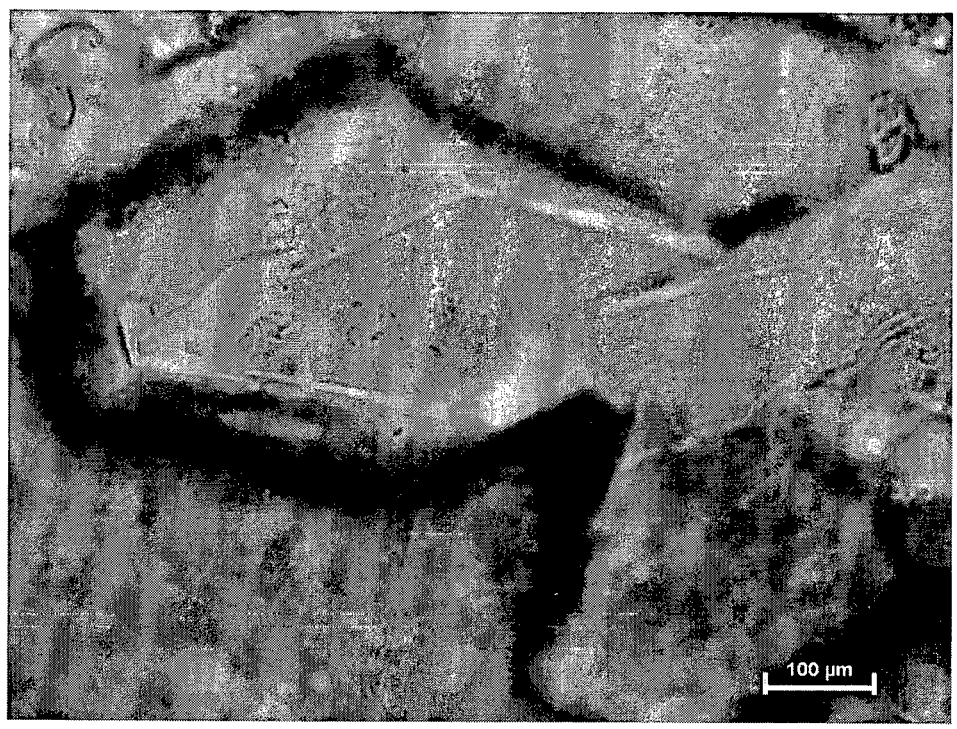
FIGS. 2a-b present photomicroscope images of crystallization of lysozyme at hexagonal mesophases containing (a) 20 wt % water and (b) 13 wt % water.
Figure 2B:
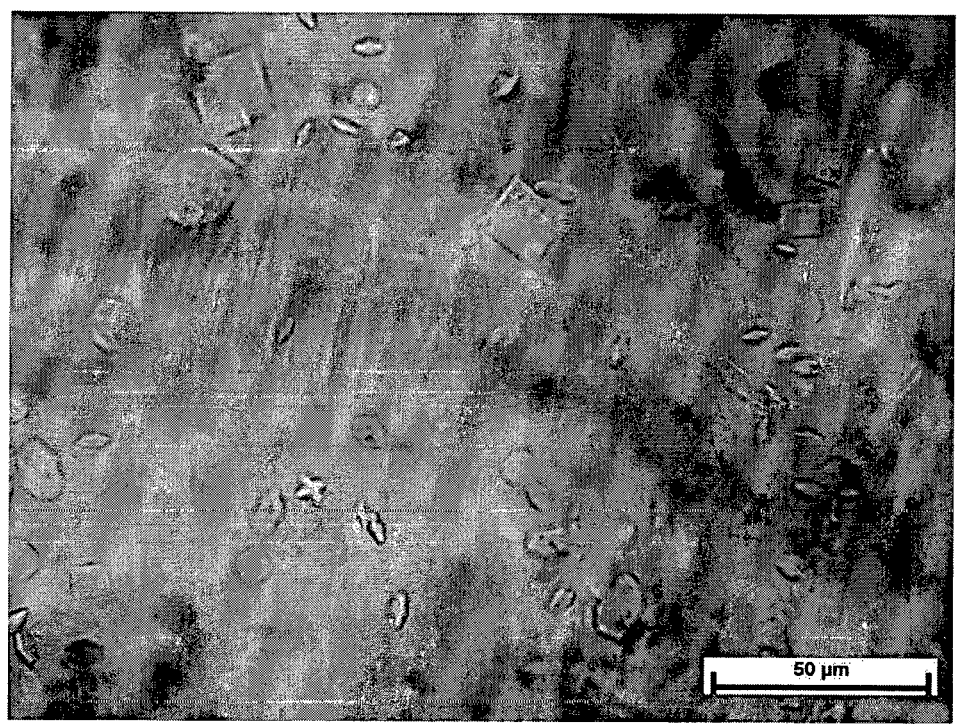

Attempts to solubilize larger amounts of LSZ than as compared to the accommodation capacity caused crystallization of the protein or precipitation in very high concentrations. As depicted in FIG. 2a, single plate-like crystals of 300 micrometers of LSZ were obtained, mainly from hexagonal phases having 20 and 23 wt % water. Utilizing samples having lower water concentrations led to a noticeable decrease in the size and number of such crystals as shown in FIG. 2b. This observation indicates that the nucleation process is dominant over growth in the less swelled and less ordered water-poor samples. LSZ was also crystallized from the monoolein based cubic phases. However, in contrast to the crystallization in the $H_{II}$ mesophases, use of the cubic phases of the art demonstrated that nucleation and growth of lysozyme crystals are independent of the type of cubic phase and the packing arrangements of the lipidic compartments. Hence, this may propose a different mode of interaction between the protein and monoolein in the water compartments of the $H_{II}$ mesophase, as compared with the cubic phases, which is probably responsible for the composition and structure dependable crystallization of LSZ within the hexagonal mesophases.

1. Small-Angle X-Ray Scattering (SAXS) Measurement

Scattering experiments were performed using Ni-filtered Cu Kα radiation (1.54 Å) from an Elliott rotating anode X-ray generator operating at 1.2 kW. X-radiation was further monochromated and collimated by a single Franks mirror and a series of slits and height limiters, and measured by a linear position-sensitive detector. The samples were held in 1.5 mm quartz X-ray capillaries inserted into a copper block sample holder. The temperature was maintained at T±0.5° C. with a re-circulating water bath. The camera constants were calibrated using anhydrous cholesterol. The scattering patterns were de-smeared using the Lake procedure implemented in computer software.

Figure 3:
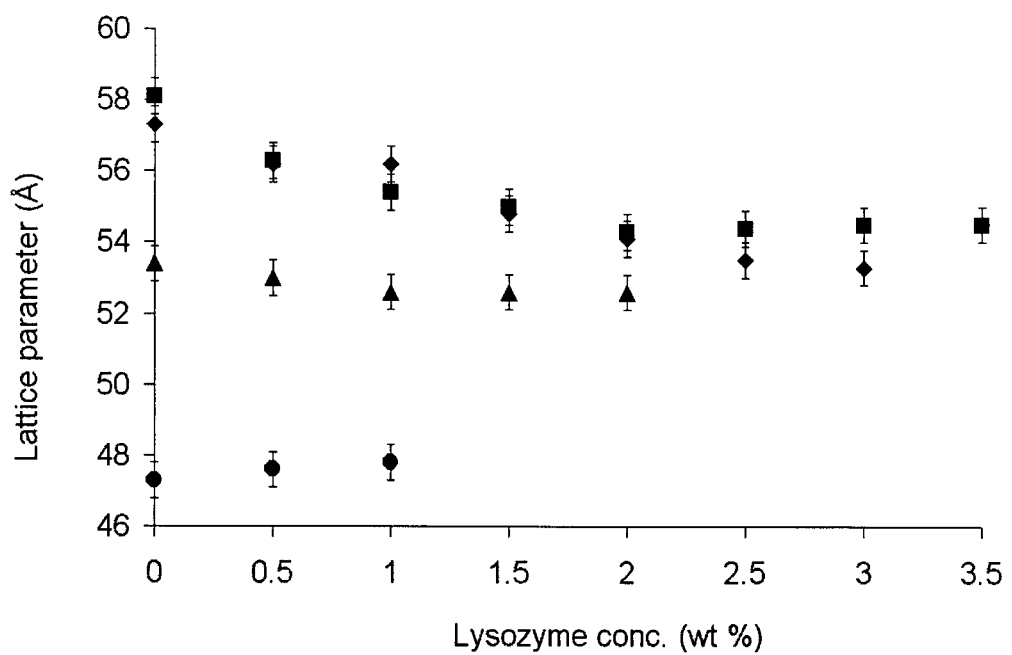
FIG. 3 presents the lattice parameter (Å) of $H_{II}$ containing GMO/tricaprylin with a weight ratio of 9:1, as a function of lysozyme concentration (wt %) at (●) 13, (▲) 16, (◆) 20 and (■) 23, and wt % water.

SAXS measurements were performed in order to follow and evaluate the effect of LSZ solubilization on the lattice parameter of the hexagonal structures, having varying water concentrations at pH 4.5 (FIG. 3).

A decrease of up to 4 Å in the lattice parameter of the high water content mesophases (20 and 23 wt %) was observed in the presence of 3 wt % of the guest molecules. The moderate shrinking of the lattice parameter pointed to the partial dehydration of the hydrophilic heads of the monoglyceride employed in the mesophase, probably due to a competition for water binding between the LSZ and the polar moieties of the surfactant. At the same time, almost no effect on the lattice dimensions was detected in the mesophases with lower water content (13 and 16 wt %). Without wishing to be bound by theory, such a difference is explained by examination of the structural dimensions of the protein and the water cylinders of the hexagonal mesophases. The molecular diameter of LSZ is about 30 Å. Considering the geometric structure of the hexagonal phase, and using the obtained lattice parameter α from the SAXS measurements, the radius of the water cylinders $R_W$ can be calculated according to Eq. 1:

$$R_w = \alpha \left( \frac{\sqrt{3}(1-\varphi_{lip})}{2\pi} \right)^{1/2} \quad \text{Eq. 1}$$

where $\varphi_{lip}$ is the total lipid volume fraction for the ternary mixtures, which was calculated according to Eq. 2:

$$\varphi_{lip} = \frac{\frac{\omega_{GMO}}{\rho_{GMO}} + \frac{\omega_{TAG}}{\rho_{TAG}}}{\frac{\omega_{GMO}}{\rho_{GMO}} + \frac{\omega_{TAG}}{\rho_{TAG}} + \frac{\omega_{H_2O}}{\rho_{H_2O}}} \quad \text{Eq. 2}$$

In Eq. 2, ω is the weight fraction of the component and ρ is the density of the components (0.94 for GMO, 0.95 for TAG, and the 1.0 g/cm³ for $H_2O$). The calculated radii of the $H_{II}$ mesophases containing GMO/tricaprylin at a constant weight ratio of 9:1 and varying water concentrations of 13, 16, 20 and 23 wt % was 8.7, 10.9, 13.1 and 14.3±0.5 Å, respectively. These results indicate that the diameters of the cylinders in the presence of 20 and 23 wt % water possess lower values, compared to the diameter of lysozyme. Moreover, the dimensions of the water cylinders containing 13 and 16 wt % water are much lower than the protein diameter. Hence, from a structural point of view, the protein has to be intercalated in the interface region in order to fit the narrow water cylinders. In such a case, the embedment of LSZ into the interface region should increase the lattice parameter of the structures and this effect was expected to be more pronounced at lower water content. Nevertheless, the possibility of partial dehydration of the hydrophilic heads of GMO, which should lead to a decrease in the lattice parameter, analogous to the higher water content mesophases, could not be ruled out. Therefore, the net effect of the two competing processes was reflected by keeping the lattice dimensions intact.

2. ATR-FTIR Analysis

To examine closer the phenomenological influence of LSZ, as an exemplary biomacromolecule, on the structures of the invention and to obtain a molecular level insight on the mutual protein-carrier interactions, ATR-FTIR analysis was utilized.

An Alpha model spectrometer, equipped with a single reflection diamond ATR sampling module, manufactured by Bruker (Ettlingen, Germany), was used to record the FT-IR spectra (GMO/TAG/LSZ/water). The spectra were recorded with 50 scans, with spectral resolution of 2 $cm^{-1}$, at room temperature. The absorbance intensities reported here were reproducible to ±0.005.

Figure 4:
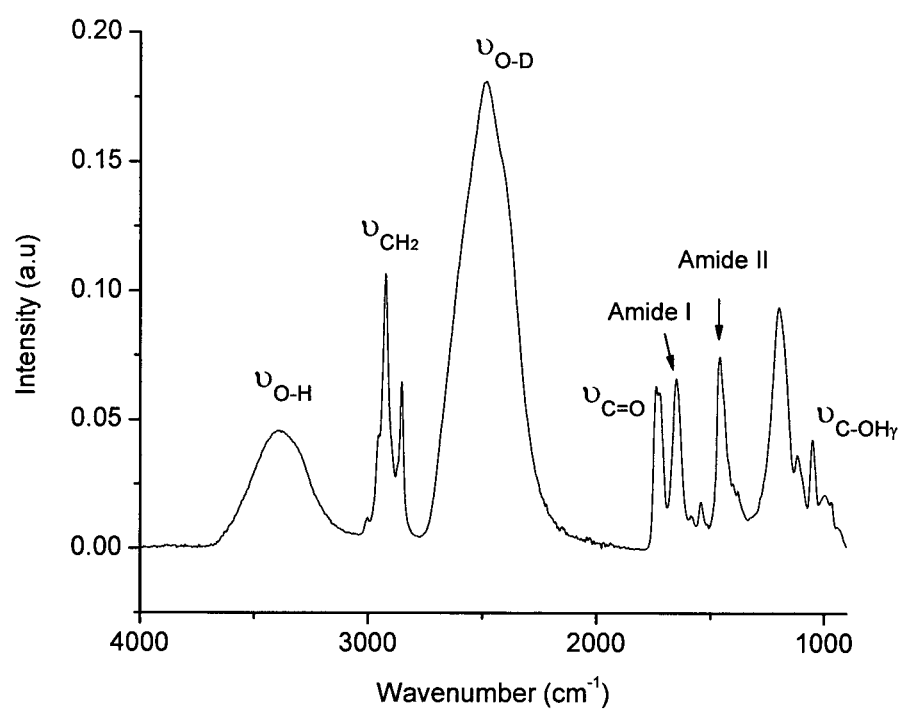
FIG. 4 presents a representative ATR-FTIR spectrum of $H_{II}$ mesophase of GMO/tricaprylin/LSZ/water system.

The mutual influence of the LSZ on the structure of the GMO/tricaprylin/LSZ/water mesophases was elucidated using $D_2O$ instead of $H_2O$ to avoid the influence of the water OH bending on the amide I' band of LSZ. The resolved bands, reflecting the influence of LSZ on the $H_{II}$ mesophase, are presented in Table 1 below and FIG. 4. Prior to the FTIR measurements, the hexagonal structure was confirmed to exist despite the use of $D_2O$, at the same hydration levels (13-23 wt %). A slight increase of 2.5 Å in the lattice parameter was monitored when $D_2O$ was used, as compared to the $H_2O$ based samples, which was attributed to the tighter bonding of $D_2O$ with the surfactants hydrophilic moieties (data not shown).

TABLE 1

ATR-FTIR band positions of $H_{II}$ GMO/tricaprylin/LSZ/water mesophase system, in the 1000-4000 $cm^{-1}$ range at 25° C.

| Type of vibration | $\upsilon$ ($cm^{-1}$) |
|---|---|
| sn-3 C—OH stretching (GMO) | 1050 |
| C—O stretching (TAG) | 1095 |
| sn-2 C—OH stretching (GMO) | 1118 |
| sn-1 CO—O (ester) stretching (GMO) | 1162-1167 |

TABLE 1-continued

ATR-FTIR band positions of $H_{II}$ GMO/tricaprylin/LSZ/water mesophase system, in the 1000-4000 cm$^{-1}$ range at 25° C.

| Type of vibration | $\upsilon$ (cm$^{-1}$) |
|---|---|
| D$_2$O bending | 1197-1203 |
| Amide II in D$_2$O | 1450 |
| Amide II in H$_2$O | 1550 |
| Amide I | 1600-1700 |
| sn-1 hydrogen-bonded C=O stretching(GMO) | 1725 |
| sn-1 'free' C=O stretching (GMO) | 1743 |
| D$_2$O stretching(asymmetric + symmetric) and overtone of bending | 2500 |
| CH$_2$ symmetric stretching | 2853 |
| CH$_2$ antisymmetric stretching | 2924 |
| C=CH | 3001 |
| OH stretching (GMO) | 3372-3391 |

Figure 5A:
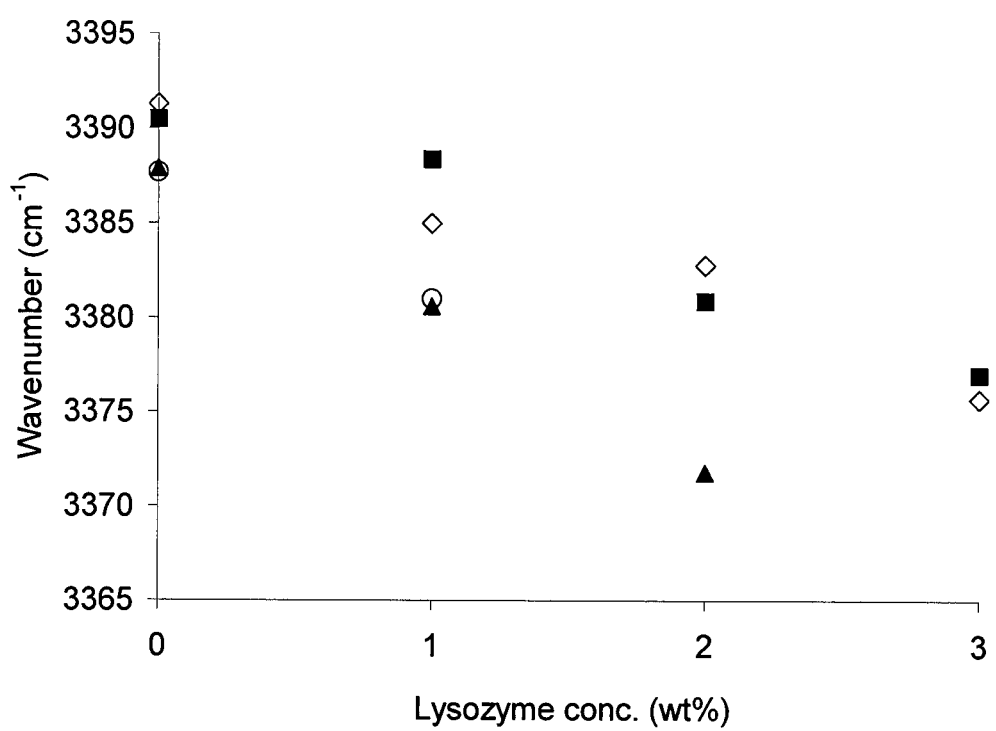
FIGS. 5a-b present (a) ATR-FTIR frequency ($cm^{-1}$) and (b) width at half height ($cm^{-1}$) as a function of lysozyme concentration (wt %) at (○) 13, (▲) 16, (◇) 20 and (■) 23 wt % water in $H_{II}$ mesophase.

Following the assumption that LSZ was intercalated within the water channels, the absorption bands at 3200-3400 cm$^{-1}$, attributed to the O—H stretching modes ($\upsilon_{OH}$) of GMO were examined. As a rule, the stronger the hydrogen bonding between the surfactant O—H groups and the D$_2$O, the lower is the stretching frequency of the O—H group ($\upsilon_{OH}$). Samples containing 13 and 16 wt % water initially exhibited lower $\upsilon_{OH}$ compared to higher water content structures of 20 and 23 wt % (3387 vs. 3391 cm$^{-1}$). In the hexagonal systems with increasing aqueous phase concentration, the water activity was increased, transforming from the slightly bound to the free state, implying stronger hydrogen bonding between the monoolein and water at low water content. Upon solubilization of LSZ, the position of the $\upsilon_{OH}$ showed a visible shift to lower wave numbers (up to 15 cm$^{-1}$ at 3 wt % of LSZ), suggesting stronger hydrogen bonding between the hydroxyls of GMO and its environment, which includes D$_2$O and LSZ (FIG. 5a).

Figure 5B:
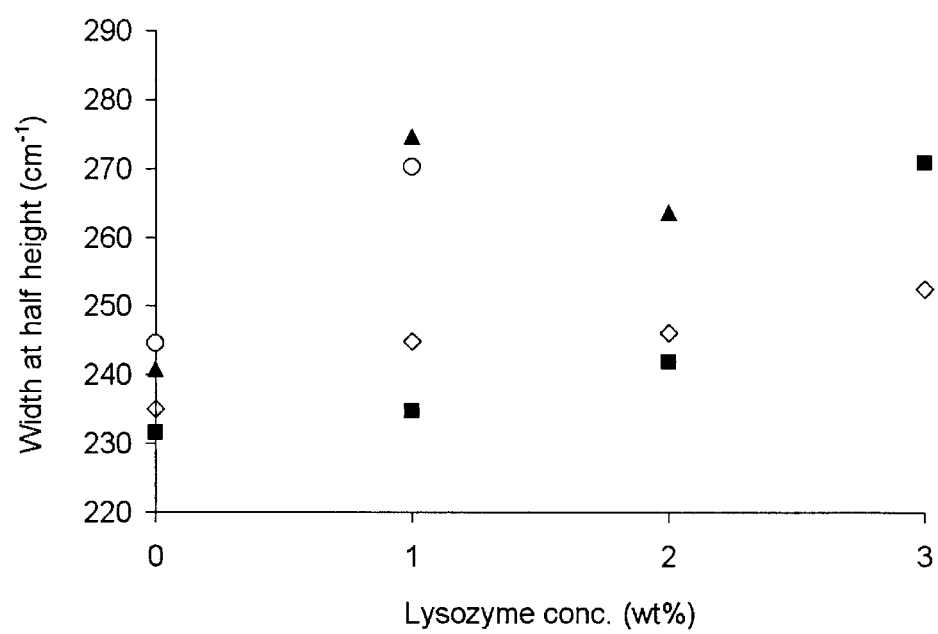

Moreover, the downwards shift of the $\upsilon_{OH}$ position was accompanied with the enhancement of the half-width of this band, suggesting a decrease in the packing order of the monoolein O—H groups, as a result of LSZ solubilization (FIG. 5b). Hence, it may be inferred that hydrogen bonding of the O—H groups of GMO with the protein is the reason for the observed downward shift in the $\upsilon_{OH}$ position and the increase of the half-width of the band.

To determine whether the localization of LSZ in the water channels affected the packing of the acyl chains of the surfactants, the specific IR peaks of GMO methylene groups at 2853 cm$^{-1}$ (symmetric stretching) and at ~2918 cm$^{-1}$ (antisymmetric stretching) were studied. It is widely accepted that the absorption at 2853 cm$^{-1}$ is associated with the conformational order of the lipid chain, which reflects the instantaneous state of organization of the membranes. This band at 2853 cm$^{-1}$ is also known to be rather sensitive to trans-gauche isomerization within the chain. No significant changes in the frequency of these bands were observed. However, CH$_2$ wagging mode in the IR spectral region of 1330-1400 cm$^{-1}$ was observed (data not shown). An inspection of this spectral mode, consisting of the end-gauche band (eg) at ~1341 cm$^{-1}$, the double gauche band (gg) at ~1354 cm$^{-1}$, and the band of gauche-trans-gauche (kink) at ~1367 cm$^{-1}$), similarly did not reveal any change. It was, therefore concluded, that no isomerization process in the systems was involved as a result of LSZ inclusion.

Figure 6A:
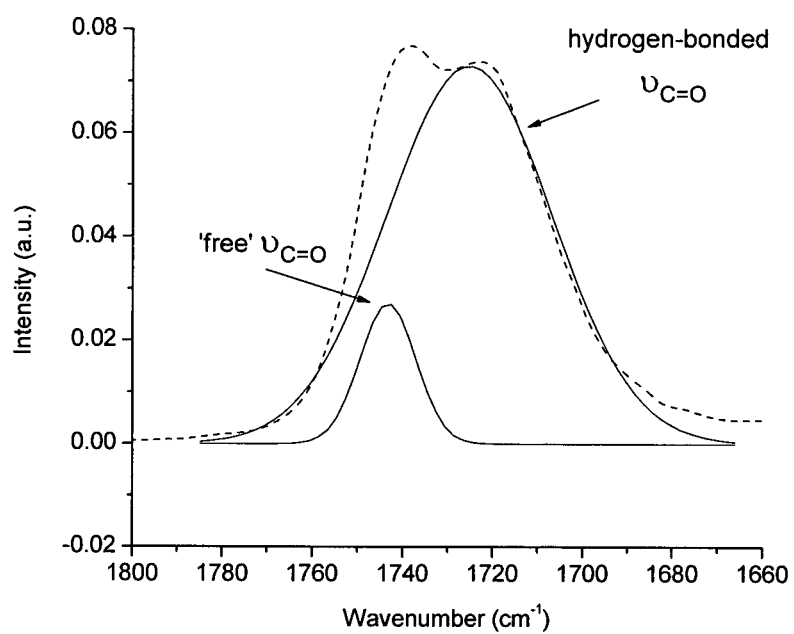
FIGS. 6a-b present (a) representative multi-peaks Gaussian fitting of the carbonyl band indicating two C=O populations: 'free' carbonyls (1743 $cm^{-1}$) and the hydrogen-bonded carbonyl groups (1727 $cm^{-1}$).

The carbonyl absorption mode was shown to be sensitive to protein-surfactant interactions. This band in the spectra of the systems of the invention consisted of two separated peak maxima, indicating that the carbonyl was exposed to two different environments: the first one originating from 'free' carbonyls (1743 cm$^{-1}$) and the second one originating from intramolecularly hydrogen-bonded carbonyl groups (1725 cm$^{-1}$) with γ-OH hydroxyl groups (FIG. 6a).

Figure 6B:
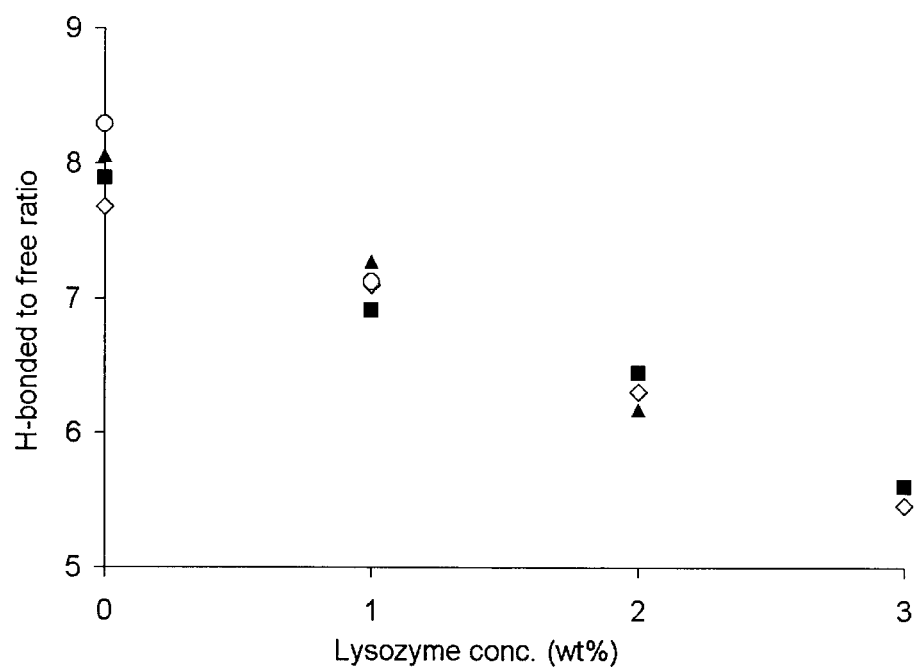

Comparing the peak areas of the free and hydrogen-bonded carbonyls provided a quantitative tool for estimating the populations' ratio of these groups. As shown in FIG. 6b, the ratio of the hydrogen-bonded carbonyls in the empty system to free carbonyls was about 7.7-8.3. However, the embedding of the protein into the mesophase reduced this ratio, regardless of the chemical composition of the mesophases. The decrease in the hydrogen bonded carbonyls population was especially pronounced at high LSZ concentrations (from 7.9 to 5.6) in water-rich samples. This findings may be attributed either to the partial dehydration of the carbonyls or to partial cleavage of the hydroxyl-carbonyl intramolecular hydrogen bonds due to the presence of the protein.

Figure 7A:
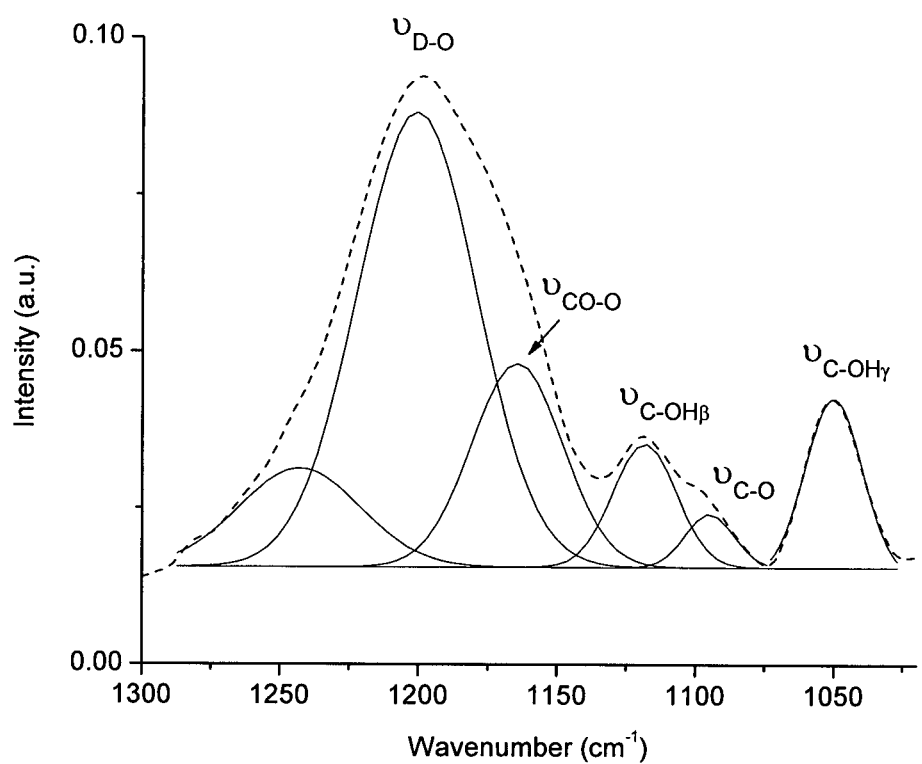
FIGS. 7a-b present (a) representative multi-peaks Gaussian fitting of the $H_{II}$ mesophases and (b) the CO—O bond frequency ($cm^{-1}$) as a function of lysozyme concentration (wt %) at (○) 13, (▲) 16, (◇) 20 and (■) 23 wt % water in $H_{II}$ mesophase.

To further clarify this issue, the two hydroxyls stretching modes C—OH (β, ~1117 cm$^{-1}$), C—OH (γ, ~1051 cm$^{-}$) were analyzed by fitting the observed spectra with multiple Gaussians, reflecting the interfacial packing of the lipid headgroups (FIG. 7a).

The analysis of the stretchings showed that no significant changes occurred at the described bands, mainly responsible for hydroxyl-carbonyl intramolecular hydrogen bonds. Therefore, it is likely that the decrease in the hydrogen bonded carbonyls population was induced by dehydration of the monoolein carbonyls and not by the cleavage of the hydroxyl-carbonyl intramolecular hydrogen bonds.

Figure 7B:
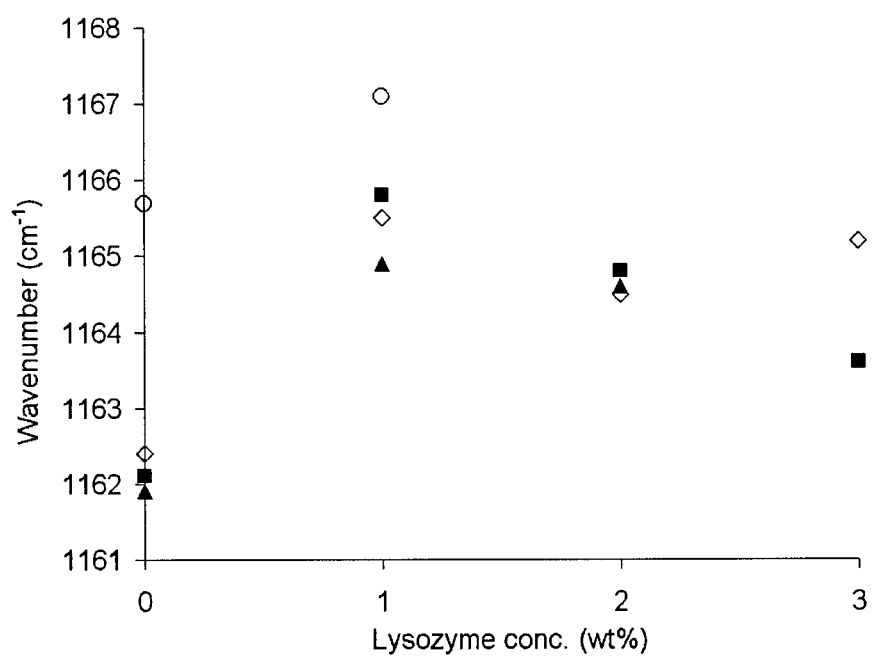

Next, the CO—O bond (ester) stretching mode of GMO was examined (FIG. 7a). The absorption maximum was resolved by the multi-Gaussian fitting at ~1162 cm$^{-1}$ at 16, 20, and 23 wt % water and 1166 cm$^{-1}$ at 13 wt % water. The solubilization of LSZ gave rise to a gradual shift of this band towards higher wave-numbers with increasing protein concentration (FIG. 7b). As known, the low frequency position of the CO—O band may be associated with a deviation from the dihedral angle of 180° in this segment, induced by torsional motions or by a small population of gauche conformers near the sn-1 CO—O single bond. The lower frequency positions of the CO—O band correspond to more disordered states of the lipids. Therefore, it may be concluded that the incorporation of LSZ, which induced a higher frequency position of CO—O band, implied a more ordered state of the CO—O groups of GMO.

Based on the FTIR and SAXS experimental results, it could be concluded that LSZ interacts with the hydroxyls of GMO in the outer interface region and simultaneously induces dehydration of the monoglyceride carbonyls. The interactions of LSZ with hydroxyls of GMO can potentially increase the lattice parameter of the structures while the dehydration of the carbonyls causes the opposite effect. This mechanism of molecular interactions of the two competing trends is probably responsible for the moderate decrease of lattice parameter in water-rich samples or no effect on the lattice dimensions in water-poor samples.

When comparing the entrapment of lysozyme, as disclosed herein, with the entrapment of LSZ in the water channel system of the Pn3m monoolein-H$_2$O cubic phase the following unexpected and beneficial conclusions may be drawn: (1) up to 8 wt % of lysozyme was solubilized in the cubic phase; (2) a phase transformation from Pn3m into Im3m and an increase in the lattice parameter of the latter took place; (3) an increase in the relative number of hydrogen-bonded C=O groups of monoolein occurred. The major structural differences between the examined $H_{II}$ and cubic phases are higher water content (39 wt %) and consequently bigger radius of the water tubes of the latter, and higher curvature of the hexagonal phase. It seems that higher solubilization ability of LSZ in the cubic phase compared to the hexagonal mesophases (8 via 3 wt % respectively) may be assigned to its higher water content and swollen cylinders. The opposite trend in the behavior of the carbonyl groups of monoolein is probably dictated both by the higher curvature and lower water content that encourage competition for water between LSZ and GMO leading to partial dehydration of the carbonyl groups. On the other hand, the high curvature and relatively low water concentration implied LSZ interactions with monoolein via hydrogen bonds within the hexagonal phase, which was not detected with the cubic one.

Following this interpretation, the LSZ interactions with the polar moieties of monoglyceride can potentially effect the conformation of the protein and its stability within the $H_{II}$ mesophase as compared with the water solution.

3. pH Influence

Figure 8A:
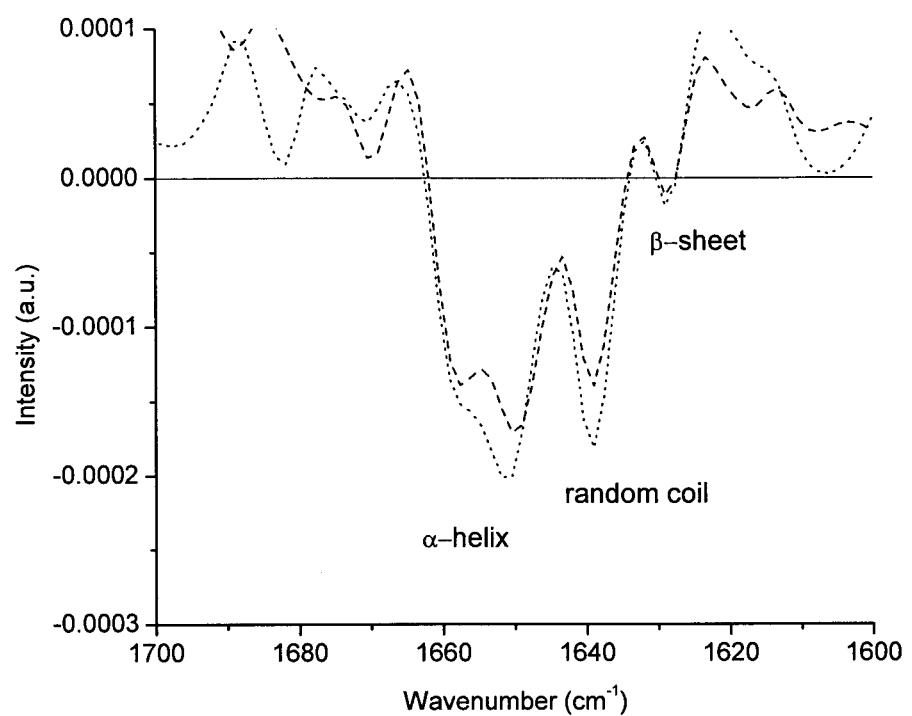
FIGS. 8a-c present (a) ATR-FTIR secondary structure analysis of the amide I' band of the GMO/tricaprylin/LSZ/water system (- - -) and of LSZ solution in $D_2O$ (······); at pH=5.85; (b) α-helix and (c) random coil content as a function of pH in the (▲) GMO/tricaprylin/LSZ/water system and (■) in LSZ solution in $D_2O$.
Figure 8B:
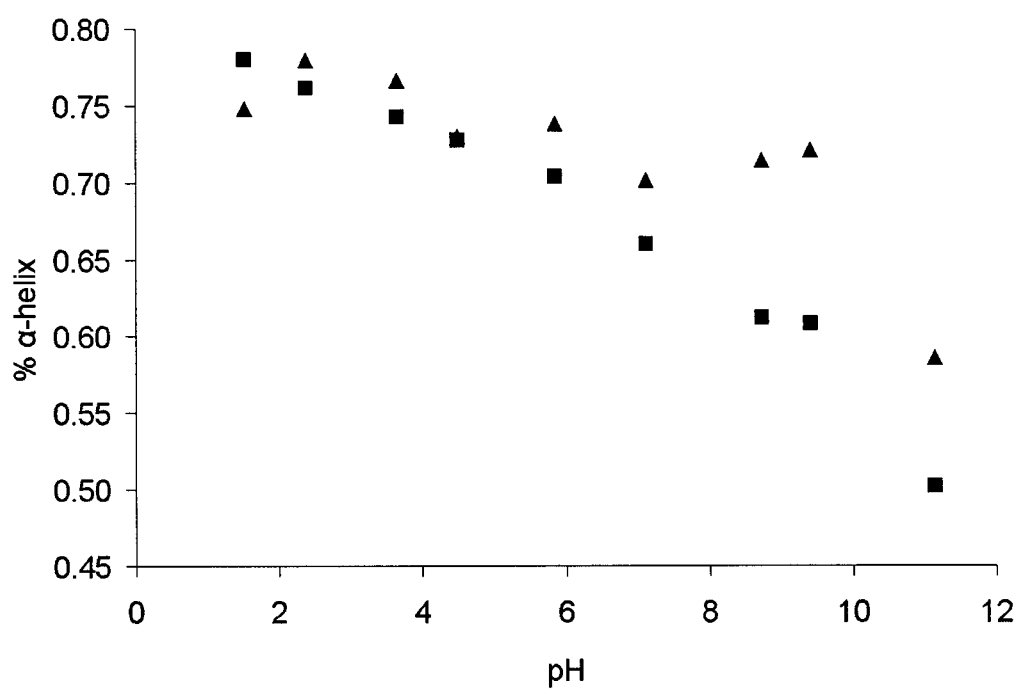
Figure 8C:
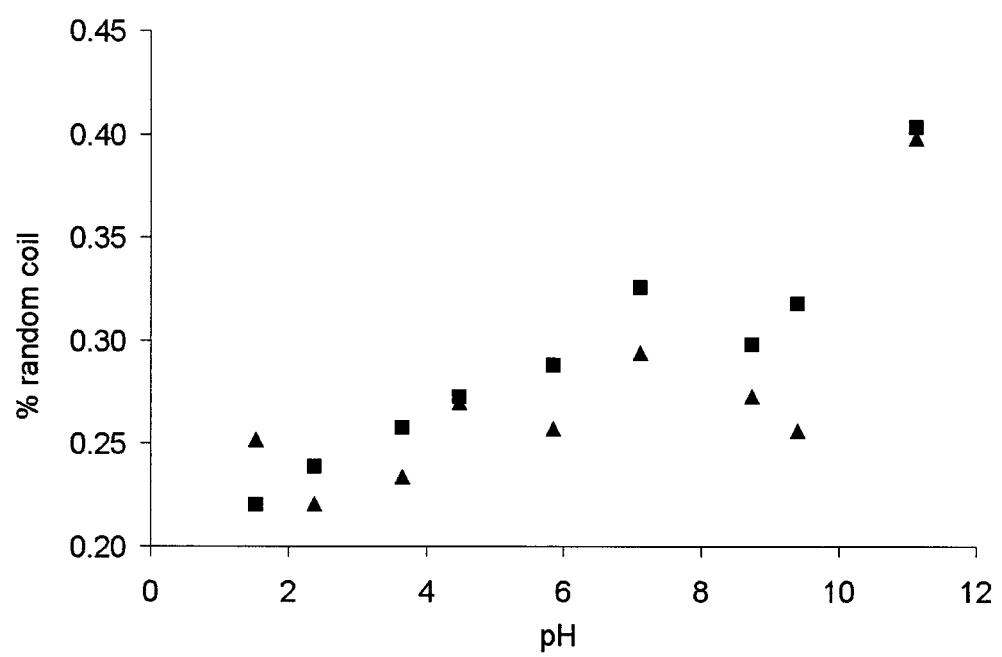

The secondary structure of LSZ was analyzed by means of ATR-FTIR. The representative amide I' spectra of the protein solubilized in the $H_{II}$ mesophases and $D_2O$ solution at pH 5.85 are presented in FIG. 8a. The measured amide I' band of LSZ was resolved by second derivative analysis, which is a well-established technique allowing decomposition of the amide I' contours into the contributing components. The absorptions appeared between 1620 and 1660 cm$^{-1}$ as shown in FIG. 8a. The experimental results demonstrated that in $D_2O$ two major absorption bands appeared, characteristic of α-helix and random coil structures at 1650 and 1639 cm$^{-1}$, respectively. LSZ is more stable and soluble in water in low pH values. As the pH approaches the isoelectric point of LSZ ($I_{EP}$=11.2), the increase of pH leads to a decrease in the protein net charge and consequently weakens electrostatic repulsions and solubility. Such a trend also influenced the conformation of the protein in $D_2O$. Increasing pH induced lower values of α-helix content (from 0.78 at pH of 1.5 to 0.5 at pH of 11.14), as demonstrated in FIG. 8b and higher values of random coil structure (from 0.22 at pH of 1.5 to 0.4 at pH of 11.14), as shown in FIG. 8c, indicating less conformational stability of LSZ at higher pH conditions.

Conformational stability of the protein was significantly affected by its incorporation into the hexagonal phase. At lower pH, ranging from 1.5 to 6, no modifications in the secondary structure were monitored. In contrast, at higher pH, from 6 to 11, where LSZ is normally less stable in water, the content of the α-helix conformation was considerably higher (FIG. 8b) and the content of random coil structures was lower (FIG. 8c) within the $H_{II}$ mesophases, as compared to $D_2O$.

As the α-helix conformation of LSZ is considered hydrophilic and the surface of the protein is considered to mostly consist of this structural element, the LSZ hydrogen bonding with hydroxyls of GMO, showed by the spectroscopic measurements, can be mostly assigned to the interactions of the α-helix with the O—H groups of the surfactant. In other words, these interactions stabilize the helical structure of LSZ at high pH conditions, where it is less stable in water. These results suggest that the solubilization of LSZ into the hexagonal carriers enables it to be used for enzymatic activity also at a higher pH range where it possesses increased conformational stability, as compared to its solubilization in a water solution. In other words, LSZ has higher stability at chemical denaturation conditions, as further verified in the following study in the presence of urea as a denaturating agent.

4. Urea Effect

The α-helix to β-sheet transition in proteins is highly important for understanding their folding and biological functions. It is recognized that the α→β transition is probably responsible for several conformational diseases, such as Alzheimer disease, where the α-helical forms are normal and the β-sheet forms are amyloidogenic. Urea is an accepted denaturating agent, which may act in several molecular mechanisms. These possible pathways include direct interactions of urea with the protein, indirect effects by decreasing water-water interactions and hydrogen bond strength, and allowing the exposure of nonpolar groups of the protein to the solvent and combinations thereof.

Figure 9A:
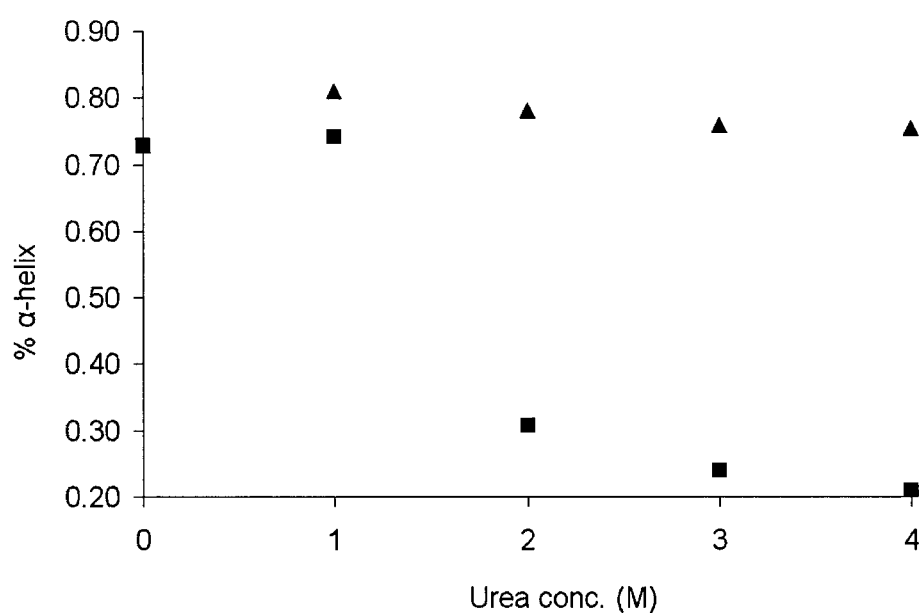
FIGS. 9a-c present (a) α-helix (b) random coil and (c) β-sheet content as a function of urea concentration (M) in the (▲) GMO/tricaprylin/LSZ/water system and (■) in lysozyme solution in $D_2O$.
Figure 9B:
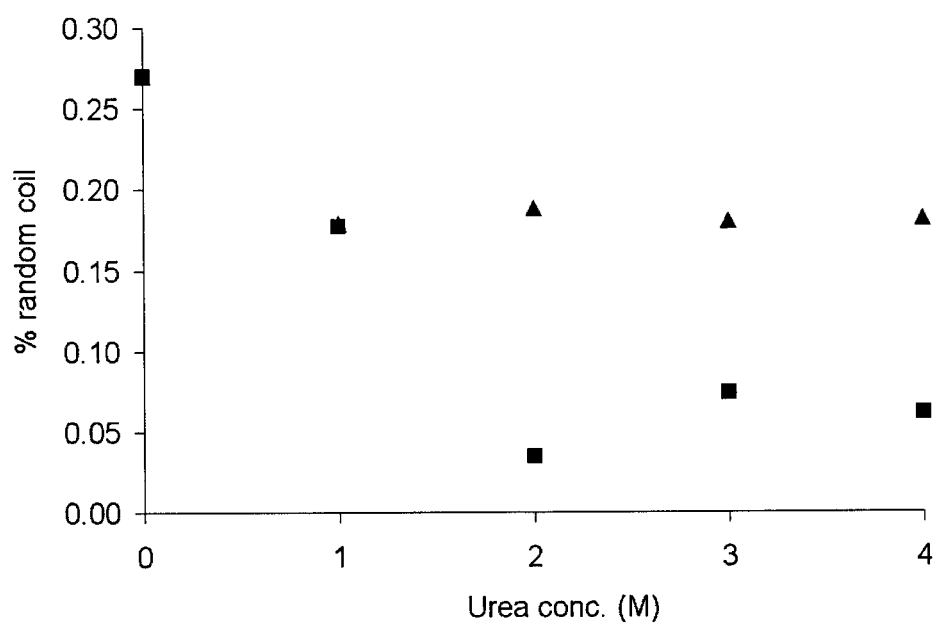
Figure 9C:
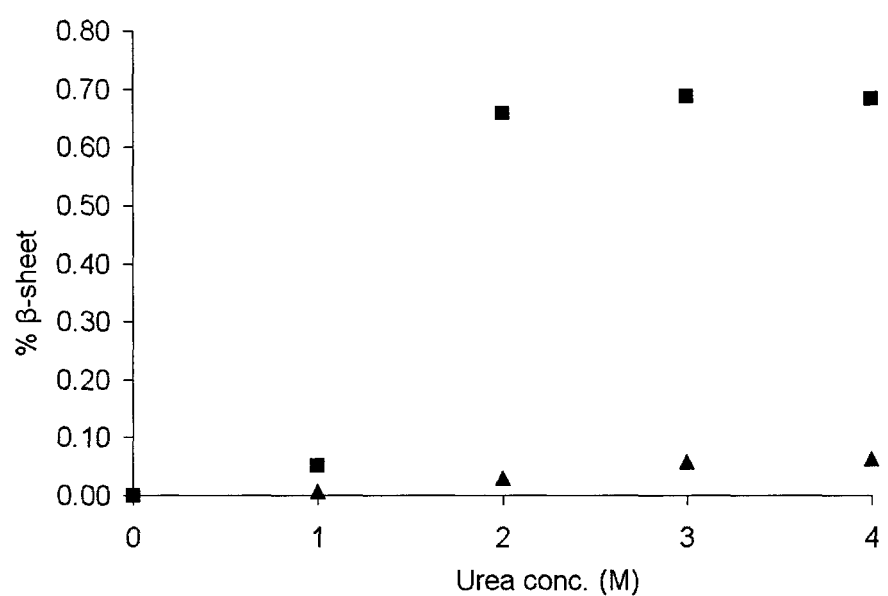

FIGS. 9a-c demonstrate the effect of urea on the LSZ structure. In a water solution, the α-helix and random coil content was drastically decreased from 0.73 to 0.21 and from 0.27 to 0.03, respectively (FIG. 9a and FIG. 9b) in favor to β-sheet formation up to 0.69 (FIG. 9c), starting from the concentration of 2M urea. The β-sheet formation was detected by FTIR analysis at 1620 cm$^{-1}$ and it was associated with aggregation of the protein, caused by denaturation, in accordance with the literature. In contrast, within the hexagonal mesophase the α-helical conformation stayed intact up to 4M of urea. The β-sheet content within the $H_{II}$ mesophase was significantly lower and the random coil content was higher as compared to the water solution (0.18 vs. 0.06).

This indicates considerably lower degree of denaturation of LSZ within the water cylinders. The hexagonal phases impeded the α→β transition in LSZ, thereby stabilizing the protein under denaturation conditions. It seems that the interactions between the protein and the hydroxyls of monoolein reduced the ability of urea to induce the denaturation of LSZ via direct interactions, preserving the helical structure. By analogy to the pH dependent behavior of LSZ, the hexagonal mesophase provides stabilizing environment for LSZ, preferring helical and random coil structures over β-sheet conformation.

5. Rheological Measurements

The aim of the rheological measurements was to establish a correlation between the molecular level and the mesoscopic organizations of the mesophase systems, if any. Frequency-dependent rheological measurements were performed to characterize the viscoelasticity of the $H_{II}$ phases. This was performed by determination of the storage modulus (G'(ω)), loss modulus (G"(ω)), the complex viscosity η* and the relaxation time ($τ_{max}$) upon addition of 0-3 wt % of LSZ. The storage moduli G'(ω) and the loss moduli G"(ω) were plotted against the frequency of the applied oscillations (ω).

Figure 10A:
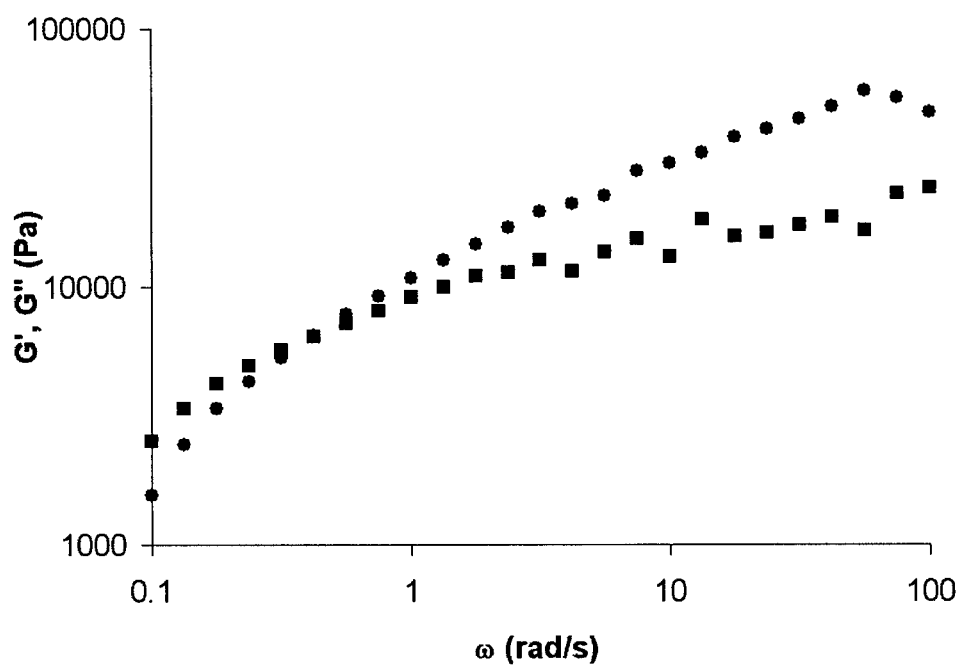
FIGS. 10a-d present (●) the storage modulus (G') and (■) the loss modulus (G") as a function of the applied oscillations frequency (ω), of the GMO/tricaprylin/LSZ/water systems containing weight ratio GMO/tricaprylin 9:1, 20 wt % water, (a) 0, (b) 1, (c) 2 and (d) 3 wt % lysozyme.

The behavior of the $H_{II}$ phase in the absence of additives is depicted in FIG. 10a. At low frequencies, the GMO/TAG/water system was found to be more viscous than elastic (G">G'). With an increase in angular frequency, both G' and G" increased monotonically, and finally, above the crossover point, the elastic properties of the systems dominated (G'>G"), indicating that the stored energy in the structure prevailed over the energy that was dissipated by the viscous forces. At frequencies close to the crossover point, the $H_{II}$ phases revealed viscoelastic behavior that could be classified as the "transition to the flow region".

Figure 10B:
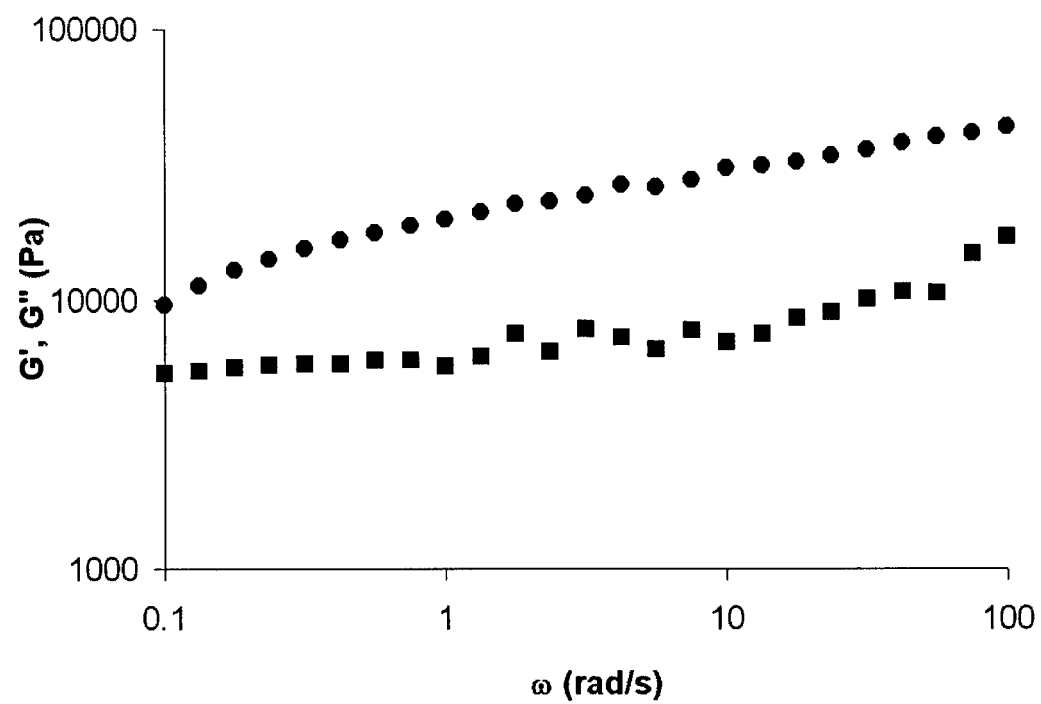
Figure 10C:
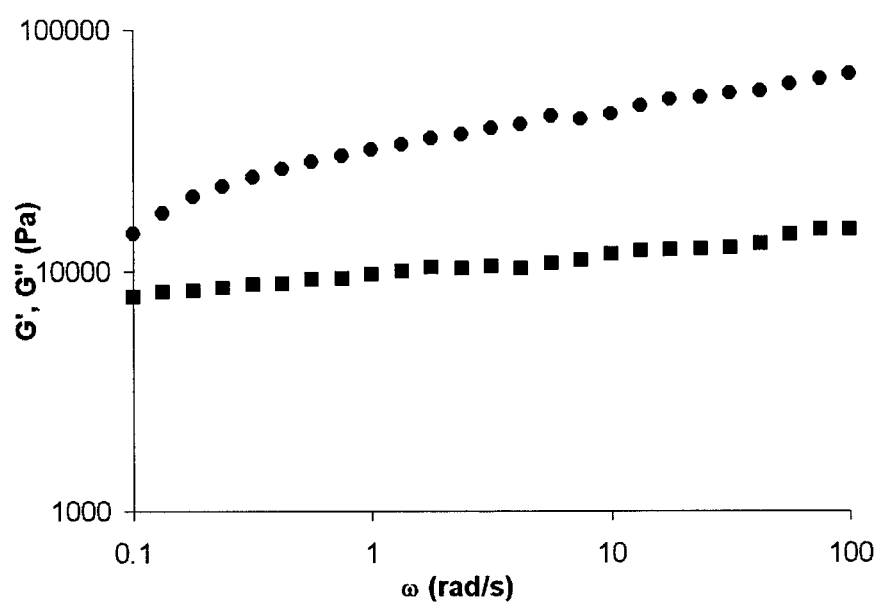
Figure 10D:
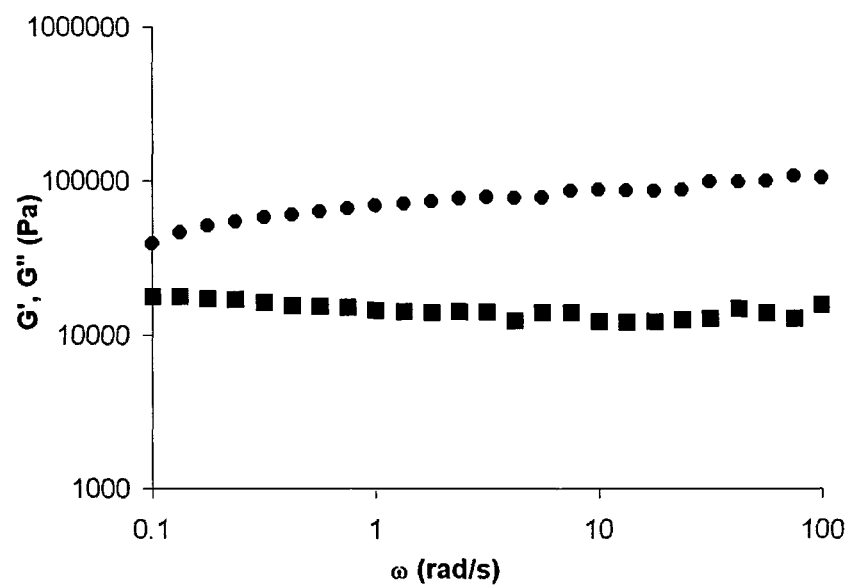

The viscoelastic behavior of the hexagonal structures was significantly modified in the presence of LSZ (FIGS. 10b-d). The most evident change was the disappearance of the crossover point between G' and G", which evidently occurred below the applied frequency window (ω<0.01 rad/s), indicating higher relaxation times and increased elasticity of the samples loaded with LSZ. In addition, in the unloaded system both G' and G" were strongly dependent on the applied frequency, suggesting a weak gel model behavior.

In contrast to the empty system, the moduli of the loaded systems exhibited less pronounced dependency on the oscillation frequency demonstrating a more moderate increase of the G' and G" as function of frequency upon increase in LSZ concentration. This suggests a more solid-like behavior and increased strength of the intermolecular interactions as a function of increased concentration of the protein. Therefore, it was expected that quantitative examination of the relaxation times and complex viscosities of the $H_{II}$ mesophases would reflect these trends. As was demonstrated earlier [6], the viscoelastic behavior of the $H_{II}$ phases complies with the Maxwell model only at low frequencies, where the plot G'/G" against ω is a straight line (data not shown), resulting in $\tau_{max}$ as the slope. At higher frequencies, the systems deviated from the Maxwell model, displaying a single relaxation time.

Figure 11:
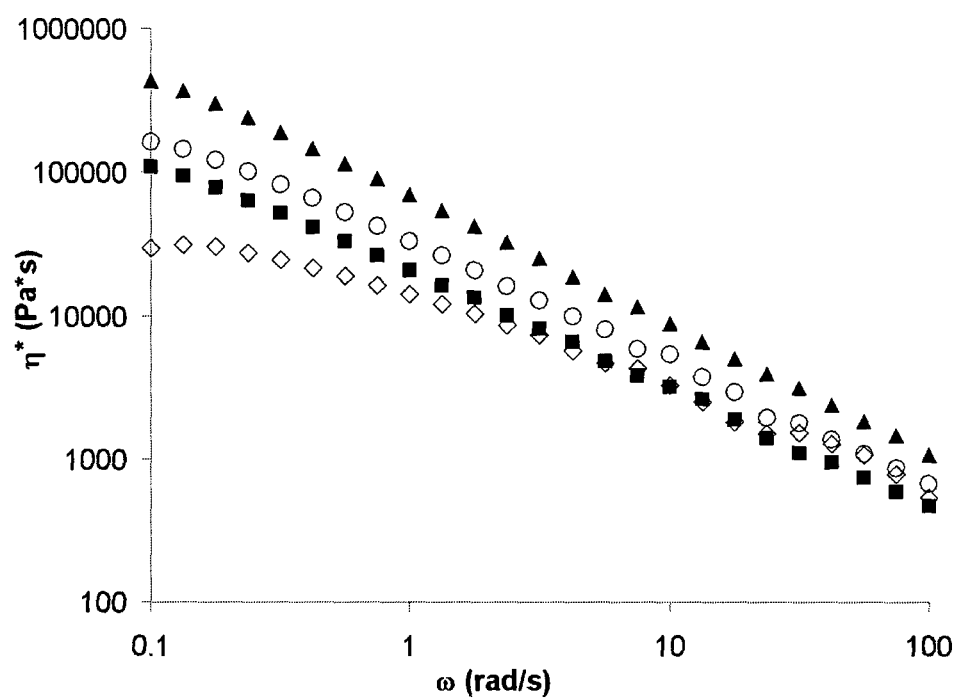
FIG. 11 present the complex viscosity η* as a function of the applied oscillations frequency (ω), of the GMO/tricaprylin/LSZ/water systems containing weight ratio GMO/tricaprylin 9:1, 20 wt % water, (◇) 0, (■) 1, (○) 2 and (▲) 3 wt % LSZ.

Linear increase of $\tau_{max}$ was observed with increasing concentrations of LSZ (Table 2). The embedding of even 1 wt % of LSZ increased $\tau_{max}$ by approximately 100%. The maximum relaxation time was finally increased by ~180% at the presence of 3 wt % LSZ. It is recognized that in liquid crystals $\tau_{max}$, which is the longest relaxation time, is regarded as the time scale for relaxation to the equilibrium configuration of the water-lipid interface, following perturbation by shear deformations. Hence, the linear increase in $\tau_{max}$ and therefore in the elasticity may be attributed to stronger hydrogen bonding in the water-surfactant interface, induced only due to the solubilization of the protein. This is in clear agreement with the ATR-FTIR results that revealed stronger hydrogen bonding between the hydroxyls of GMO and its environment on the molecular level, in the presence of LSZ. Since the major rheological properties of LLC depend primarily on the topology of the water-surfactant interface, the complex viscosity of the mesophases was also affected by the incorporation of LSZ. As shown in FIG. 11, the addition of LSZ caused a considerable increase in the complex viscosity η* of the structures. The frequency dependence of complex viscosity was analyzed in terms of the power law model (Eq. 3):

$$\eta^* = S\omega^m \quad \text{Eq. 3}$$

In Eq. 3, S is the gel strength parameter, which depends on the strength of intermolecular interactions and m is the complex viscosity relaxation exponent. Values of m close to zero indicate a liquid-like behavior, while values of m approaching −1 suggest a solid-like response of the system. The increase in the S values, as may be noted from Table 2, suggested an enhancement of the intermolecular interactions and increased m values (from −0.57 in the empty system to −0.87 at the presence of 3 wt % LSZ), indicating a more pronounced solid-like response of the systems as a result of LSZ solubilization. Thus, the major effects of the entrapment of LSZ on the macroscopic rheological properties of the systems are higher elasticity and increased solid-like response. This too may be attributed to the increased strength of hydrogen bonding of the hydroxyls of GMO with the protein in the interface and the stabilization of this region.

TABLE 2

Effect of LSZ concentration on $\tau_{max}$, S and m of the GMO/tricaprylin/LSZ/water systems containing weight ratio GMO/tricaprylin 9:1 and 20 wt % water.

| LSZ wt % | $\tau_{max}$ (sec) | S | m |
|---|---|---|---|
| 0 | 2.46 | 11303 | −0.574 |
| 1 | 4.70 | 19197 | −0.797 |
| 2 | 5.71 | 29959 | −0.806 |
| 3 | 7.27 | 64795 | −0.872 |

6. Temperature Effect 6.1 SAXS experiments—

Figure 12A:
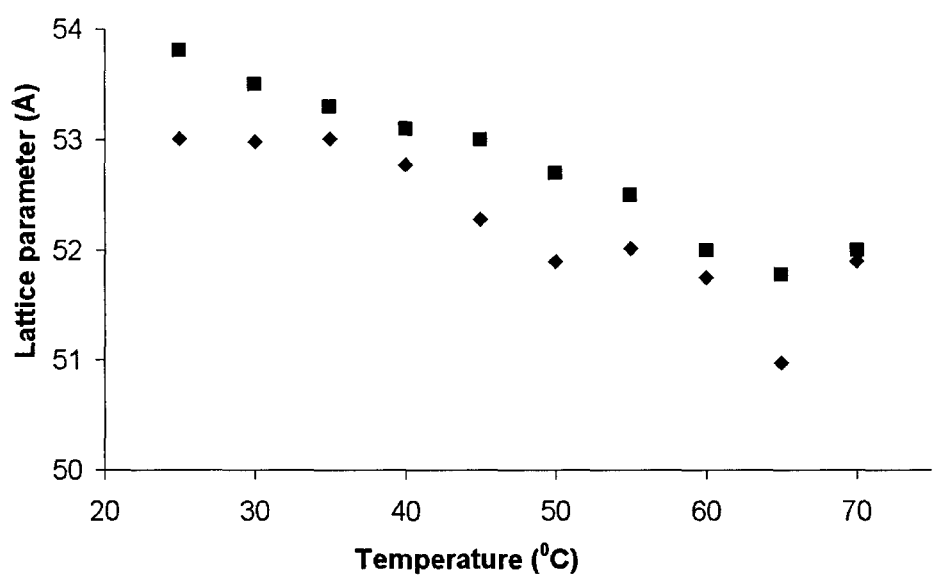
FIGS. 12a-b present (a) the lattice parameter (Å) and (b) domain size (Å) of 17 wt % water $H_{II}$ mesophases as a function of temperature as measured by SAXS, at (■) the empty and (◆) 2 wt % lysozyme loaded system.

SAXS measurements at a temperature range of 25-75° C. were performed to monitor the effect of LSZ solubilization on the lattice parameter of the hexagonal structures without additives and of 2 wt % LSZ loaded systems; both $H_{II}$ systems contained 17 wt % water (FIG. 12a).

Results indicate that the structure of each of the $H_{II}$ mesophases, with and without the protein, was destroyed at a temperature of 75° C. In addition, both the empty and LSZ loaded systems suggested a similar behavior. A decrease of 2 Å in the lattice parameter was monitored at both systems. The decrease in the lattice parameter with increasing temperature was an expected phenomena, being attributed either to dehydration of the surfactant polar headgroups or an increase in the hydrocarbon chain mobility. Further heating caused melting of the $H_{II}$ mesophase and formation of the micellar solution ($L_2$). It was recognized that the behavior of both the protein and the liquid crystalline phase was extremely temperature dependent and therefore, it was concluded that the interactions between LSZ and the hexagonal structures are deeply effected by temperature modulation.

Figure 12B:
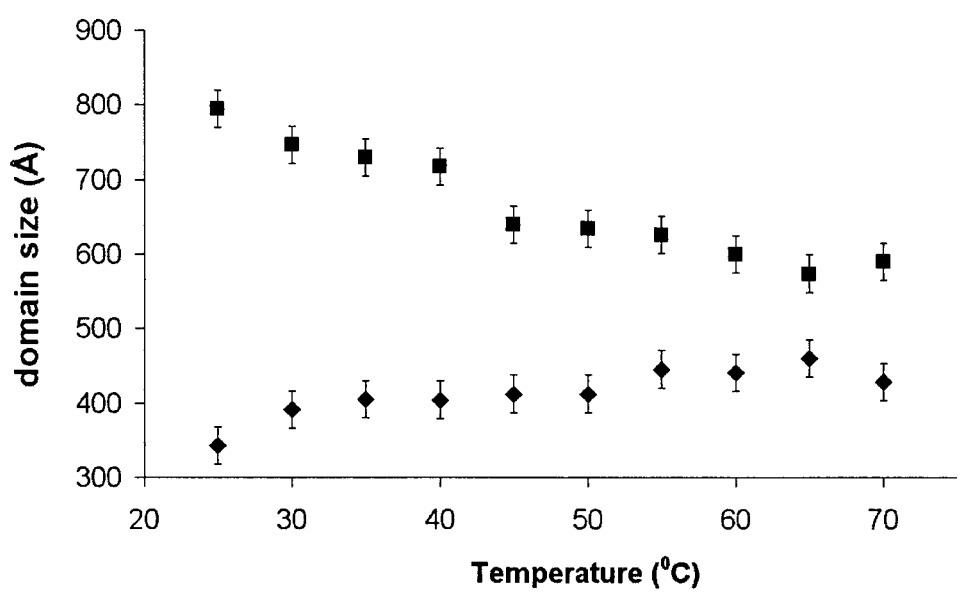

The domain size of the $H_{II}$ mesophases, which presents the degree of order (as determined by diffraction peak broadening), was also investigated. Upon temperature increase, a decrease in the domain size ($L_H$) of ~25% (from 800 to 470 Å) was detected in the empty hexagonal structure (FIG. 12b). Low-water content hexagonal samples are less ordered at a higher temperature than at room temperature, having smaller effective crystallite size (lower $L_H$ values) and partially dehydrated head groups.

Though, the domain size of the $H_{II}$ mesophase in the absence of additives decreased as a function of temperature, an opposite trend was detected when LSZ was present. The domain size of the $H_{II}$ mesophases containing LSZ increased from 340 to 460 Å with the temperature increase. This observation may be expected if two competing processes took place upon temperature increase. In addition to the described process, which is responsible for the decrease of the $L_H$ values in the empty system, the second competing process is related to the LSZ and GMO temperature-dependent interactions. At higher temperatures, weakening of the monoglyceride hydroxyls interactions with the protein is expected. As a result, part of the GMO-protein bonds are weakened and/or cleaved, leading to the reconstitution of the initially low domains size.

6.2 Rheological Measurements—

Figure 13A:
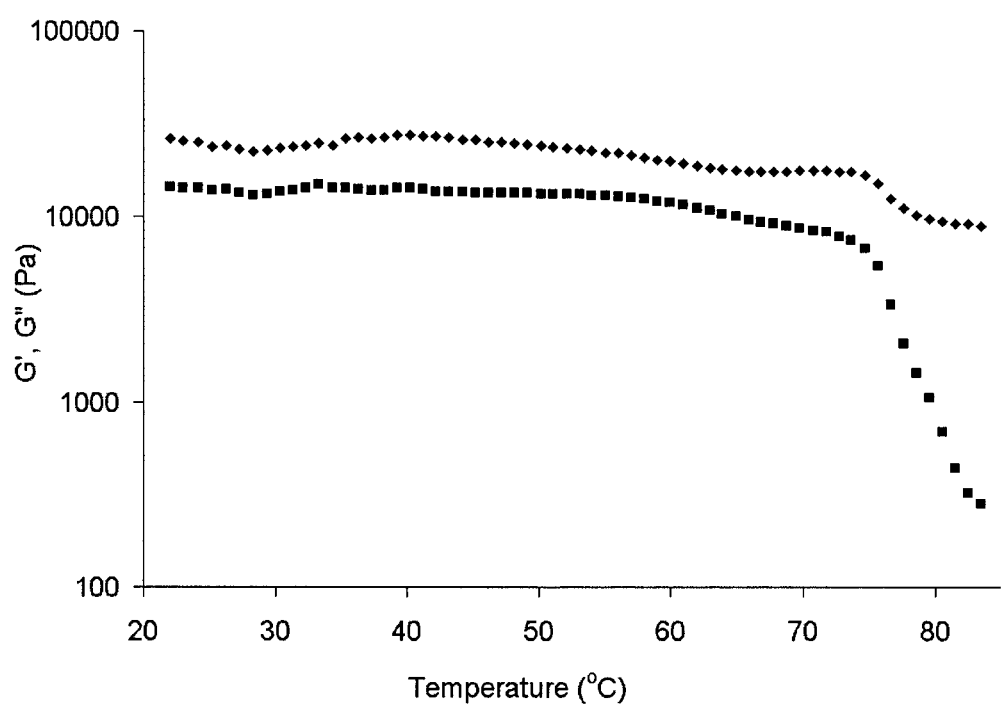
FIGS. 13a-d present (◆) the storage modulus (G') and (■) the loss modulus (G") as a function of temperature, of the GMO/tricaprylin/LSZ/water systems containing weight ratio GMO/tricaprylin 9:1, 20 wt % water, (a) 0, (b) 1, (c) 2 and (d) 3 wt % lysozyme.
Figure 13B:
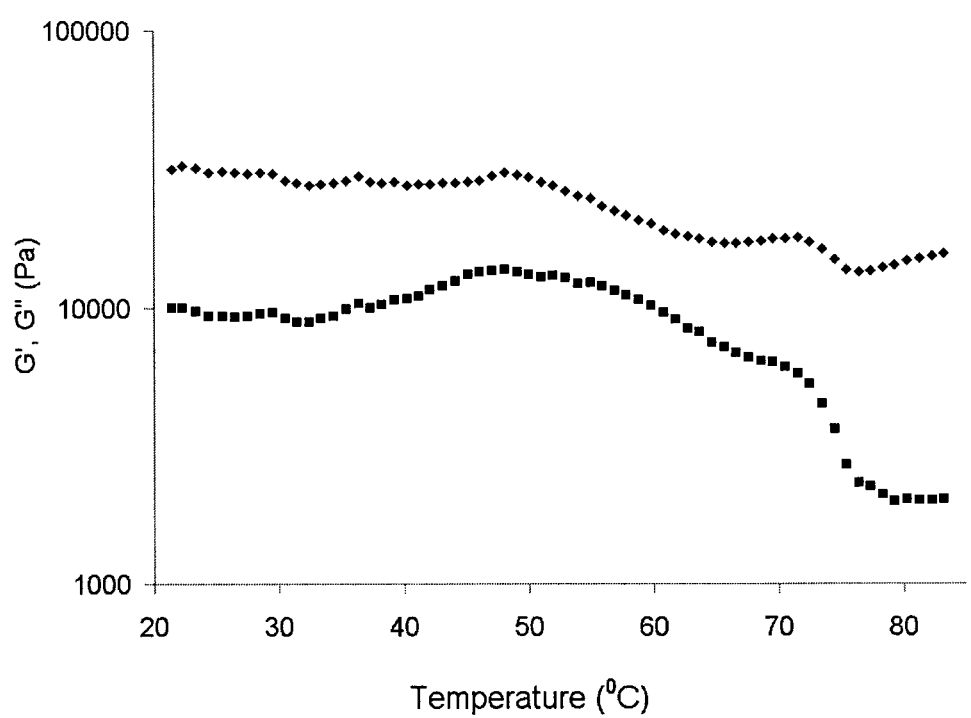
Figure 13C:
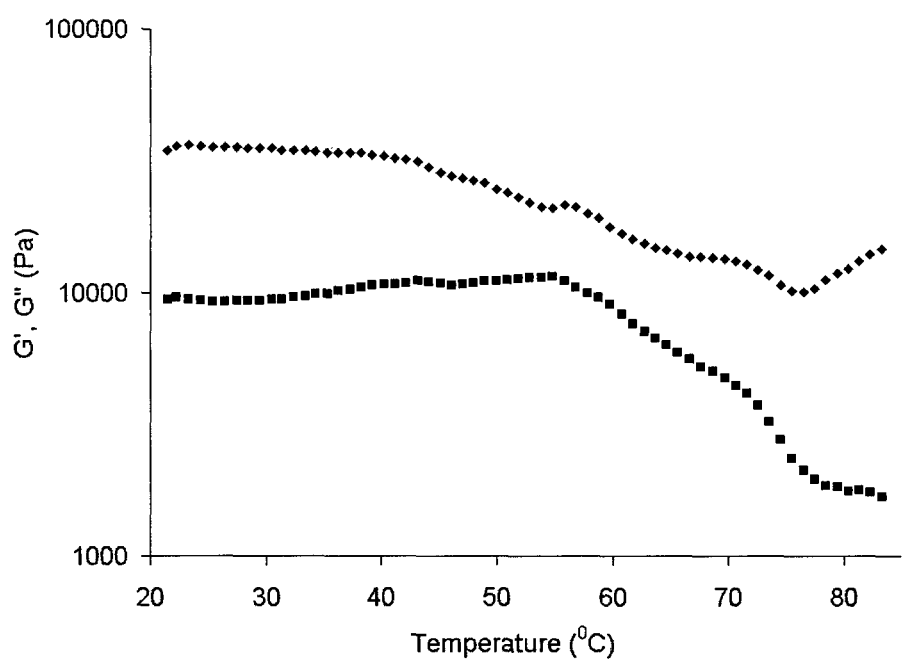
Figure 13D:
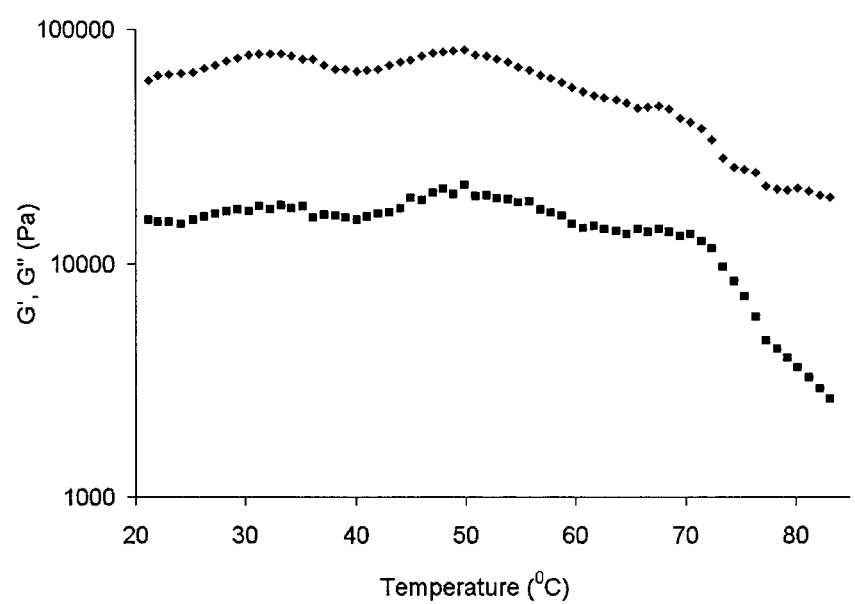

The thermal structural changes occurring in the LSZ loaded and empty $H_{II}$ mesophases were studied by a rheological temperature-sweep experiment. Temperature-dependent rheological measurements were performed at a constant oscillation frequency of 3 rad/sec in which all samples were already after their crossover point, at a region were the elastic properties of the systems dominate (G'>G"). This was achieved by determination of the storage modulus (G'), loss modulus (G") and the tan δ upon addition of 0-3 wt % of LSZ. Both the storage moduli G' and the loss moduli G" were plotted as a function of the temperature, as shown in FIGS. 13a-d. The behavior of the $H_{II}$ phase in the absence of additives is depicted in FIG. 13a, showing that the loss moduli G" and the storage moduli G' remained almost constant at the temperature range of 20-75° C. However, above 75° C. a significant decrease of both the loss moduli G" and the storage moduli G' occurred due to the destruction of the $H_{II}$ mesophases structures.

Figure 14:
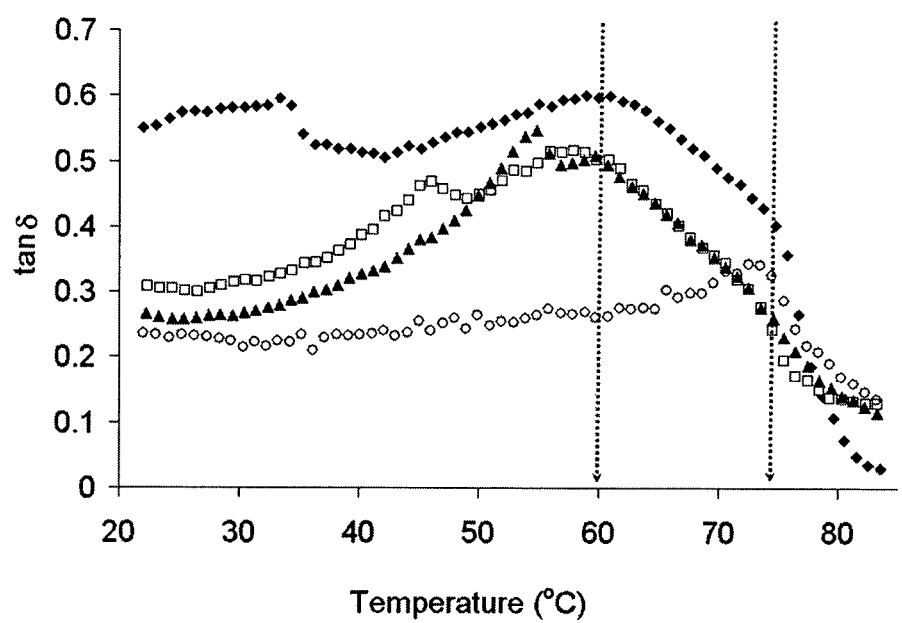
FIG. 14 presents the tan δ parameter (G"/G') as a function of temperature, of the GMO/tricaprylin/LSZ/water systems containing weight ratio GMO/tricaprylin 9:1, 20 wt % water, (◆) 0, (□) 1, (▲) 2 and (○) 3 wt % lysozyme.

Tan δ (G"/G') was calculated presenting a value of 0.5-0.6 at the range of 20-60° C. (FIG. 14). The minor deviations at that region were attributed to the structural rearrangements of the randomly oriented macroscopic domains of the hexagonal liquid crystals, resulting in more oriented structures. At the temperature range of 60-75° C., tan δ decreased from 0.6 to 0.4 with a temperature increase. This decrease of tan δ resulted from the enhanced flow ability of the liquid crystalline structure, induced by the additional temperature increase. The further temperature increase caused melting of the $H_{II}$ mesophase and formation of the micellar solution, as was shown by the SAXS measurements. The onset of this structural transition ($H_{II}$-$L_2$), which is an order-disorder transition (ODT) of the systems, was clearly detected at ca. 75° C. at the rheological thermograph, as was reflected by a drastic drop of the mechanical moduli (especially G") and tan δ.

The viscoelastic behavior of 1, 2 and 3 wt % LSZ loaded hexagonal mesophases was also studied (FIGS. 13b-d), revealing a different trend. While the storage moduli (G') of empty $H_{II}$ mesophase remained almost constant at the temperature range of 20-75° C., the storage moduli (G') of the LSZ solubilized hexagonal systems remained nearly unchanged at the temperature range of 20-50° C., but a significant decrease was detected when the temperature was raised from 50° C. to 75° C. This significant decrease in the elasticity of the sample implies on the dehydration of the GMO headgroups. As was inferred from the ATR-FTIR results, that LSZ interacts with O—H groups of GMO in the outer interface region, decreasing the packing order of the hydroxyls, implying a stronger hydrogen bonding between the surfactant and its environment, which includes $D_2O$ and LSZ. This may suggest that the temperature increase causes a gradual cleavage and/or weakening of the hydrogen bonding between the surfactant and its environment.

Furthermore, examination of the calculated tan δ gives an insight into the modification of the rheological behavior of the systems (FIG. 14). The parameter tan δ increased from 0.31 and 0.27 at the 1 and 2 wt % LSZ loaded system, respectively, at 20° C. and to 0.51 at 60° C. This increase of tan δ supports the gradual dehydration of the surfactant headgroups. At a temperature above 60° C., similarly to the empty $H_{II}$ mesophases systems, tan δ decreased with any temperature increase. The tan δ decrease implied on the enhanced flow ability of the liquid crystalline structure induced by the additional temperature increase, followed by melting of the $H_{II}$ mesophase and formation of the micellar solution at high temperatures. In contrast to the $H_{II}$ mesophases containing 1-2 wt % LSZ, the 3 wt % LSZ loaded $H_{II}$ mesophase showed a different behavior. At the 3 wt % LSZ load, tan δ slightly increased from 0.24 at 20° C. to 0.34 at 75° C. The minor increase of tan δ may be attributed to the limited dehydration of the surfactant headgroups. At the 3 wt % LSZ load, the interface was saturated, therefore the dehydration process was less significant. In other words, the increase of the temperature resulted in a minor cleavage and/or weakening of the hydrogen bonding between the O—H groups of GMO surfactant and its environment. Above 75° C. the melting of the $H_{II}$ mesophases and the formation of the micellar solution led to a decrease of the tan δ parameter.

6.3 ATR-FTIR Analysis—

Proteins in general are known for their low stability at high temperatures. The stability of LSZ was examined within the hexagonal carrier and compared to its aqua solution. The mutual influence of the LSZ on the structure of the GMO/tricaprylin/LSZ/$D_2O$ mesophases was elucidated using $D_2O$ instead of $H_2O$ to avoid the influence of water OH bending on the amide I' band of LSZ.

Slight increase of 2.5 Å in the lattice parameter was noted when $D_2O$ was used, compared to the $H_2O$ based samples, an observation which may be attributed to the more tight bonding of $D_2O$ with the surfactants hydrophilic moieties (data not shown).

The absorption of the amide I' band of LSZ at room temperature in both $D_2O$ and the hexagonal carrier was at 1650 cm$^{-1}$. However, by increasing the temperature a different trend was detected: while the hexagonal mesophase showed a slight increase in wave number at higher temperatures, the water solution showed a significant decrease in the wave number (FIG. 15a).

Figure 15A:
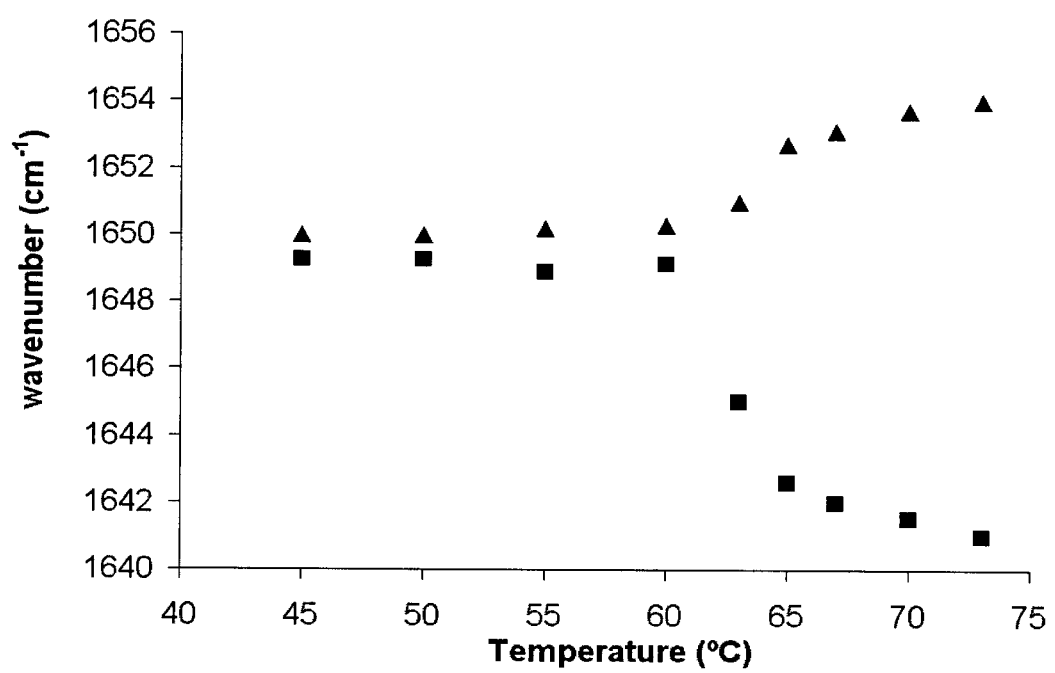
FIGS. 15a-c present (a) the amide I' frequency ($cm^{-1}$), (b) α-helix and (c) random coil content as a function of temperature in the (▲) GMO/tricaprylin/LSZ/water system and (■) in lysozyme solution in $D_2O$.
Figure 15B:
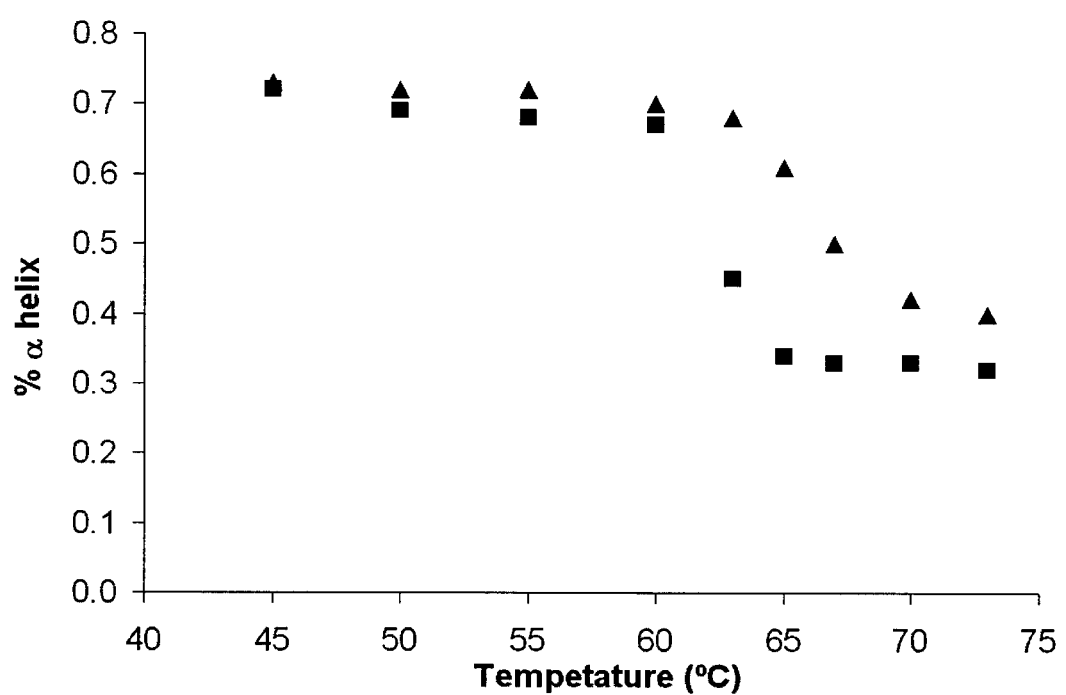
Figure 15C:
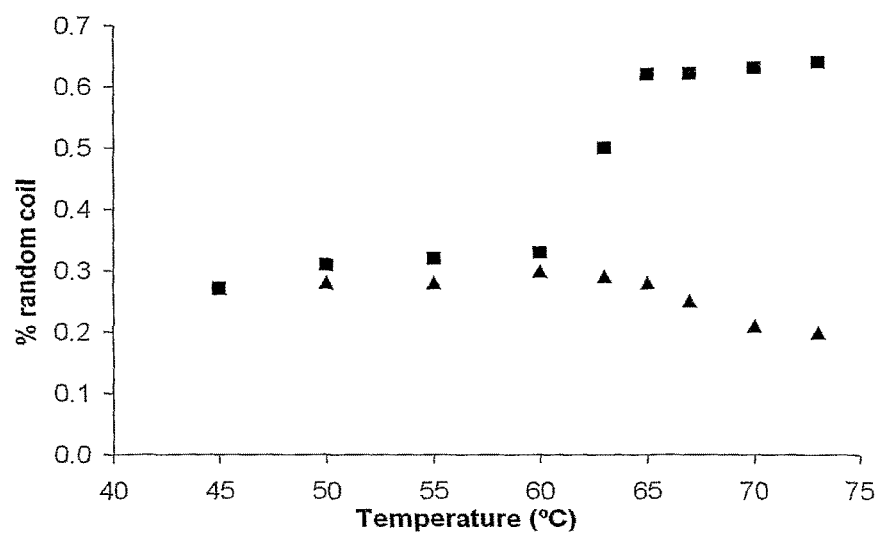

Resolution of the amide I' band of LSZ by the second derivative analysis demonstrated that at the temperature range of 25-60° C., both the α-helix and the random coil contents of both the $H_{II}$ mesophase carrier and $D_2O$ solutions did not change (FIGS. 15a-b). In $D_2O$, from 63° C., a further temperature increase led to LSZ denaturation, which was presented by a drastic decrease of the α-helix content (from ~0.7 at 60° C. to 0.34 at 65° C.) and a multiplication of the random coil content (from ~0.3 at 60° C. to 0.62 at 65° C.). However, between 63-65° C., the LSZ loaded $H_{II}$ mesophase preserved its random coil content and exhibited only a minor decrease in its α-helix content (from ~0.7 at 60° C. to 0.61 at 65° C.) in favor of γ-turn formation (from 0 to 0.1). Further temperature increase confirmed the diverse denaturation mechanism. Up to 73° C., the α-helix and the random coil contents decreased in favor of γ-turn formation.

The LSZ hydrogen bonding with hydroxyls of GMO, showed by the spectroscopic measurements, may be mostly assigned to interactions of the α-helix with the O—H groups of the surfactant. In other words, these interactions stabilize the helical structure of LSZ at higher temperatures as compared to the water solution. These results indicate that the solubilization of a protein such as LSZ into the hexagonal carriers enables its use in enzymatic activity also at higher temperatures where it possesses increased conformational stability, as compared to the water solution.

C. GMO/Lipophilic/Water Mesophases

1. GMO/lipophilic antioxidant/water Mesophase Solubilizing Hydrophilic Antioxidant: GMO/Vitamin E/Water Solubilizing Vitamin C Ascorbic acid, usually known as vitamin C (AA), is an essential nutraceutical commonly used in medicine, food, cosmetics, material preservation and biochemistry. It efficiently protects important organic and biological molecules from oxidative degradation by its property of strong hydrophilicity.

α-Tocopherol, commonly known as vitamin E (VE), acts as a very efficient radical-chain-breaking antioxidant in tissues. Due to its Van der Waals interactions with membrane phospholipids, VE can be used also as membrane-stabilizing agents.

A system for delivery of synergistic nutraceuticals, e.g., antioxidants, where one antioxidant has an aqueous phase mode of action and the other has a lipid phase mode of action was constructed. In such a system, a lipophilic antioxidant such as α-tocopherol (VE) replaced the tricaprylin of the above-discussed mesophases, forming a GMO/α-tocopherol/water mesophase (90/10 wt % ratio and 12.5 wt % water or 78.75%/8.75%/12.5% of GMO/α-tocopherol/water, respectively) with a hydrophilic antioxidant such as ascorbic acid (AA) being solubilized therein.

1.1. Sample Preparation

Distilled glycerol monooleate consisting of 97.1 wt % monoglyceride and 2.5 wt % diglyceride (acid value 1.2, iodine value 68.0, melting point 37.5° C.), and free glycerol 0.4%) were purchased from Riken (Tokyo, Japan).

D-α-tocopherol, Vitamin E 5-96 (containing 1430 IU of vitamin E) was received from ADM Company (Decatur, Ill.).

L-(+)-ascorbic acid was purchased from Baker Chemical Co. (Phillipsburg, N.J.).

Water was double distilled.

All ingredients were used without further purification.

The GMO/α-tocopherol/water hexagonal liquid crystalline samples containing various quantities (1-6 wt %) of ascorbic acid were formed by mixing all the components (GMO and α-tocopherol in 9:1 weight ratio), while heating to ~70° C. in sealed tubes under nitrogen (to avoid oxidation of the GMO) for ca. 15 min. The samples were stirred and cooled to 25° C. As a result of AA solubilization the concentrations of GMO and α-tocopherol were decreased, keeping the weight ratio of GMO to α-tocopherol at 9:1, respectively, and water content constant. $D_2O$ was used for FTIR measurements instead of water.

The impact of ascorbic acid (AA) guest molecules on the macrostructure of the reverse hexagonal mesophases formed by the mixture of GMO/vitamin E/water while GMO/VE weight ratio was 90/10, with 12.5 wt % water was examined. Up to 6 wt % of AA were solubilized in this $H_{II}$ system. Each sample containing both VE and AA with variable amounts was identified by a light microscope equipped with crossed polarizers and mounted with a video camera and a monitor. The samples were analyzed at room temperature.

Figures 16A, 16B, 16C:
FIGS. 16a-c present polarized light microscope images of the 0, 3 and 6 wt % AA loadings in GMO/VE/water system, representing (a) the empty system, (b) a moderate and (c) a maximal solubilization capacity.

Polarized light microscope images of the 0, 3 and 6 wt % AA loadings in GMO/VE/water system are shown in FIGS. 16a-c, representing the empty system, a moderate and a maximal solubilization capacity. All three images, in the absence and presence of AA, displayed birefringent colorful textures attributed to the hexagonal symmetry. It should be noted that both images representing the loaded $H_{II}$ systems, exhibited clear texture, implying that the hexagonal phase enabled the AA accommodation without any precipitation.

For the following DSC measurements, a Mettler Toledo DSC822 measuring model system was used. The DSC measurements were carried out as follows: 5-15 mg hexagonal liquid crystalline samples were weighed, using a Mettler M3 microbalance, in standard 40 μL aluminum pans and immediately sealed by a press. The samples were rapidly cooled in liquid nitrogen from +30 to −40° C., at a rate of 10° C. min$^{-1}$. The samples remained at this temperature for 30 min and then were heated at 1° C. per minute to 40° C. An empty pan was used as a reference. The instrument determined the fusion temperatures of the components and the total heat transferred in any of the observed thermal processes. The enthalpy change associated with each thermal transition was obtained by integrating the area of the relevant DSC peak. DSC temperatures reported here were reproducible to ±0.2° C.

In the absence of AA, during the heating scan from −40 to +40° C. of the mesophase GMO/VE/water, two endothermic peaks were observed (thermograph) with maxima at −2.1±0.2 (peak A) and 11.9±0.2° C. (peak B). As was previously affirmed (data not shown), peak A was associated to the melting of ice and peak B was attributed to the fusion of the hydrophobic moieties of the GMO solvated by VE. When comparing the two systems containing VE or tricaprylin as the oil phase, one could notice that the water melting temperatures are equivalent; however, the hydrophobic tails fusion peaks are different and are determined by the degree of hydrophobic interactions between the GMO and the oil, as dependent on the oil type. When tricaprylin (TC) was present, the melting peak appeared at a lower temperature, 5.9±0.2° C., but once VE molecules replaced the tricaprylin, the melting of the hydrophobic moieties of the GMO occurred at a higher temperature, 11.9±0.2° C. (peak B). This result may manifest the solvation level of GMO by the oil, implying that tricaprylin is more efficiently solvating the GMO tails, thereby inducing the formation of $H_{II}$ phase at lower temperatures than if VE serves as the oil phase. On the other hand, where the mesophase system was used as a reservoir vehicle for solubilization, higher solubilization levels of ascorbic acid, and also amphiphilic and hydrophobic guest molecules were obtained by this system, as compared to the one containing tricaprylin. These findings may be attributed to the ability of the molecule to incorporate itself into a limited volume of a given structure. Based on the spatial structure of the molecule, it is reasonable to surmise that the tricaprylin would easily accommodate between the GMO tails, while the VE accommodation is considered to be more difficult.

Figure 17:
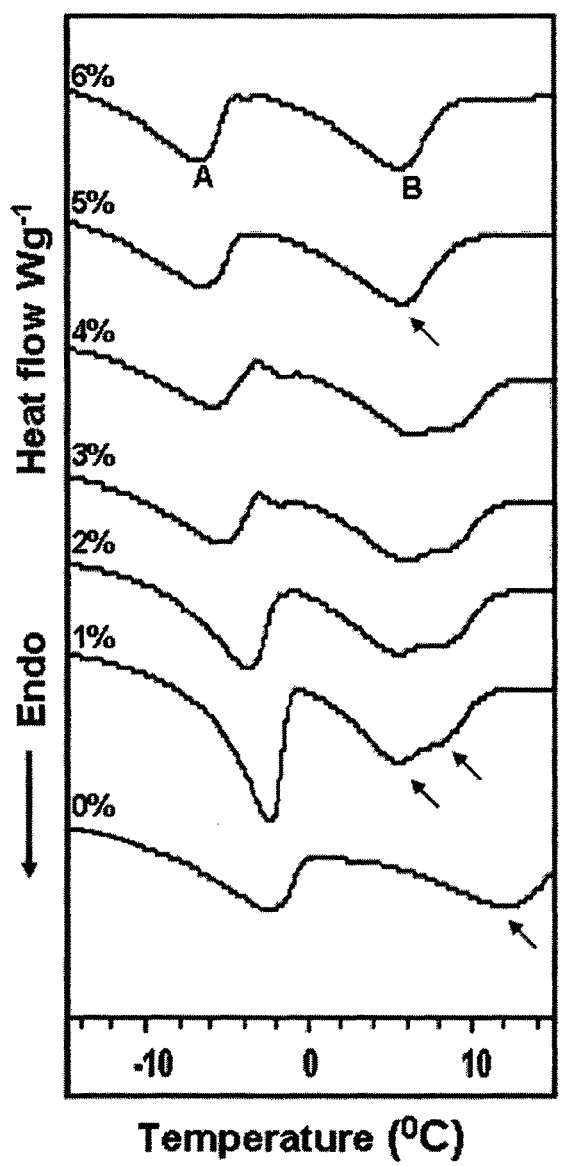
FIG. 17 represents the DSC thermographs obtained during the heating scan from −40 to +40° C. of the mesophase GMO/VE/water, solubilizing between 0 and 6% AA.

The DSC outcome demonstrates that the incorporation of AA molecules composed of five hydrogen-bond acceptor sites (four hydroxyl+one ester group) had a significant effect on the thermal process of the mesophases, on both endothermic event reflected in peaks A and B, as shown in FIG. 17 and Table 3. As expected, an increase in content of molecules capable of binding water, such as AA, gradually decreased the water thawing temperature, from −2.5 down to −6.8±0.2° C. in the presence of 1-6 wt % AA (Table 3).

TABLE 3

Melting temperatures (° C.) of the $H_{II}$ systems (GMO/vitaminE/water), empty and loaded with 1-6 wt % of AA.

| AA (% wt) | Water Peak A (° C.) | Tails Peak B (° C.) | |
|---|---|---|---|
| 0 | −2.1 | 11.9 | |
| 1 | −2.5 | 8.3 | 4.8 |
| 2 | −3.8 | 8.6 | 4.9 |
| 3 | −5.5 | 8.7 | 5.5 |
| 4 | −6.0 | 9.2 | 5.9 |
| 5 | −6.5 | | 5.6 |
| 6 | −6.8 | | 5.4 |

Unpredictably, embedment of 1-4 wt % AA has additionally a significant effect on the lipidic tails fusion temperatures. The addition of even 1 wt % of AA decreased the melting temperature of the GMO lipophilic moieties and divided the peak into two subpeaks with maxima at 8.3 and 4.8±0.2° C. Further incorporation of AA up to 4 wt %, while did not affect the peaks temperature, led to a gradual decrease in the higher temperature peak area (with a corresponding increase in the lower temperature peak region) up to its complete disappearance, once 5 wt % AA was added. In the presence of 5-6 wt % AA, a single peak was observed at ~5.4±0.2° C.

These findings reveal additional hydrogen bonding in the water molecules upon incorporation of AA, suggesting the induction of a competition for water binding with the GMO polar headgroups. The water behavior may also be affected indirectly by the presence of AA guest molecules, resulting in reorganization and formation of additional hydrogen bonds in the $H_{II}$ structure.

The split in the lipophilic melting peak together with its appearance at a lower temperature, upon entrapping of AA molecules in the polar region, implies the presence of a looser lipophilic assembly with two populations. This can be achieved indirectly by swelling the GMO polar head thereby enabling additional penetration of VE and therefore more solvation of the GMO by VE molecules. It appears that above a critical AA concentration, >4 wt %, all VE molecules sufficiently accommodate between the GMO tails, thus the degree of solvation is higher and a single melting peak with relatively low temperature is obtained. Moreover, the overall hydrophobic contribution which determines the fusion temperature of the GMO tails, due to the combined AA with VE at these concentrations (4-5 and 8.8 wt %, respectively), is equal to the contribution of the tricaprylin alone at the same content of VE.

Figure 18:
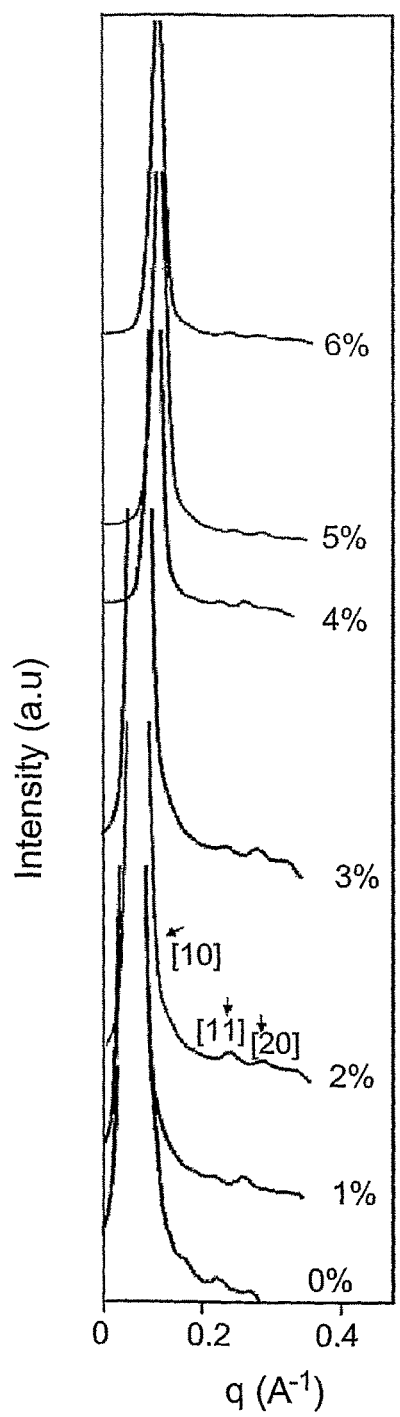
FIG. 18 provides the SAXS patterns of the empty GMO/VE/water mixture and AA-loaded mixtures at 25° C.

Small angle X-ray scattering (SAXS) was used to identify and characterize the structure of the phases. The SAXS patterns of the empty GMO/VE/water mixture and AA-loaded mixtures at 25° C. are shown in FIG. 18. For each mixture three peaks were observed, which were indexed as the (10), (11), and (20) reflections of a 2D $H_{II}$ phase, being in line with the microscope images in presented in FIGS. 16a-c.

From the three peak positions, the corresponding mean lattice parameters (a) of the hexagonal structures have been calculated and are summarized in Table 4. These results reveal an increase in the lattice parameter of the $H_{II}$ phases. Two stages of structural effect (i.e., cylinder swelling) may be detected in the systems where AA molecules are gradually incorporated. Upon addition of 1-3 wt % AA, the lattice parameter increases by ~3 Å and further incorporation of 4-6 wt % AA, resulting in an additional increase in the a-values (by 2 Å). It should be noted that in the GMO/VE/water system, once 3 wt % of AA were added the lattice parameter was increased by 4 Å and further increase in the solubilization loads did not further alter the a-values.

TABLE 4

Lattice parameters (a) of the $H_{II}$ systems, empty and loaded with different amounts of wt % of AA. The measurements were carried out at 25° C.

| AA (wt %) | Lattice Parameter (a) |
| --- | --- |
| 0 | 48.0 |
| 1 | 50.0 |
| 2 | 50.6 |
| 3 | 51.0 |
| 4 | 52.4 |
| 5 | 52.7 |
| 6 | 53.0 |

Considering the DSC results discussed above, a conclusion may be drawn that AA increases the hydration level of the headgroups, thereby swelling the cylinders and increasing the lattice parameter. The two-step swelling profile, clearly noted in Table 4, is in line with the DSC results. It may be suggested that: 1) AA is accommodated in the polar region in two main positions within two stages, and/or; 2) two steps of VE penetration upon incorporation of AA which is in agreement with the split of the peak that is associated with the GMO hydrophobic moieties melting and its conversion into a lower temperature.

When comparing the two $H_{II}$ systems, on the basis of either tricaprylin or VE, it can be surmised that in the case of lower AA-values, <3 wt %, the AA chaotropic effect is less pronounced when VE is present, due to its poor penetration into the GMO/water interface, compared to tricaprylin. However, at a higher concentration the interplay between AA and VE accommodation enables additional solubilization of AA.

Figure 19:
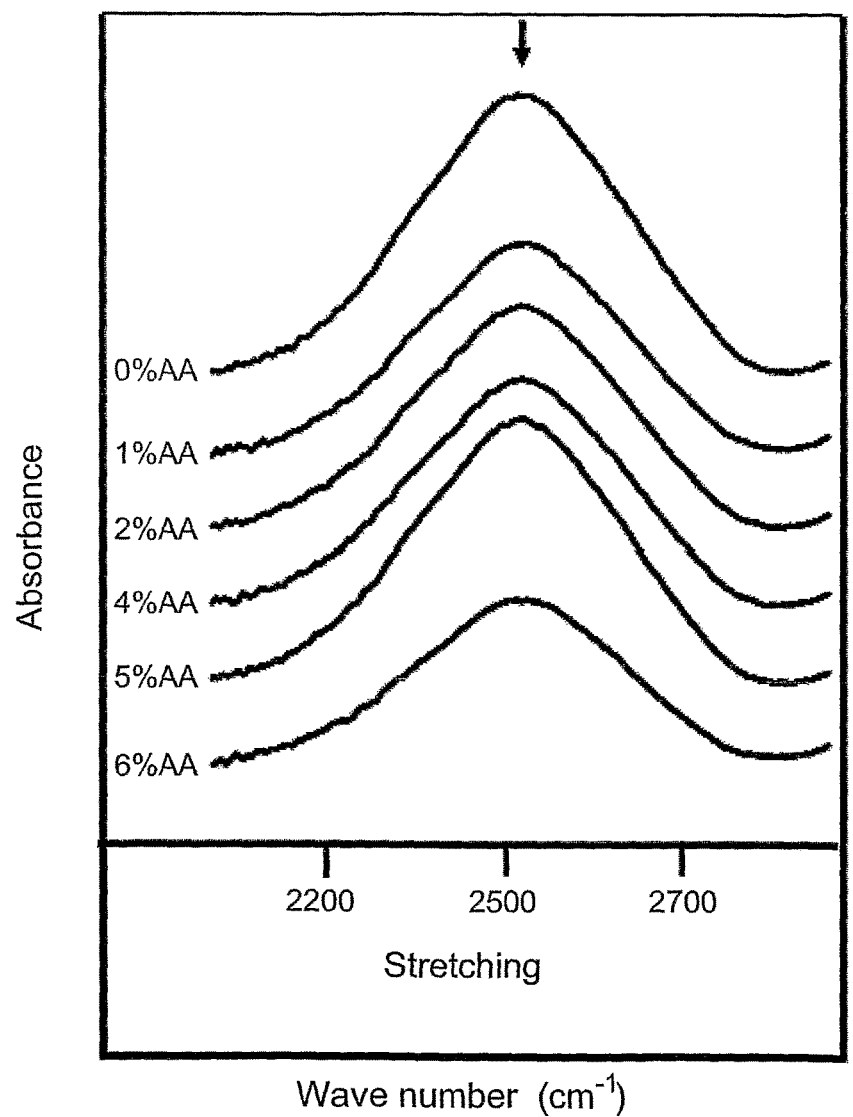
FIG. 19 presents the ATR-FTIR analysis of the interactions of the AA molecules with the water, GMO and VE, and their conformation with the $H_{II}$ structure, employing OH stretching vibrations.
Figure 20:
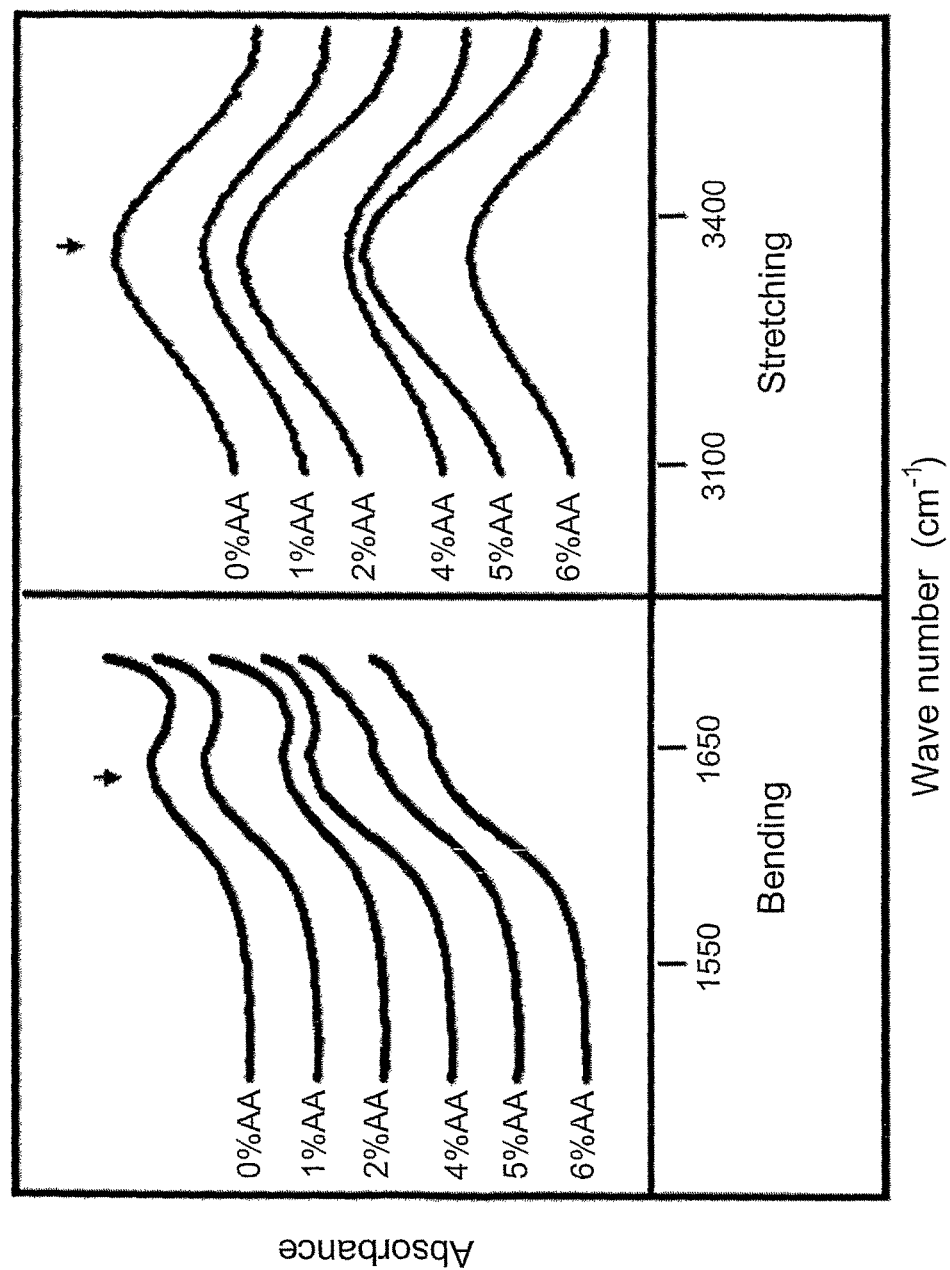
FIG. 20 presents the ATR-FTIR analysis of the H—O—H bending and stretching of the OH of the water with the GMO headgroups and the AA.

ATR-FTIR was used to elucidate the interactions of ascorbic acid with the $H_{II}$ structure and components and to spot its location within its gradual incorporation. For detailed analysis of the interactions of the AA molecules with the water, GMO and VE, and their conformation with the $H_{II}$ structure, four major bands of the FTIR spectrum were analyzed. Additionally, to improve the separation between the GMO polar region vibrations and the water, e.g., OH stretching vibrations, $H_2O$ was substituted as above by $D_2O$ (FIG. 19). The $H_{II}$ structure was divided into three different regions: an inner water region, a water/GMO interface and a GMO hydrophobic region (including VE). Correspondingly, the spectrum was investigated in terms of the water interactions with the GMO polar region or with the AA. The H—O—H bending band at ~1650 $cm^{-1}$ was used to characterize the competitive interactions of the OH of the water with the GMO headgroups and the AA (FIG. 20). It is known that the water bending vibration frequency increases when polar moieties (of either the GMO or the AA) compete for the hydrogen bonding. Substituting $H_2O$ by $D_2O$ enabled following the O-D stretching vibrations at ~2500 $cm^{-1}$ of the deuterated water, separately from the GMO O—H stretching vibrations. The stronger the hydrogen bonding between the surfactant or AA guest molecule and the water, the lower the stretching frequency of the O-D.

Figure 21A:
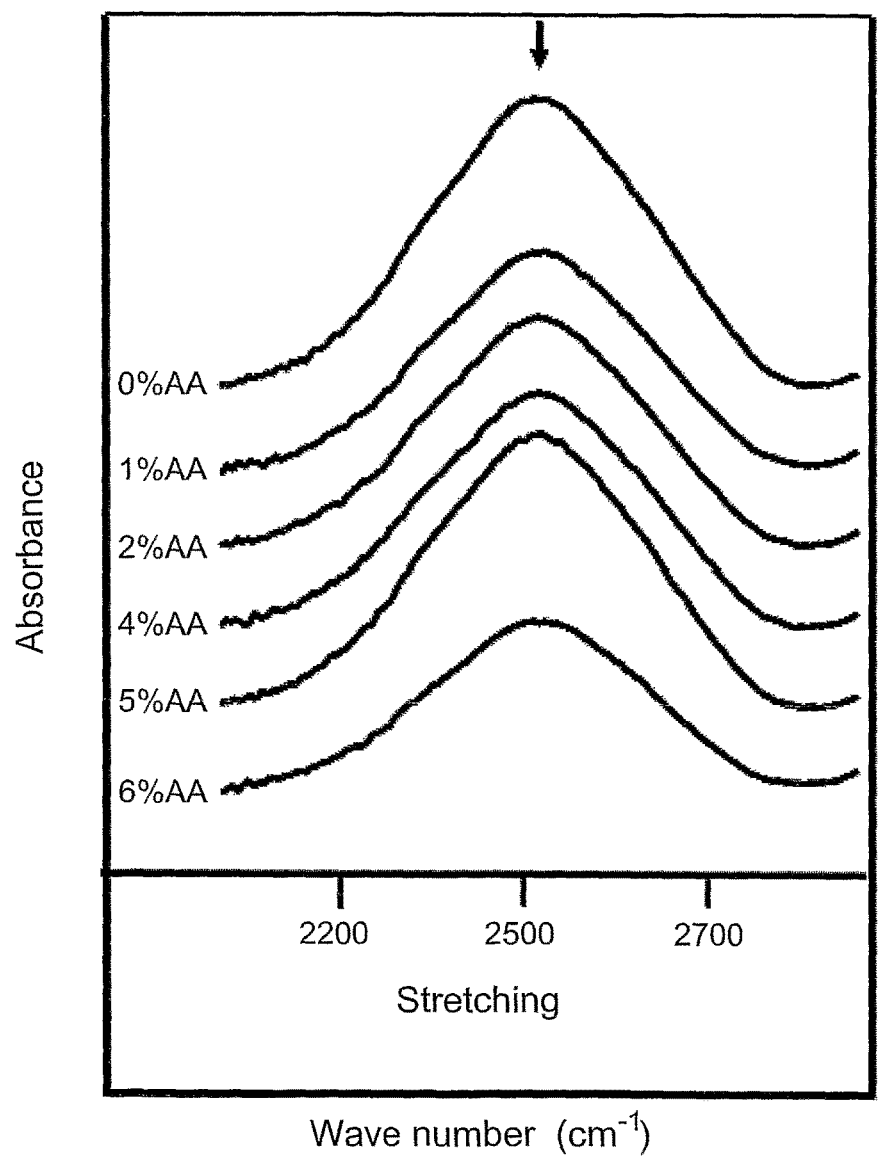
FIGS. 21a-c present: (a) ATR-FTIR frequency ($cm^{-1}$) as a function of AA concentration (wt %) of the C=O bonded carbonyl absorption modes. (b) The normalized peak area ($A_{free}/(A_{free}+A_{bonded})$) and $A_{bonded}/(A_{free}+A_{bonded})$ of the free and hydrogen-bonded carbonyl groups. (■) Hydrogen-bonded carbonyls, (▲) free carbonyls. (c) Width at half-height ($cm^{-1}$) as a function of AA concentration (wt %) of the C=O absorption modes of surfactant molecules. (■) Hydrogen-bonded carbonyls, (▲) free carbonyls.

Normally one can observe three vibrational modes of the GMO headgroups, however only the carbonyl at the α position (1720-1740 $cm^{-1}$) was examined (FIG. 21a). The carbonyl band consists of two components, one originating from freely rotating carbonyl groups (1740 $cm^-$) and the second from intramolecular hydrogen-bonded carbonyl groups (1730 $cm^{-1}$).

Information on the conformational order of the acyl chains and their interactions with the VE molecules was obtained by following the stretching modes of the $CH_2$ segments. The stretching modes of the GMO methylene groups were observed at ~2853 $cm^{-1}$ (symmetric stretching) and at ~2918 $cm^{-1}$ (antisymmetric stretching).

Water-Rich Core:

The gradual incorporation of AA reduced the frequency of OD stretching. It was shifted down from ~2501 $cm^{-1}$ without AA, through 2498 $cm^{-1}$ upon incorporation of 3 wt % AA, further down to 2496 $cm^{-1}$ with 6% AA, with an overall downward shift of 5 $cm^{-1}$, as depicted in FIG. 19. The reorganization of the water upon addition of AA could be detected also by the upward shift of the water bending vibration frequency. This frequency was augmented from 1651 $cm^{-1}$ in the absence of AA, through ~1656 with 3 wt % AA and more moderately to 1658 $cm^{-1}$ with 6 wt % AA, exhibiting an overall upward shift of 7 $cm^{-1}$ (FIG. 20, left). These results indicate distortion of the water structure upon embedment of the chaotropic AA molecule with decrease in the mean water-water H-bond angle. In line with the DSC results, additional stronger hydrogen bonds were detected in the water molecules with the two stages of the AA embedment. In the first stage at up to ~3 wt % AA, where the enlargement of the lattice parameter was more pronounced, meaning an increase in the water/surfactants interface area, relatively stronger hydrogen bonds were introduced in the $H_{II}$ structure. Thus, in addition to the water surrounding the polar GMO heads, AA molecules are also located adjacent to the GMO heads, thereby binding water and GMO polar groups (e.g., hydroxyls). Therefore, in the first stage stronger impact by introducing AA is detected, such as chaotropic behavior, distortion of the water structure and increase in the lattice parameter.

During the second stage of AA addition, since more moderate influences were observed, the interface (i.e., the GMO polar head groups) becomes saturated with water and AA molecules. Hence, the added AA molecules prefer to be located within the inner cylinder, relatively far from the interface and thus only moderately distort the free water structure and swell the cylinders.

As mentioned above, by substituting $H_2O$ by $D_2O$ the water and GMO head-groups can be better separated. Hence, following the O—H stretching vibrations at ~3390 $cm^{-1}$, reveals the GMO hydroxyls behavior (based on the observation that the hydrogen exchange at this point is negligible). Upon addition of AA, only moderate upward shift is observed in the GMO O—H stretching frequency of ~3 $cm^{-1}$ (FIG. 20 right). Since the GMO hydroxyl groups, constructing the liquid crystal structure, are known to be intra-hydrogen bonded to the carbonyl GMO it may be concluded that less intra-hydrogen bonding are present between the hydrophilic GMO headgroups. This conclusion is in agreement with the cylinder swelling phenomenon and stresses the observation that AA molecules surround the GMO head-groups up to saturation, consistently binding more to the water molecules than to the GMO.

Figure 21B:
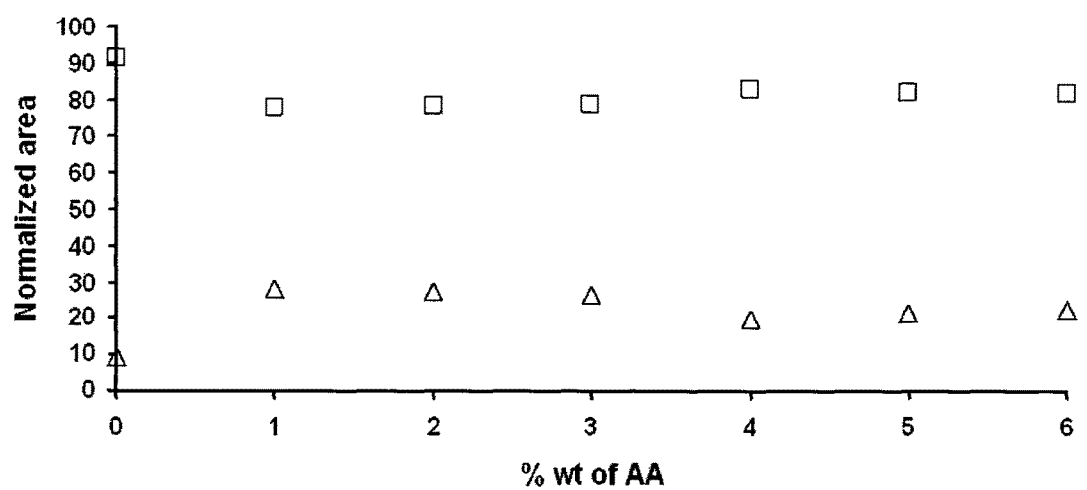
Figure 21C:
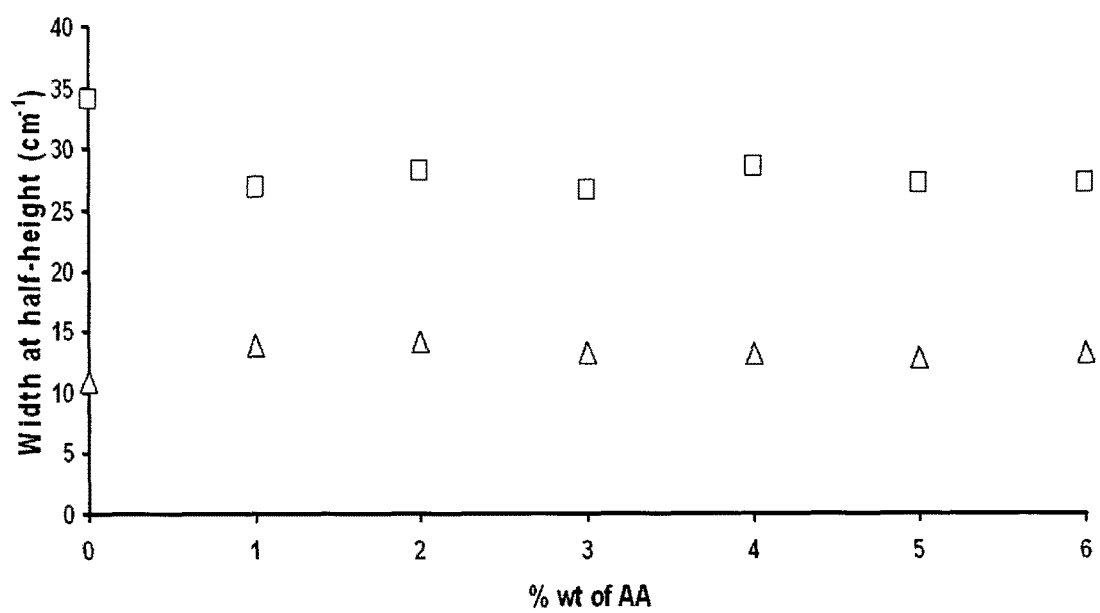

Water-Surfactant Interface:

In the interface region, only the carbonyl stretching mode was found to be sensitive to AA intercalation. The changes in the carbonyl bands area, position and width at the middle-height, upon addition of AA are depicted in FIG. 21a-c, respectively. Prior to the incorporation of AA, the free carbonyl band ($v_{C=O}$) was detected at 1742 $cm^{-1}$ with an additional higher intensity carbonyl band at ~1724 $cm^{-1}$. The peak areas for both the free and bound carbonyls were calculated and normalized to the overall area as a function of AA concentrations ($A_{free}/(A_{free}+A_{bonded})$ and $A_{bonded}/(A_{free}+A_{bonded})$, as summarized in FIG. 21b. The number of hydrogen-bonded carbonyls is reduced in favor of freely rotating groups once the AA is introduced (by ~10%), while further addition of AA does not alter the fraction of either free or bound carbonyl. Therefore, the solubilization of the AA molecules probably induced partial replacement of the intramolecularly hydrogen-bonded carbonyl groups bonds to carbonyl-AA bonds, as was suggested above. Furthermore, by following the positions of the free and bound carbonyl peaks, a decrease of only about 4 $cm^{-1}$ was observed in the bound carbonyl stretching frequencies as soon as AA was incorporated (FIG. 21a).

Taken together, it may be concluded that the partial hydrogen bonds that were disrupted by the AA solubilization were reoccupied by AA-carbonyl bonds, leading to distortion of the bound water structure and swelling of the $H_{II}$ cylinders. Although the embedded AA molecules spaced apart the GMO molecules, thereby breaking the intramolecular hydrogen-bonds between carbonyl and hydroxyl groups, they introduced stronger AA-carbonyl and AA-water hydrogen bonds. Moreover, the width at half-height of the lower frequency (bound) carbonyl mode was found to be decreased, while an opposite tendency was noticed in the width at half-height values of the high frequency (free carbonyl) band (FIG. 21c). These phenomena indicate the presence of a more restricted motion of the intramolecularly bound carbonyls (even though the cylinders are swelled) and an increased degree of rotation of the free carbonyls due to AA embedment.

Hydrocarbon Chain Region:

On the basis of the melting of the GMO fatty chains which is influenced by the presence of AA, as seen from the DSC thermographs, modifications in the methylene peaks by the incorporation of AA guest molecules were expected. However, no changes were noted in the methylene stretching vibrations.

As known, the IR spectral region of 1330-1400 $cm^{-1}$ provides information on the effect of the GMO $CH_2$ groups that are involved in nonplanar (gauche) conformers. As a rule, this range of frequencies consists of the end-gauche band (eg) at ~1341 $cm^{-1}$, the double-gauche band (gg) at ~1354 $cm^{-1}$, and the band of gauche-trans-gauche (kink) at ~1367 $cm^{-1}$. In this region, a band at ~1378 $cm^{-1}$ also appeared due to the symmetric bending of the end $CH_3$ group (umbrella mode). This band was insensitive to conformation as well as to chain length and hence its intensity was used as an internal standard to normalize the intensity of the other conformation-sensitive wagging modes.

By normalizing the intensities of the three $CH_2$ wagging bands to the $CH_3$ bending vibrations, only the gg and the kink bands (at ~1354 and ~1367 $cm^{-1}$, respectively) showed dependence on the solubilized AA (Table 5). The addition of AA molecules increased the fractions of both double-gauche and gauche-trans-gauche conformers in the GMO tails. Once AA was introduced and up to 4 wt %, the double-gauche conformations were increased by ~2-4%, simultaneously with gauche-trans-gauche conformers that increased by ~5%. Above this AA concentration, the area of the gg and kink bands increased only by 2 and ~4%, respectively. This is in line with the decrease trend of the GMO tails melting temperatures that observed by DSC (at 1-4 wt % AA, the hydrophobic melting peak was split into two peaks and appeared at 8.3 and 4.8° C., and above this concentration single peak was observed at ~5.4° C.).

TABLE 5

The intensities of the $CH_2$ wagging bands (gg and kink) normalized to the $CH_3$ bending vibrations of the $H_{II}$ systems empty and loaded with various amounts of AA.

| AA (wt %): | 0 | 1 | 2 | 3 | 4 | 5 | 6 |
|---|---|---|---|---|---|---|---|
| $I_{1354/1378}$ (gg) | 0.700 | 0.734 | 0.738 | 0.778 | 0.782 | 0.829 | 0.845 |
| $I_{1367/1378}$ (kink) | 0.750 | 0.767 | 0.777 | 0.805 | 0.792 | 0.826 | 0.823 |

Such an increase in the peak area may result from looser acyl chain packing with higher disorder, which in the case of the hydrophilic AA can be determined only by indirect inference. This is based on the limited locations of AA within the $H_{II}$ structure, i.e., inner cylinders and GMO/water interface, and supported by the observation that the incorporated AA molecules spaced apart the GMO molecules along the cylinders. Furthermore, bearing in mind the strong effect on the hydrophobic melting temperature, it may be assumed that upon formation of the more spaced GMO order, the VE is better capable of incorporating closer to the interface, similar to tricaprylin. Hence, the hydrophobic melting temperature decreased down to ~5° C., similarly as was observed when tricaprylin was used as the oil phase.

Figure 22:
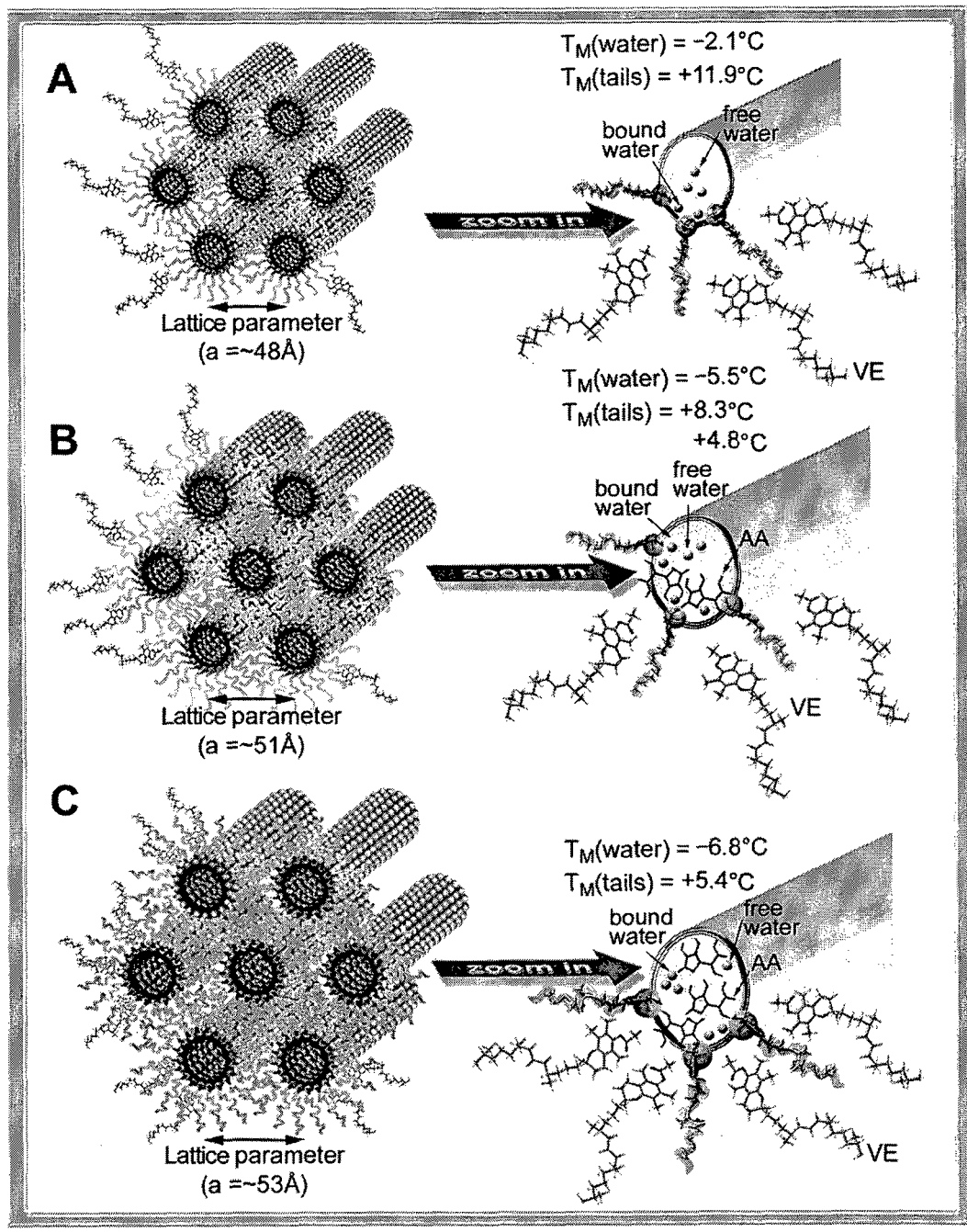
FIGS. 22a-c present drawings illustrating the solubilization location and interactions of AA and VE in the $H_{II}$ system. Three major modifications in the $H_{II}$ properties are indicated: cylinder swelling (%) based on the lattice parameter a-values, and $T_{M(water)}$ and $T_{M(tail)}$—the change in melting temperature of the water and GMO tail, respectively, upon the solubilization process, based on DSC thermographs. It should be noted that the molecular ratio between all the components should not be determined from the image.

The impact of the AA guest molecules and its location in the $H_{II}$ phase containing VE is summarized by illustration in FIG. 22. Two stages of the AA incorporation in the $H_{II}$ structure were found. When low contents of AA were added to the $H_{II}$ structure, the molecules surrounded the GMO polar head-groups introducing additional hydrogen bonding within the water molecules, and decreased the water melting temperature (FIG. 22a-b). Furthermore, partial GMO-water hydrogen bonds were disrupted and reoccupied by AA-carbonyl bonds, which was followed by distortion of the bound water structure, swelling of the $H_{II}$ cylinders and partial migration of VE towards the interface. The second stage of adding AA, 'saturation' of AA in the interface was assumed and thus additional guest molecules were located within the inner cylinder, relatively far from the interface (FIGS. 22b-c). This state was verified by moderate distortion of the free water structure, minor modifications in the hydroxyls and carbonyls bindings as well as moderate cylinders swelling. The overall broken intra-hydrogen bonds, such as the carbonyl-hydroxyl of the GMO and GMO-water, enabled additional migration of VE hence a decrease in the hydrophobic melting temperature was occurred. During the whole gradual solubilization of the AA molecules they were bound more/strongly to the water molecules than to the GMO.

In summary, it may be concluded that the incorporation of the AA molecules and its impact on the components constructing the $H_{II}$ structure were found to be opposed to the previous $H_{II}$ phase containing tricaprylin. Prior to the addition of AA, the two $H_{II}$ phases, that with VE and that with tricaprylin, exhibited similar characteristics including lattice parameter and water behavior i.e., melting point, however they differed in their hydrophobic region properties such as the GMO fatty chain melting. Due to the different degree of hydrophobic interactions between the GMO and the oil, VE as the oil phase demonstrated higher melting temperature as compared to using tricaprylin (by ~6° C.). The limited ability of the VE molecules to accommodate between the GMO tails, thereby be solvated by the tails, was attributed to the postponement of the $H_{II}$ formation to higher temperatures, compared to the tricaprylin systems.

Notwithstanding, as reservoir vehicles for solubilization, the VE-comprising systems demonstrated higher solubilization levels of ascorbic acid, and also other amphiphilic and hydrophobic guest molecules, compared to the system containing tricaprylin.

2. GMO/Lipophilic/Vitamin E/Phospholipids/Water Mesophase

Similarly to the above, the systems listed in Table 6 have been prepared:

TABLE 6

Vitamin E mesophases prepared according to the present invention. Values given are weight ratios of each component of the mesophase.

| System | GMO | VE | PC | Water |
|---|---|---|---|---|
| I | 78.5 | 8.7 | 2.0 | 10.8 |
| II | 70 | 17.0 | 2.0 | 10.8 |
| III | 63.7 | 23.5 | 2.0 | 10.8 |
| IV | 61.0 | 26.2 | 2.0 | 10.8 |
| V | 58.5 | 28.7 | 2.0 | 10.8 |

D. Incorporation of Biomolecules in the $H_{II}$ Mesophase of GMO/Triglyceride/Water General Comments:

In the monoolein-based system, the cubic phase was transformed into a $H_{II}$ mesophase upon heating, at ca. 85° C. As stated above, the hexagonal mesophase was characterized by higher packing cost than the cubic phase, but the opposite is true for curvature elastic energy. Therefore, elevated temperatures induced the tendency for interfacial curvature, which increased the curvature elastic costs of the bicontinuous cubic phase and stabilizing hexagonal symmetry.

Additionally, the mesophases of the invention were found stable at room temperature and thus have been determined, as will be further demonstrated, as candidate vehicles for efficient drug delivery, i.e., drug delivery systems. The incorporation of TAGs with various chain lengths to the binary GMO/water system demonstrated that immobilization of a TAG between GMO tails leads to a change in the geometry of monoolein molecules from cylindrical to wedge-shaped and thereby causes an increase in the CPP value of the system. This, therefore, encourages a transition from lamellar or cubic phases to hexagonal structures. In addition, the immobilization of TAG into the system was expected to reduce the packing frustration, stabilizing the hexagonal LLC at room temperature. The experimental results disclosed above indicate that a critical and optimal chain length of the triglyceride is required to induce the formation of $H_{II}$ at room temperature, although a great variety of chain lengths may be considered to produce usable systems. Among all TAGs examined, tricaprylin ($C_8$) attained the largest region of hexagonal structure in the phase diagram, as demonstrated in FIG. 23, indicating its flexible accommodation between the tails of the GMO. The tricaprylin high mobility in the surfactant aggregate is believed to provide direct transformation of the lamellar mesophase to the hexagonal phase, avoiding the formation of a cubic structure.

In addition, it was shown that phosphatidylcholine (PC) was solubilized into the ternary GMO/tricaprylin/water hexagonal system. The incorporation of PC into the mesophases had a pronounced effect on the GMO-water interface region on the molecular level and improved the elastic properties and thermal stability of the $H_{II}$ structures. It was also demonstrated using the ESEM (environmental scanning electron microscope) technique that the surface topology of these systems possessed fractal characteristics, suggesting a discontinuous and disordered alignment of the corresponding internal water rods on the mesoscale. It was additionally revealed that the topography (a mesoscopic property) of the $H_{II}$ phase was likely to be influenced by the microstructural parameters and the composition of the samples. This indication may potentially enhance transdermal drug delivery through the high surface area of these carriers owing to the tunable fractal nature of their surface.

Fluid Hexagonal Mesophases

Addition of polyethylene glycols and alcohols to the formulation was demonstrated to increase the range of applications of the $H_{II}$ mesophases and at the same time to form thermodynamically stable, low viscosity reverse bulk hexagonal mesophases at room temperature. For example, the addition of diethylene-glycol-mono-ethyl-ether (Transcutol) and ethanol to the ternary mixture of GMO, TAG and water on the expense of TAG content was tested as penetration enhancers and was found to improve the topical and transdermal delivery of various molecules. The incorporation of either Transcutol or ethanol induced the formation of the less-ordered, discontinuous $H_{II}$ structures, with smaller domain sizes and lower lattice parameter values at room temperature. As a result of this process, the viscosity at zero shear rate in the absence of guest molecules was found to be ~$10^4$ Pa·s, while the incorporation of the guest molecules lowered the viscosity down to ~$10^3$ Pa·s (2.75 wt % of Transcutol or ethanol).

Biopharmaceuticals are an important class of therapeutic agents. These pharmaceuticals include therapeutic proteins and peptides, synthetic vaccines, monoclonal antibody-based products, and nucleic acid-based medicinal products. Globally, about 500 candidate biopharmaceuticals are at various stages of clinical trial evaluations. According to the Pharmaceutical Research and Manufacturers of America, 324 potential protein-based medicines are being investigated to treat cancer, autoimmune disorders, infectious diseases, inflammation, and cardiovascular disease.

Although numerous protein-based therapeutics have been approved or are in advanced clinical testing, the development of more sophisticated delivery systems for this rapidly expanding class of therapeutic agents has not kept pace. Despite the revolutionary progress in large-scale manufacturing of proteins and peptides, effective and convenient delivery of these agents remains a challenge. This is mainly due to their intrinsic physicochemical and biological properties, leading to poor permeation through biological membranes (e.g., intestinal mucosa). Some of the major obstacles hindering effective administration of these drugs are their large molecular size, short half-life (degradation by proteolytic enzymes and neutralization by antibodies), physical and chemical instability, enzymatic catalysis, aggregation, adsorption, bio-incompatibility, and immunogenicity.

Oral administration of therapeutic macromolecules is notoriously difficult as a result of their high molecular weight, hydrophilicity, and susceptibility to enzymatic inactivation in the gastrointestinal tract. Parenteral routes of administration enable total systemic availability and fastest onset of action. The most commonly used parenteral routes are intravenous (I.V.), intramuscular (I.M.), and subcutaneous (S.C.). Intravenous injection offers rapid onset, which is desired for certain drugs such as streptokinase, where the beneficial effect is a function of time. However, administration with needles causes pain and can lead to the transmission of blood-borne pathogens induced by accidental needle pricks or intentional needle reuse. The consequence is reduced patient compliance.

In this respect, sustained release of drug products is a preferred therapeutic solution leading to increased patient compliance and reduced side effects, compared to simple solution or intravenous administration. There are various platform technologies providing slow release from the subcutaneous, intramuscular and intraperitoneal tissue. These platforms include implantable devices, oily suspensions, polymer-based gels and polymer-based microparticles. The polymer-based systems utilize biodegradable poly(lactic acid) or poly (lactide-co-glycolide) copolymers. Suspensions and oily solutions, some of which have been disclosed hereinabove, are widely used for sustained release. However, they are not appropriate for water soluble drugs and are often painful on administration, leading to poor patient compliance. In addition, such products frequently also suffer from poor stability and variable absorption kinetics. Whilst polymer-based solution or gel-type systems provide sustained release over the order of months, they require the drug to be dispersed or dissolved in the same solvent used to dissolve the polymer for administration (e.g. N-methylpyrrolidone). It is evident that there are limitations with each of the available technologies, and that a new platform technology that could overcome some of these limitations is highly desirable.

To improve therapeutic efficacy, research has focused on finding alternative means of administration, particularly noninvasive routes such as pulmonary, intranasal, or transdermal. The transdermal route has attracted particular interest as a promising means to advance the delivery of proteins and peptides, and to minimize side effects as well as first-pass metabolism. It has been used successfully for several decades and numerous systems for hormone replacement therapy, smoking cessation, and pain management are well accepted. However, there have been challenges in expanding use of the technology to the delivery of peptides, proteins, and other macromolecules. These biopharmaceuticals cannot permeate the skin's outer stratum corneum layer (the upper skin barrier) at levels or rates that achieve significant therapeutic effect. In order to impede the influx of toxins into the body and minimize water loss, the stratum corneum layer has very low permeability for foreign molecules. Currently, various technologies are used to increase the permeability of macromolecules by exploring iontophoresis, electroporation, ultrasound, and microporation using electrical current/voltage, radio frequency and microneedles to open the skin. Although mechanical abrasion and chemical enhancers may increase drug permeation, their effects on the skin's inherent rate-controlling properties are difficult to control and they may irritate the skin.

Therefore, in recent years tremendous efforts have been made to improve controlled delivery of proteins and peptides. Liquid crystalline phases, such as lamellar, reverse hexagonal, and cubic phases, present interesting properties for a topical delivery system, and hence were considered and have been studied as delivery vehicles of pharmaceuticals via the skin and mucosa [7-9]. These phases are (I) thermodynamically stable; (II) consist of nano-scaled hydrophilic and hydrophobic domains, which are separated by the surfactant self-assembled layers; (III) contain an extremely large surface and present the ability to incorporate compounds independent of their solubility, to protect them from physical and enzymatic degradation, and to sustain their delivery; and (IV) may consist of permeation enhancers as the structure-forming lipid/solvent [10].

The success of an innovative delivery system for proteins or peptides depends on its ability to fulfill some or all of the following parameters and perquisites:
  1. In vitro and in vivo stability
  2. Improved systemic availability
  3. Prolonged biological half-life ($T_{1/2}$)
  4. Patient convenience and compliance
  5. Reduced dosing frequency
  6. Local toxicity and safety concerns, and/or
  7. Product life cycle management.

Transdermal Drug Delivery

The major benefits of transdermal delivery are its relatively easier accessibility to the skin, assisting in high patient compliance, avoidance of the gastrointestinal tract and the ability to achieve sustained release. These advantages together with high rate of macromolecular drug discovery have led to a considerable advancement in transdermal administration development over the last decade. The transdermal route is considered as a promising approach to advance the delivery of peptides and to minimize side effects and first-pass metabolism. However, the skin has evolved to be a highly effective barrier around the human body. As a result, despite the significant promise of transdermal administration, it is still not trivial to deliver large molecular weight hydrophilic drugs (such as proteins and peptides) through the skin. Most of the relevant drugs do not cross the skin at therapeutic rates and it is not surprising therefore that less than 20 drugs have been approved by the FDA for transdermal delivery since the first (transdermal) patch was introduced more than 25 years ago.

There are two predominant pathways of drug permeation within the stratum corneum (SC), the transcellular and the intercellular routes. A molecule passing through the transcellular route must diffuse through the keratinocyte, but in order to move to the next keratinocyte, the molecule must partition into and diffuse through the estimated 4-lipid lamellae between each keratinocyte. This series of steps, including the partitioning into and diffusing across multiple hydrophilic and hydrophobic domains, is unfavorable for most drugs. Accordingly, the more common route for drugs to permeate the skin is the intercellular route. In this case, the molecules overcome the SC by passing between the corneocytes. Thus, the major effort to enhance permeation of drugs across the skin is currently concentrated on the manipulation of solubility in the lipid domain or the alteration of the ordered structure of this region.

Skin Penetration Enhancers

The limitations and the difficulty to cross the barrier of the SC by various molecules can be addressed and partially overcome via the skin application of penetration enhancers, compounds that increase the diffusion coefficient of the drug through the SC. There are two major mechanisms for penetration enhancement by these dedicated molecules. The first mechanism is the interaction of the enhancers with the polar headgroups of the lipids. Consequently, the lipid-lipid headgroup interactions and the packing order of the lipids are disturbed leading to the increased diffusion of hydrophilic drugs. The hydrophobic tails of the lipids can also be affected as a result of their headgroup disturbance by hydrophilic enhancers. Accordingly, structural rearrangements in the membrane occur, which can improve the penetration of lipophilic drugs.

The second possible enhancing mechanism is the interaction of the enhancers with the non-polar tails of the lipids. Lipophilic penetration enhancers can interact with the hydrocarbon tails of the membrane lipids, affecting their arrangement and leading to liquid-like behavior. In that case, the penetration of lipophilic drugs is improved due to the increased fluidization of the hydrocarbon chains. These structural modifications can also affect the order of the polar headgroups and also enhance the penetration of hydrophilic drugs. Variety of amphiphilic molecules was found to act as a penetration enhancers. For instance, phospholipids are known as membrane recognition agent and transport enhancer agent and it facilitates the bioavailability of the guest molecules transdermally.

Sustained Drug Delivery from LLC

Significant progress has been made during the last decade in the characterization of the interactions of peptides and proteins with LLC, mainly for crystallographic and drug delivery purposes. It has been affirmed that peptides and proteins could be accommodated in liquid crystal phases either in the aqueous channel compartments (water-soluble proteins and peptides) or in the lipid bilayer constituent (membrane proteins and peptides). LLC have been shown to provide sustained release of drug molecules with a range of physicochemical properties [11-13]. The cubic phase was shown to host a range of water-soluble biomacromolecules for use in controlled release applications.

The interaction of the peptide drugs Desmopressin, lysine Vasopressin, Somatostatin and Renin inhibitor with the cubic phase was studied by Ericsson et al [14] by means of phase behavior, self-diffusion and in vitro and in vivo release. These investigators found that such peptides can be solubilized in the cubic phase in the content range of 5-10 wt %. Desmopressin was shown to interact significantly with the monoolein water interface. The in vitro release experiments indicated time dependence of the drug release, as was expected from a matrix system. In addition, the peptides examined were shown to be protected against enzymatic cleavage, as demonstrated in simulated intestinal fluid experiments.

Solubilization of insulin in the cubic phase of GMO drastically affected its temperature-dependent structure and phase behavior as well as the aggregation kinetics and final aggregate structure of the protein. The results of Kraineva et al [15] revealed that insulin incorporation induced disappearance of the low temperature $L_c$ phase, increased the temperature stability of the lamellar $L_\alpha$ phase, and shifted the $L_\alpha \rightarrow Ia3d$ phase transition to slightly higher temperatures. Owing to the geometrical mismatch of the protein size and the water channel thickness of the lipid matrix, new cubic lipid structures were induced by the insulin incorporation already at very low concentrations of about 0.1 wt %. From the point of view of practical applications, monoolein-based cubic phase was able to protect the insulin protein from agitation-induced aggregation and its subsequent precipitation.

Clogston and Caffrey [12] systematically examined biomacromolecules ranged from a single amino acid (tryptophan), to complex proteins and nuclear DNA. The investigators found that for a given cubic phase, the rate of diffusion depends on the molecular size of the specific diffusing molecule. For a given cubic phase, after loading with a size-range series of drugs (including peptides and proteins), the release of each drug was measured by a Fickian diffusion model. In the case of small molecules, such as tryptophan and to some extent the 10-mer DNA linker, release from the cubic phase occurred over a period of 1-3 days. For intermediate sized molecules, such as cytochrome C, lysozyme and myoglobin, the bulk of the release occurred in a week. In contrast, for the large macromolecules ovalbumin, conalbumin, apo-ferritin and calf-thymus DNA, less than 12% release took place in a period of three weeks.

Shah and Paradkar [13] prepared in situ cubic phase transforming system of GMO. This system provided protection to the metalloenzyme seratiopeptidase (STP) in gastric environment and gave delayed and controlled release with no initial burst after oral administration.

Although the cubic phase has been proposed and studied as a drug delivery vehicle, there is very little information about the interactions of peptides and proteins with the $H_{II}$ mesophases. Some peptides were shown to affect structural transitions of LLC, favoring formation of $H_{II}$ mesophases [16,17]. According to Liu and Caffrey [17] lipophilic peptide gramicidin destabilized the cubic phase in favor of the inverted hexagonal phase, beyond a limiting concentration. Lopes et al [18] demonstrated increased skin penetration of cyclosporin A (CSA) from both the cubic and reverse hexagonal LC phases of GMO/water and GMO/water/oleic acid, respectively. Nevertheless, only the pharmacokinetic aspects of CSA delivery were addressed in these experiments.

Differences in LC nanostructure have previously been shown to change drug diffusion and hence release. The release was found to be diffusion controlled, with the generally larger aqueous channels of the cubic phase providing a faster release rate than the $H_{II}$ mesophase. Specifically, it is known that the release of hydrophilic drugs from the phytantriol-based $Q_2$ structure is significantly faster than from the $H_{II}$ mesophase (prepared by the addition of 10% vitamin E acetate to phytantriol) at 37° C.

Drug Delivery from the $H_{II}$ Mesophases of the Invention

Protein and peptide drugs are known to be inactivated by physical instability processes such as aggregation, precipitation, denaturation, and surface adsorption. The aggregation process resulting in protein/peptide precipitation has been a fundamental obstacle to the development of long-term delivery devices. Various classic approaches have been used to protect protein and peptide drugs from physical inactivation, one of which has been the use of stability-enhancing additives.

A series of $H_{II}$ mesophases with complex architectures for the solubilization and potential administration of bioactive peptides have been prepared. The results with solubilization of model protein lysozyme into $H_{II}$ mesophases determined that GMO-based liquid crystal was able to protect the incorporated protein from undergoing conformational changes due to its exposure to water-air interfaces. The α-helix conformation of lysozyme was stabilized at high pH conditions, demonstrating greater helical structure content, compared to a $D_2O$ solution. Moreover, the hexagonal phase decreased the unfavorable α→β transition in lysozyme, thereby increasing the stability of the protein under chemical denaturation. Immobilization of lysozyme into the proposed carriers hampered destruction of its helical structure between 65 and 73° C., compared to the water solution, probably due to hydrogen bonding of the protein with monoolein polar heads.

In addition, the practical feasibility of the solubilization of peptide drugs into the $H_{II}$ mesophase was illustrated via the lipophilic drug cyclosporin A and hydrophilic desmopressin, and their entrapment effects on the phase and conformational changes within the phase were studied on a macroscopic scale [19] and a molecular level [20-22].

The applicability and efficiency the $H_{II}$ mesophase as carriers for a transdermal delivery of desmopressin as model peptide drug was studied. Such delivery was especially relevant since the high hydrophilicity of this peptide was the main reason for its uncontrolled fast release when used without a proper carrier. A series of experiments were therefore designed and conducted in order to achieve a sustained release of this drug and to allow an efficient treatment with relatively long durations.

Figure 24:
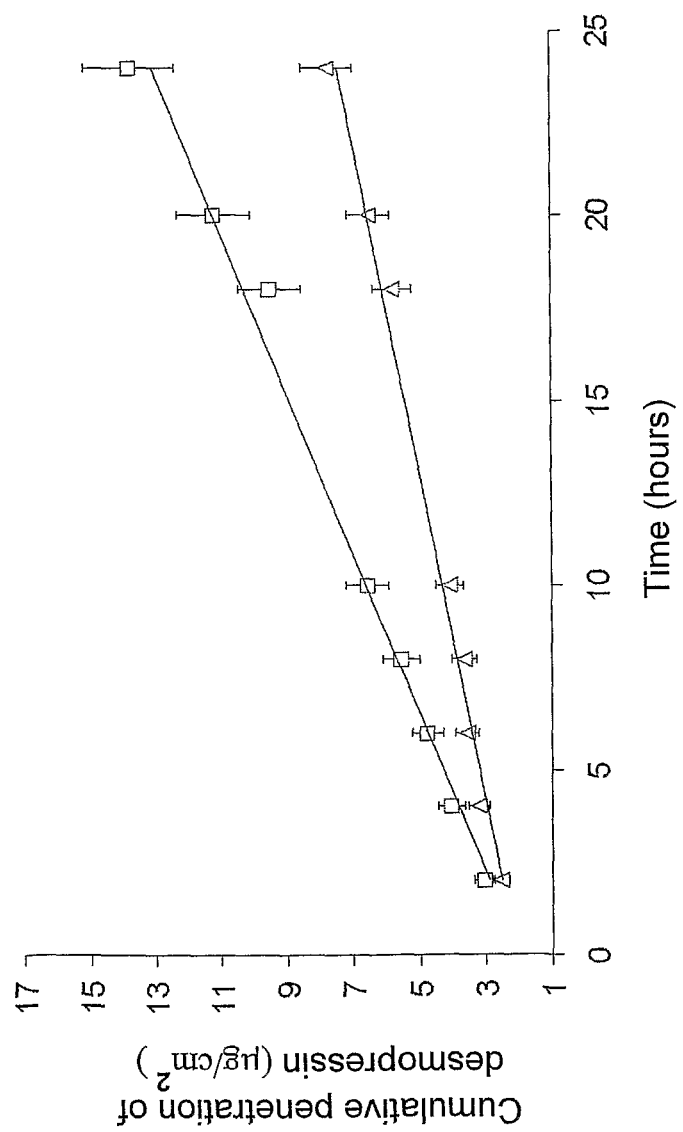
FIG. 24 presents the cumulative transdermal transport of 1 wt % desmopressin, (□) via water solution, (Δ) via $H_{II}$ mesophase.

In the case of bulk hexagonal mesophase, reduced values of steady-state flux were obtained for the drug and its permeability coefficients through the skin, as compared to a water solution. In other words, the peptide molecules penetrated more easily and freely through the skin from water solution, than from hexagonal phase vehicles. Hence, a sustained release of desmopressin was obtained via the $H_{II}$ mesophase (FIG. 24) [21]. A different penetration pathway was suggested when using LLC as drug vehicles, when compared to direct delivery through water solution. The drug probably accumulated in microfissures and in a three-dimensional network of thin threads of the skin. Subsequently, the hydrophilic drug was supposed to diffuse into the surrounding intercellular lipid from the microfissures matrix, acting like a source for sustained release. Hence, it was proposed that the intercluster penetration pathway is preferable for delivery of hydrophilic compounds via LLC, in contrast to the intercellular pathway when using the water solution.

Several determining factors could explain the obtained sustained release of the peptide. As shown, the release is caused by diffusion of the peptide in LLC. According to the SD-NMR analysis, it can be assigned to the physical restriction of the peptide diffusion within the tubes and the interactions of the desmopressin with the monoglyceride hydroxyls, denoting that the lowest self-diffusion coefficient of desmopressin was detected ca. 35° C. Another important factor was that the $H_{II}$ mesophases possess dominating elastic properties, as well as proper microstructural (lattice parameter) and mesostructural parameters (alignment of discontinuous and anisotropic polycrystalline domains, possessing fractal characteristics), to allow the penetration of the desmopressin molecules into the microfissures.

Figure 25:
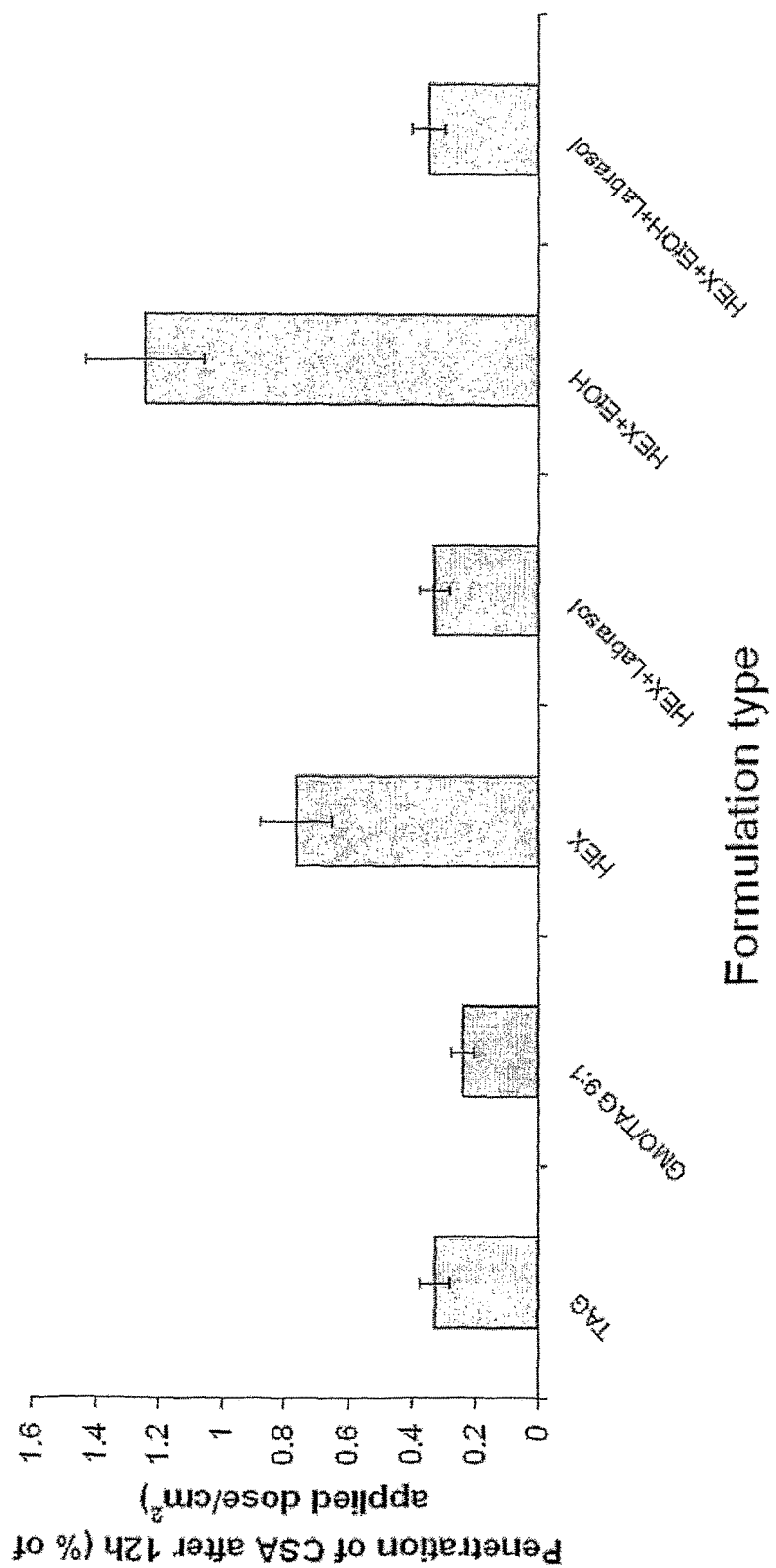
FIG. 25 presents in-vitro transdermal penetration of CSA (% of the applied dose/$cm^2$) after 12 h, as function of the applied formulation, demonstrating the higher rates of the HEX and HEX/ethanol carriers (HEX=GMO/TAG/PC/water). The experiments were conducted using Franz diffusion cells. Concentration of CSA was 1 wt % in all formulations.

Initial evaluation of cyclosporin A (CSA) release (as model hydrophobic peptide) was also performed using bulk hexagonal mesophase. As a cyclic and highly lipophilic peptide, CSA shows an extremely poor skin penetration, unless a special chemical or physical treatment was performed. Keeping such behavior in mind, the main objective of the designed experiments was to increase the skin penetration of this peptide, especially when incorporated in the proposed carriers. The results are schematically presented in FIG. 25. To achieve this goal the GMO/TAG/PC/water system (denoted HEX) was used, designed to solubilize CSA (it is not stable without PC) and penetration enhancers EtOH and Labrasol. The control systems included CSA samples, which were solubilized in solutions of tricaprylin or GMO/tricaprylin. The direct examination of the CSA delivery via hexosomes could not be performed, unfortunately, since it was not possible to formulate ordered PC containing dispersions, which are imperative for the stability issues.

The experiments revealed that increased penetration values of CSA after 12 h were achieved when the basic HEX system was used with addition of EtOH (1.2% of applied dose) or HEX as is (0.8% of applied dose), as compared to the control systems (0.2-0.3%). Interestingly, it was found that Labrasol did not function as a penetration enhancer for CSA in this system, neither by itself nor with EtOH, resulting in low delivery (0.3% of applied dose).

The results were compared with the findings of Lopes and coworkers [18], which examined CSA transdermal penetration in vitro from hexagonal mesophase that composed of GMO, oleic acid and water. Using their compositions, a significantly lower—0.03% of applied dose was obtained. These results demonstrate that the CSA penetration from the mesophases of the invention was 27-40 times higher than those obtained from the corresponding systems of Lopes et al [18] Without wishing to be bound by theory, two major reasons could contribute to the dramatic enhancement of the observed CSA penetration. The first reason has to do with the different chemical composition, comprising TAG, PC and EtOH, which function as penetration enhancers. The second reason is the interfacial interactions of CSA, as enabled by specific conformational changes. These modifications seem to have induced more efficient intermolecular hydrogen bonds and as a result led to a better solubilization of the CSA within the interface region of the $H_{II}$ mesophases. Such conformational changes significantly increased the hydrophilic properties of CSA, making it more susceptible to transfer processes. Becoming more hydrophilic, this peptide could penetrate the skin more readily and more rapidly. In turn, the penetration rate can be adjusted and controlled by a careful tuning of the apparent hydrophilicity of the CSA molecule in different environments.

Figures 26A, 26B:
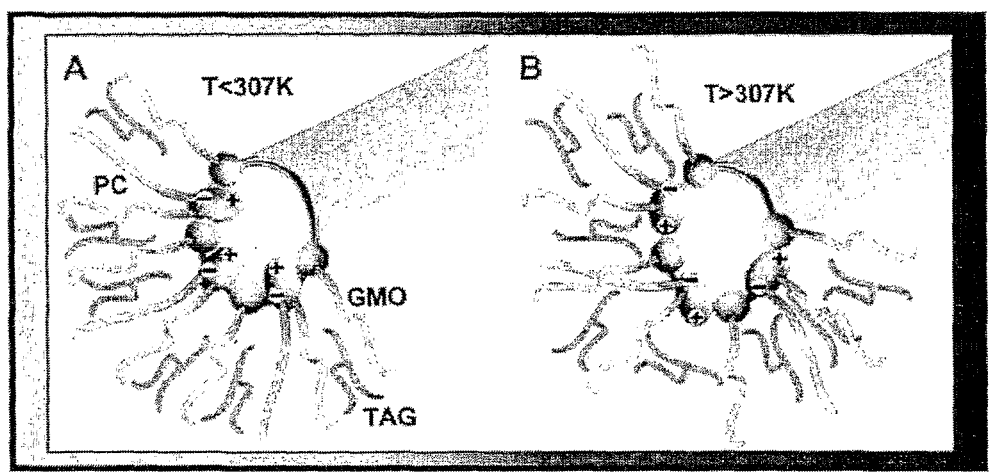
FIGS. 26A-B demonstrate the stabilization of the lipid layer.

In addition, the proposed carriers revealed a complex, temperature-activated molecular behavior in and around the interfaces of the mesoscopic structures of the gel. At critical temperature, T=35° C., the process of partial dehydration of the glycerol monooleate (GMO) head groups was noted by SD-NMR and dielectric spectroscopy measurements. Effectively, this represents a partial breakdown of the interfacial layer of water. A physical picture emerges whereby at $T_0=35°$ C., the "loosening" of the GMO heads accentuates the dangling motion of the phosphatidylcholine tails, evidenced by counter ion motion along the PC head. Furthermore, it precipitates the percolation of the large TAG molecules that are intercalated in the GMO and PC tails (FIGS. 26a-b).

Such physical modifications, occurring at physiological temperature are extremely important to drug delivery. Both the transport of hydrophilic and hydrophobic drugs can be enhanced by the temperature dependent increased molecular disorder.

Lipolysis of the $H_{II}$ Mesophase: Novel Controlled Release System for Biopharmaceuticals Although the $H_{II}$ mesophase may be advantageously used for sustained drug delivery, as noted hereinabove, these systems may also be used as controlled release systems. It is a well known that the release of a drug from liquid crystals is diffusion controlled, and therefore, liquid crystal nanostructure determines the drug diffusion and hence dictates the rate of release. Since accuracy in dosing of a drug is critical in order to obtain full control over the release of the drug, the diffusion rate of the drug within the carrier may be modulated and modulate its diffusion on demand.

Figures 27A, 27B:
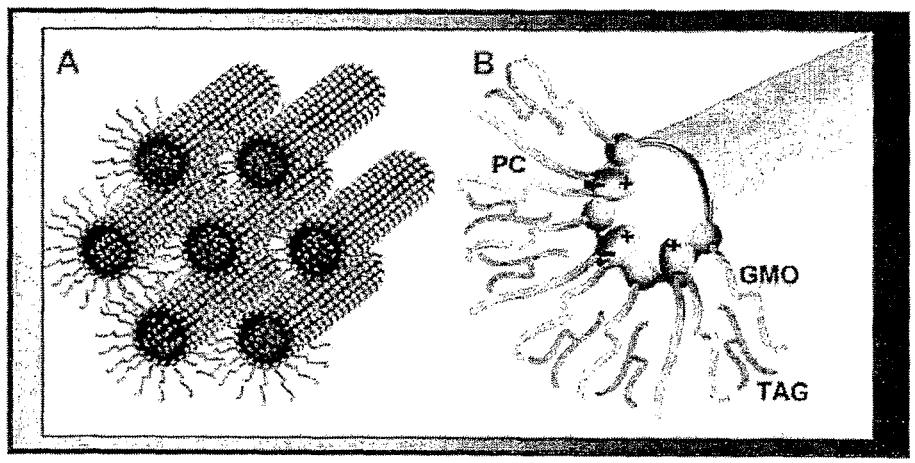
FIGS. 27A-B are schematic presentations of the mesophase.
Figure 28A:
FIGS. 28a-f are microscope images of samples comprising *Thermomyces Lanuginosus* Lipase (TLL) in the hexagonal mesophase. The process of lipolysis was monitored by microscopic imaging of the samples, indicating gradual decomposition of the hexagonal mesophase.
Figure 28B:
Figure 28C:
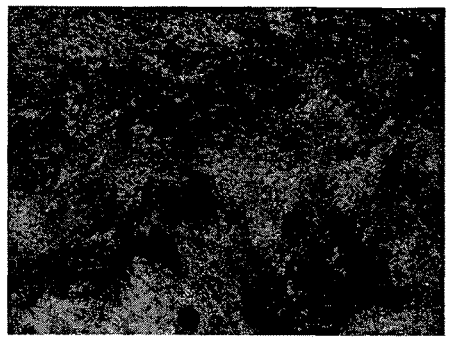
Figure 28D:
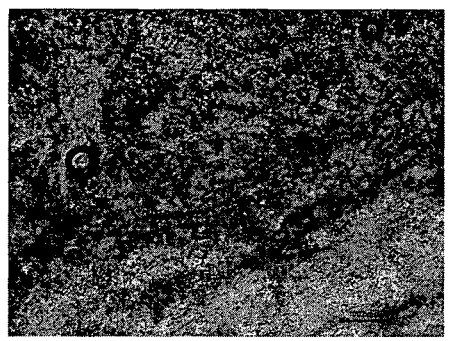
Figure 28E:
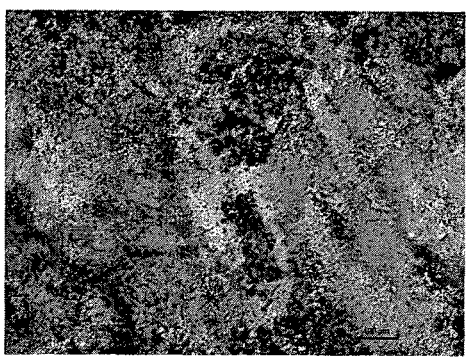
Figure 28F:
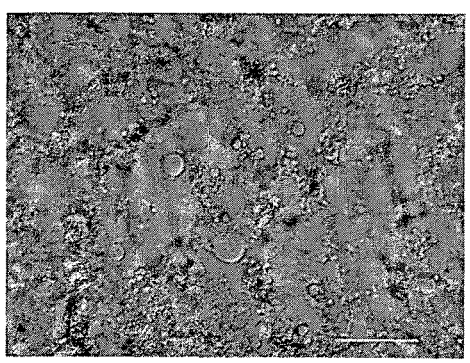

A gradual and controlled degradation of the carrier was undertaken in order to modulate the diffusion of the drug to a desired value, according to the therapeutic requirements. In one exemplary approach, the degradation of the mesophases by lipolysis with an enzyme (lipase), taking advantage of the fact that the systems of the invention are composed of monoglyceride, phospholipids (optionally) and TAG (FIGS. 27a-b).

TAGs constitute the largest source of dietary fatty acids. It is well known that TAGs cleavage at the brush border membrane is a prerequisite for efficient fatty acid absorption in the human body. TAGs are stored in fat body adipocytes as cytosolic lipid droplets. TG hydrolysis (lipolysis) is mediated by a lipase. It is located on the surface of the lipid droplet both in the basal and activated states. In the course of lipolysis, triacylglycerols are decomposed yielding diacylglycerols, monoacylglycerols, free fatty acids and glycerol as the main products. The lipase activity is variable towards triacylglycerols, diacylglycerols, and monoacylglycerols, allowing controlling the rate of reaction in each case. Regulation of the enzymatic activity results in variable chemical composition of the reaction products as a function of time.

This biological process (normally occurring in a living organism) was mimicked in $H_{II}$ mesophases of the invention, composed of monoacylglycerol, triacylglycerol and water. The lipase was solubilized in the system and controlled decomposition of the lipids by the enzyme was observed. Gradual and controlled decomposition of the lipids caused the destruction of the hexagonal mesophase as a function of time. Structural transformations occurring during the decomposition of the $H_{II}$ mesophase greatly influenced the diffusion and release of the incorporated drug from the system. If the decomposition of the hexagonal mesophase was fully controlled as a function of time, temperature, pH and enzyme concentration, the diffusion of insulin from the mesophase can be fitted to specific needs. This mode of action would allow setting the required diffusion time of specific drug by adjusting the rate of lipolysis of the mesophase lipids.

Figure 29B:
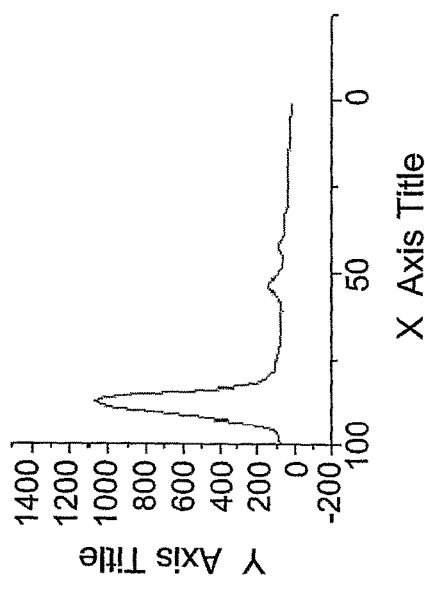
FIGS. 29a-d are SAXS measurements of decomposing mesophases.
Figure 29D:
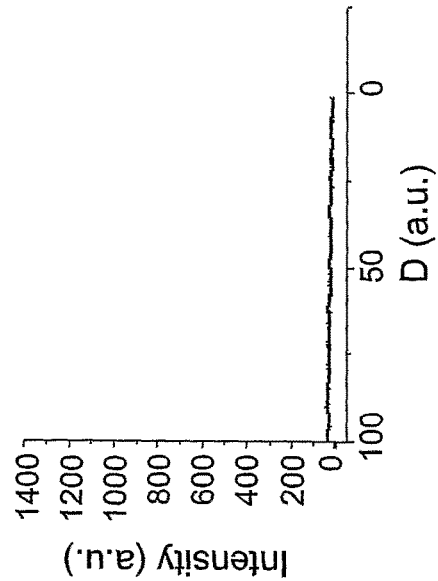
Figure 29A:
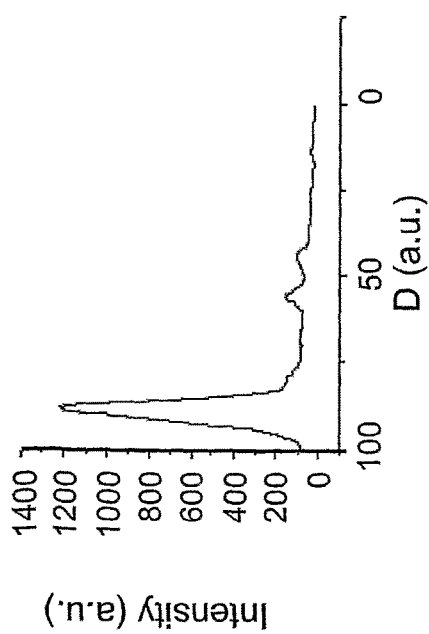
Figure 29C:
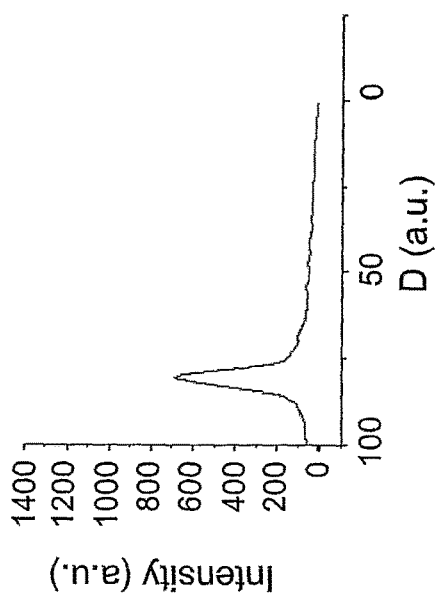

The effect of adding *Thermomyces* Lanuginosus Lipase (TLL) to the hexagonal mesophase has been studied and some promising initial results were obtained. It was possible to control the decomposition of the $H_{II}$ mesophase within extremely wide time scale, from two hours to three weeks, using very low enzyme concentrations in the range of nanomolars (nM). This process of lipolysis was monitored by microscopic imaging of the samples (FIGS. 28a-h), indicating gradual decomposition of the hexagonal mesophase. It is extremely important to emphasize that during the course of the reaction only 2 phases were obtained: the first was the $H_{II}$ mesophase, which underwent ongoing decomposition, and the second was the non-structured fluid phase, containing the products of the decomposition. No other structured liquid crystalline mesophase was obtained, allowing entire control of the diffusion (appearance of another structured mesophase would influence the desired diffusion rate). This was verified by SAXS measurements (FIG. 29) suggesting the following course of reaction: the structured mesophase (FIG. 29a) progressively lost its order and became more fluid (the peaks got broader, and the 2-d and 3-ed reflections gradually disappeared—FIGS. 29b-c) up to full decomposition of the LLC (FIG. 29d).

Figure 30:
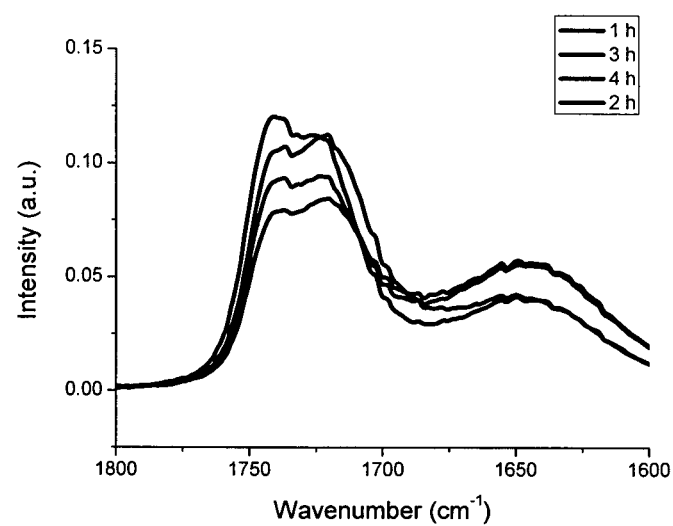
FIG. 30 presents ATR-FTIR measurements monitoring decomposition of mesophases.

In addition, this process was followed by ATR-FTIR measurements (FIG. 30). The carbonyl absorption mode of GMO was found to be sensitive for enzyme-surfactant interactions. The carbonyl band exhibits two clearly separated peak maxima, suggesting that this group is exposed to two different environments: the first one originates from 'free' carbonyls (1743 cm$^{-1}$) and the second is associated with the intramolecularly hydrogen-bonded carbonyl groups (1727 cm$^{-1}$). It was found that the peak frequencies for the bonded carbonyl groups demonstrated a monotonic decrease from 1728 to 1723 cm$^{-1}$ as a function of time. This finding shows that the strength of hydrogen bonding was increased as a result of the lipase action, reflecting the penetration of the lipase to the interface. Also as expected, the intensity of the carbonyls modes decreased, as a result of the decomposition of GMO.

Combined Utilization of Cationic Phospholipids in Lipolysis of the $H_{II}$ Mesophase The proposed technology of lipolysis can be improved, simultaneously using cationic phospholipids as penetration enhancers. Although the mesophases of the invention are mostly composed of GMO, incorporation of phospholipids was shown to be possible and even beneficial.

At present, a growing number of synthetic lipid transfection agents are becoming commercially available. Cationic phosphatidylcholines (PCs) are a particularly attractive cationic lipid type. These lipids are slowly metabolized and have remarkably low toxicities. At the same time, these lipids exhibit good transfection efficiencies. Cationic PCs have also been found to exhibit high transfection activity, both in vitro and in vivo, in antitumor and anti-cystic fibrosis pharmaceuticals. The cationic PCs are triester alkyl phosphate PC derivatives, in which the head group zwitterion is converted into a cation. Since their introduction about 10 years ago, a large number of cationic PCs with different hydrocarbon chains have been synthesized and tested for transfection. Maximum transfection was observed for lipids having 14:1 myristoleoyl or myristelaidoyl chains (total of 30 chain carbon atoms and 2 double bonds). There are significant effects that double bonds and chain length exert on the lipid transfection activity. Decreasing the number of double bonds and/or increasing the chain length result in strong, systematic decrease of the lipid transfection activity.

Transfection increases with increase of chain unsaturation from 0 to 2 double bonds per lipid and decreases with increase of chain length in the range ~30-50 total number of chain carbon atoms. Maximum transfection was observed for ethylphosphate PCs with 2 monounsaturated 14:1 chains.

Moreover, when the target drug is anionic, there is a possibility of ion pairing between the oppositely charged monovalent ions present in the vehicle. An ion-pair association of this type in effect increases the lipophilic properties of the drug, which in some cases is of benefit with regard to transdermal drug delivery.

However, in many cases it appeared that the apparent ion association between anionic drug and cationic enhancer drastically reduced the concentration of drug which can diffuse across the membrane. In order to circumvent this problem, during the lipolysis of the mesophases, negatively charged oleic acid (which is one of the reaction products) can compensate the surface charge and eliminate the electrostatically driven drug binding to the cationic enhancer. This would facilitate the drug departure from the complex. The fact that there is no association between the drug and the enhancer (phospholipid) not only leaves the drug free to diffuse across a membrane but the enhancer would also be available to disrupt the barrier properties of the skin. The concentration of free oleic acid is determined by the rate of lipolysis. Thus, the use of appropriate amounts of phospholipids and properly determining the rate of lipolysis will determine the extent of dissociation of the drug from the complex and also help to adjust the diffusion rate of the drug.

Enhanced Stability and Effective Oral Delivery of Calcitonin Via Reverse Hexagonal Liquid Crystals Osteoporosis and Related Bone Disorders Bone turnover is a highly dynamic process that involves two parallel (yet opposite) processes, the degradation of the bone matrix by osteoclasts and the formation of new matrix by osteoblasts. Under normal circumstances, these two processes are tightly and carefully balanced, in a manner that ensures that bone formation always adequately restores bone resorption. Perturbation of the fine balance between these two processes leads to pathologic situations, such as low bone mass and quality, as is the case in osteoporosis. The World Heath Organization (WHO) defines osteoporosis as a bone mineral density (BMD) of more than 2.5 standard deviations below the young adult mean (YAM), which practically means the peak bone mass during a normal lifespan. Osteoporosis is characterized by relatively excessive bone resorption that is not followed by adequate bone formation, even in cases where an increase in the absolute level of bone formation (total body bone mass) is observed.

Osteoporosis and related bone disorders are very widespread worldwide, especially, but not only, among the elderly population. It is estimated that for adults over 50 years old, such bone disorders are relevant, to some degree, for about 1 out of 2 in women, and for 1 out of 4 in men. The highest prevalence and incidence of osteoporosis is in women after the loss of sex hormone production. For such women the lifetime risk of fracture, including both hip fracture and non-hip fracture, is reported to be about 40%.

At present, most treatments for osteoporosis and related skeletal disorders are targeted at inactivating the osteoclasts activity, mainly by drugs that function as inhibitors and competitors of the various processes involved in bone degradation. Also common are treatments targeted at reducing the number of osteoclasts, mainly by actively inhibiting osteoclastogenesis or inducing apoptosis. Both treatments lead eventually to lower bone resorption levels. The main approved antiresorptive treatments include the bisphosphonates, estrogen replacement therapies and selective estrogen receptor modulators (SERMs), strontium renelate and calcitonin. These therapies result in the attenuation of bone resorption, although to different levels and with highly diverse modes of action. In addition to these, the anti-RANKL antibody denosumab, which is currently in clinical trials, strongly attenuates the generation of osteoclasts. Although quite effective for the reduction of bone resorption per se, most of these treatments involve also different types and degrees of side effects.

A major unwanted effect is the reduced bone formation that is secondary to the effects of these treatments on bone resorption. Most antiresorptive agents reduce bone formation as a secondary effect due to the coupling between bone resorption and formation, leading to reduced bone mass and density, and more importantly to reduced bone quality. The only antiresorptive drug that showed no major side effects so far is calcitonin, and recent lines of evidence indicate that in the case of calcitonin bone resorbtion may be attenuated without effects on bone formation.

Calcitonin and its Osteoporosis Therapeutic Potential

Calcitonin (CT) is a natural 32-amino acid peptide hormone, produced by the parafollicular cells in the thyroid gland of mammals. It was discovered more than 40 years ago and demonstrated to possess potent antiresorptive effects, shown to be mediated by direct binding of the peptide (in its active conformation) to its specific receptor on osteoclasts. The binding of low concentrations of CT to the CT receptor induces a rapid change in the cytoskeletal structure of osteoclasts in vitro, which in turn leads to a reduction in bone resorption without inducing apoptosis of the cells, events that are likely to convey the in vivo effects of CT at pharmacologic doses. Various types of CT exist, of which salmon CT (sCT) has been shown to be the most potent. As mentioned, recent results indicate that unlike most of the other antiresorptive agents, CT has a potential uncoupling effect, whereby CT transiently inhibits bone resorption, but only shows a marginal effect on bone formation in humans.

CT has been approved for use for treating postmenopausal osteoporosis, Paget's disease and hypercalcemia, all of which involve accelerated bone turnover. CT treatments (using mainly sCT) have, until now, been limited to either subcutaneous (injection) or intranasal (spray) administration. Due to a short half-life of the peptide, a single daily administration of it has been shown to be of marginal therapeutic effect, leading to its decreasing subscription and use in recent years. Multiple injections and multiple nasal administrations were found to be essential for optimal pharmacological effect, and thus patient compliance is low, especially for the elderly and limited population. The short half life of sCT is attributed to its rather low conformational stability, leading to its aggregation and practical inactivation in a time frame of a few minutes to a few hours.

The primary structure of sCT is characterized by a disulfide bridge between the cysteines 1 and 7 and a proline at the C terminus. It has also been demonstrated that the open polypeptide chain tends to form helices, which then participate in the inter-molecular contacts that lead to multimers and aggregation. This explains, at least in part, why both intraduodenal and intracolonic sCT administrations suffer from relatively low bioavailability (0.022% and 0.2-0.9%). Clearly, the very low bioavailability of sCT following oral administration is a result of its extensive proteolytic degradation in the digestion pathway.

Thus, sCT is in principle a very potent and effective drug for the treatment of osteoporosis and related bone disorders, but its use is currently limited by low stability and inconvenient means of delivery. Within the frame of the study leading to the invention disclosed herein the limitations of CT, as disclosed above, have been overcome by incorporation of sCT within a mesophase formulation. Results presented herein demonstrate that solubilizing sCT within hexagonal mesophases maintains the sCT conformational stability for more than 20 days, and that "gels" of the sCT/mesophase mixture may be used for efficient oral delivery.

Stability of Calcitonin within $H_{II}$ Mesophases and its Oral Delivery

The therapeutic use of calcitonin is hampered by its physical instability in aqueous solutions, especially at neutral at high pH. In solution, calcitonin has the tendency to associate and precipitate, forming turbid and viscous solution, consisting of fibrils. In this process the peptide, which primarily consists of random coil, gradually transforms to α-helix and mainly to β-sheet. This leads to low bioavailability of sCT following intraduodenal and intracolonic administrations, being 0.022% and 0.2-0.9%, respectively.

Figure 31:
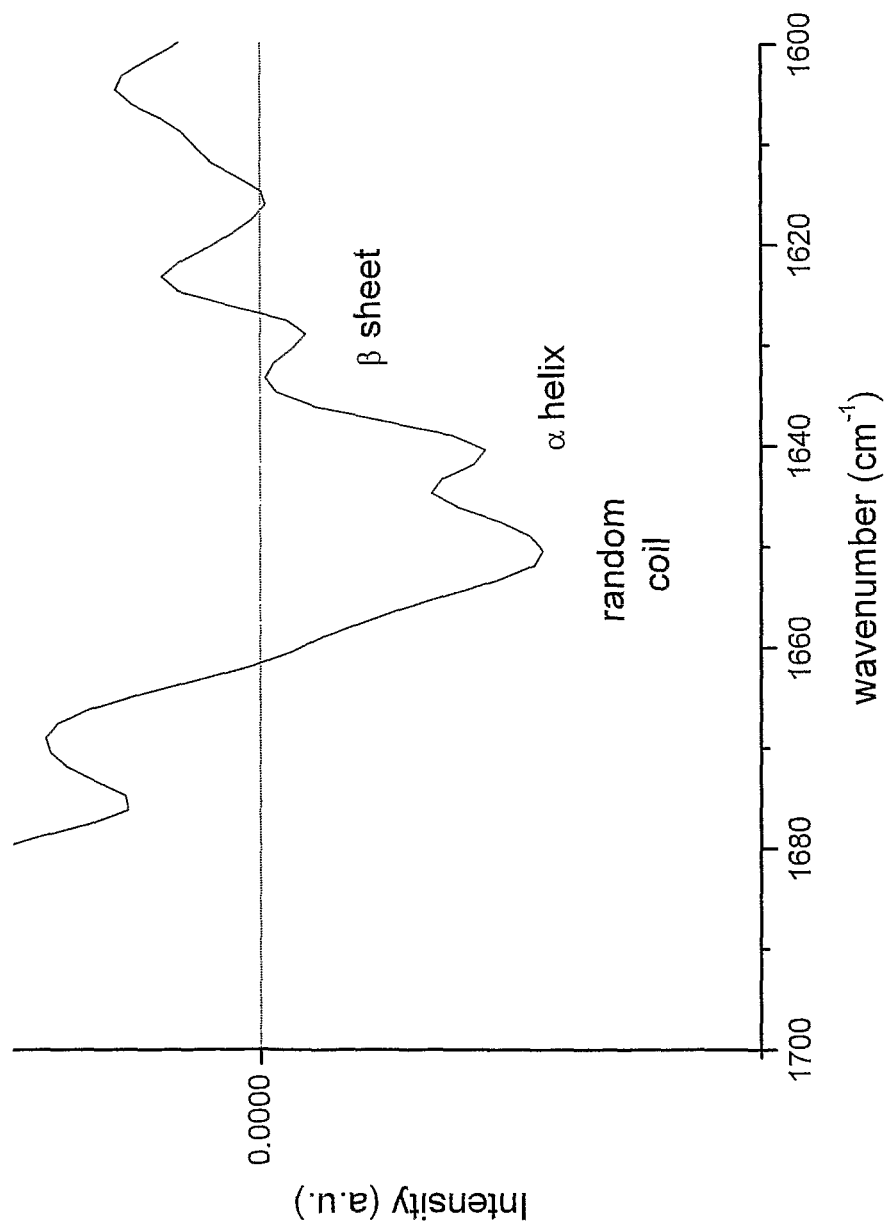
FIG. 31 depicts a typical second derivative ATR-FTIR spectrum of calcitonin when incorporated within the $H_{II}$ mesophase. The peaks observed reflect random coil (1650 cm$^{-1}$), α helix (1640 cm- and β-sheet (1628 cm$^{-1}$).
Figure 32A:
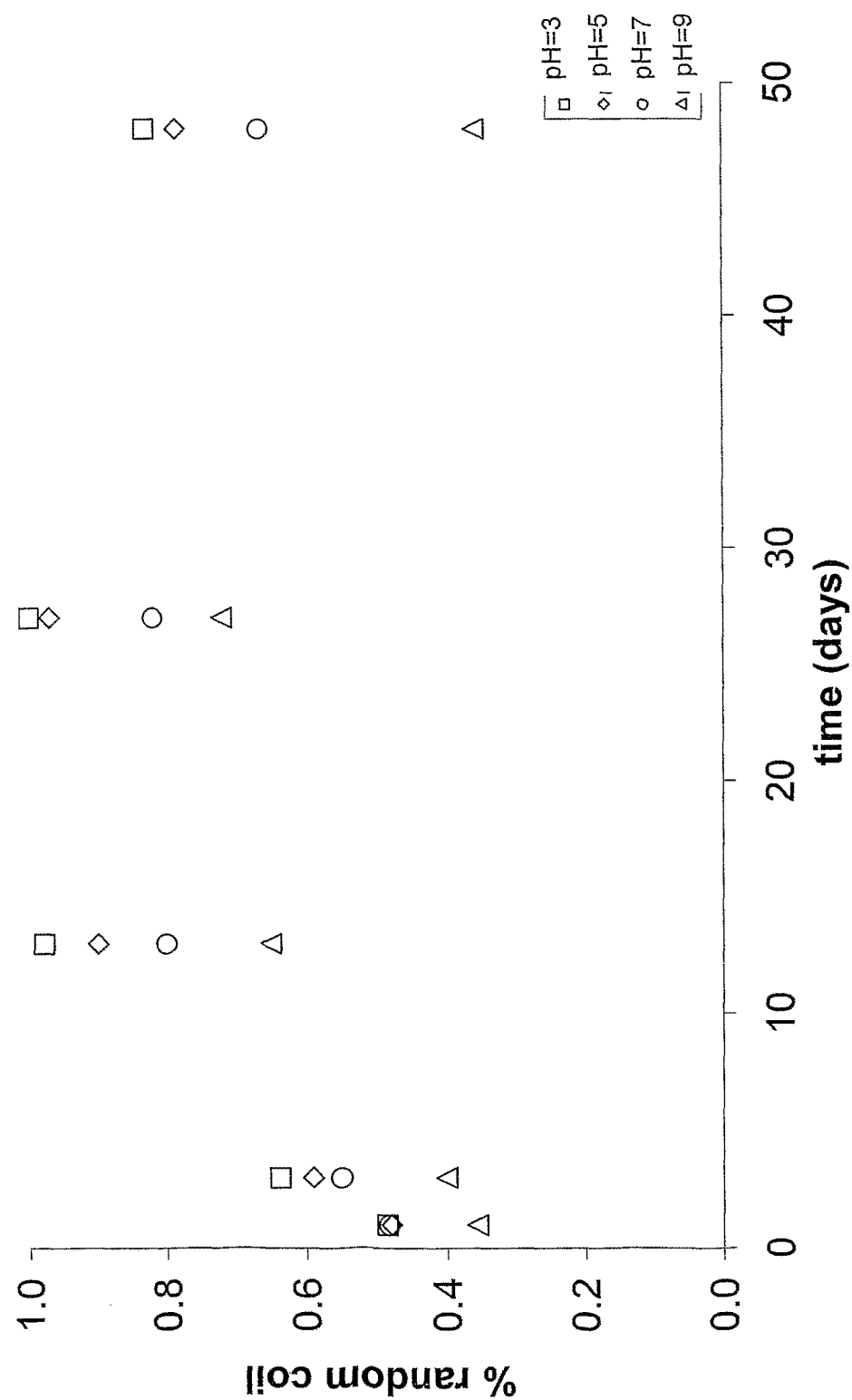
FIGS. 32a-c show.
Figure 32B:
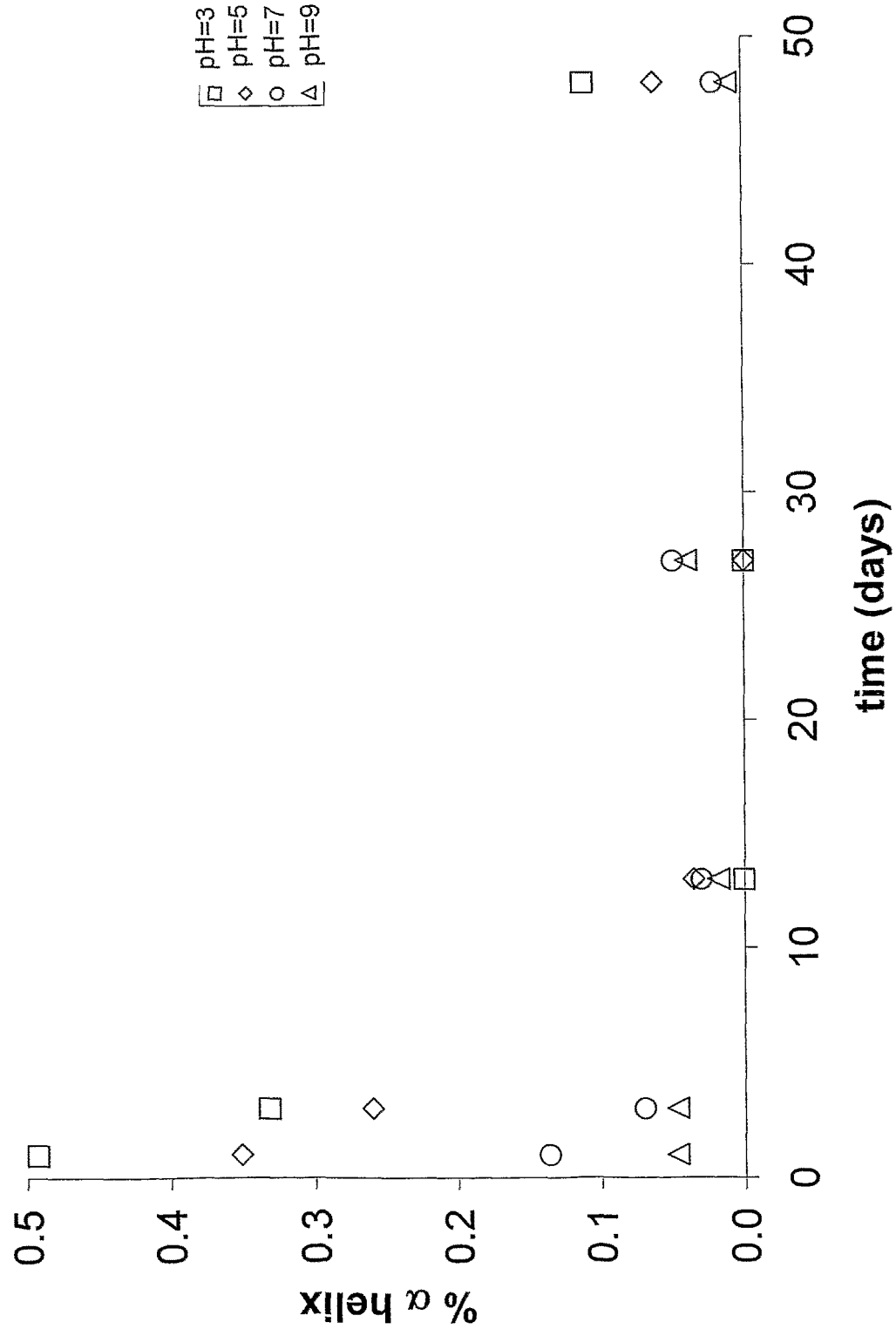
Figure 32C:
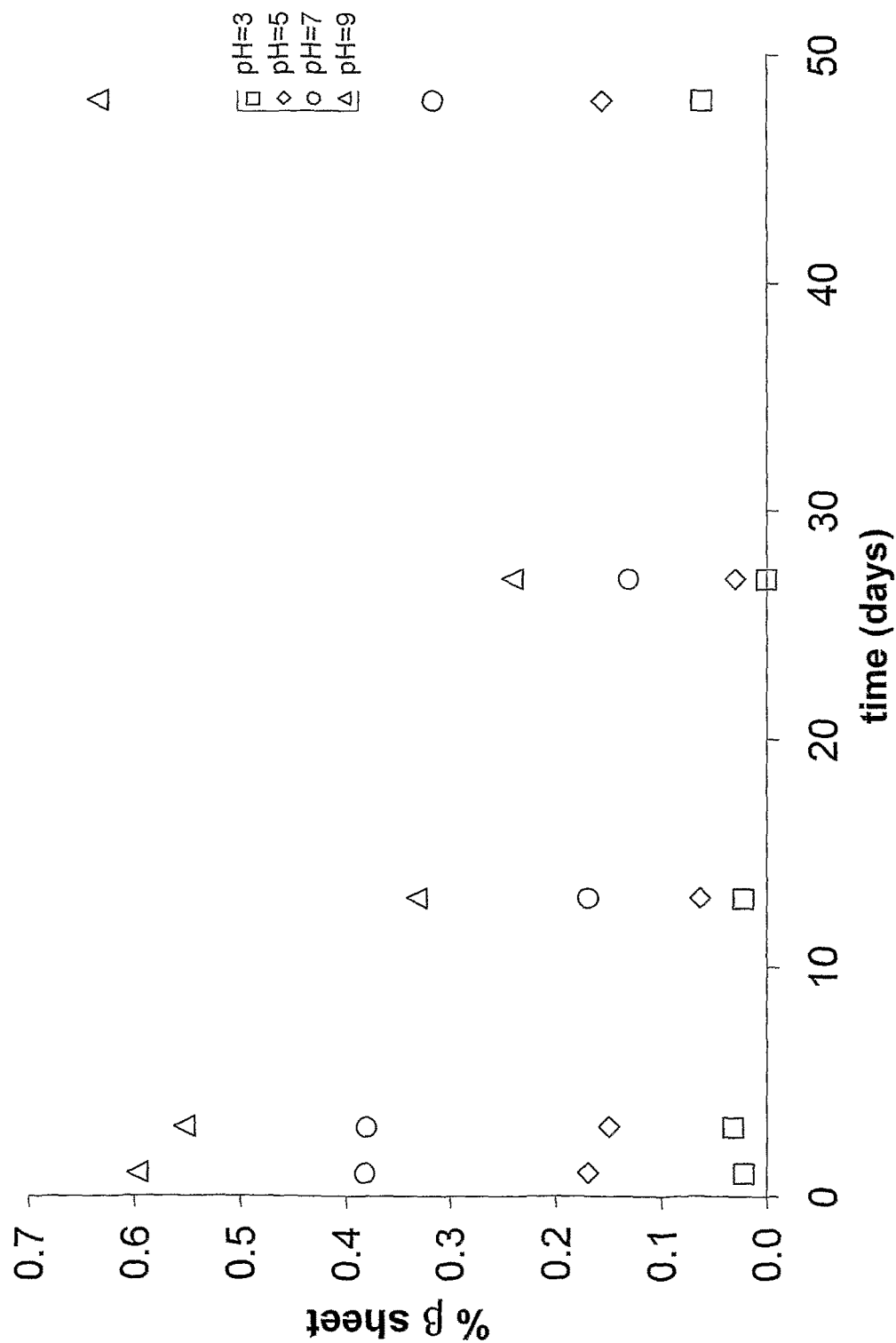

In order to overcome this problem, calcitonin was solubilized into the reverse hexagonal mesophase of the invention, as disclosed herein. Transition from random coil, which is characteristic to the stable and soluble state of the peptide to α helix and mainly β-sheet, which are responsible for the unfavorable aggregation, was detected using ATR-FTIR (FIG. 31). It is well documented that calcitonin is extremely unstable in aqueous solutions, which is reflected by a significant decrease of random coil content and simultaneous increase in the concentration of α helix and β-sheet. At room temperature this trend is observed already after ~2 days. Using the ATR-FTIR technique, the embedment of calcitonin into the aqueous channels of $H_{II}$ mesophase was explored, indicating a significant improvement in the stability of the peptide (FIGS. 32a-c). In over the examined pH range of 3 to 9, it was observed that initially low random coil structure at the first days after the solubilization was dramatically increased as a function of time and eventually reached ~100% at pH 3 and 5 at the 27th day. Simultaneously, the content of α helix and β-sheet forms drastically decreased, indicating stabilization of the peptide. This suggests stabilization of calcitonin in the reverse hexagonal phase, compared to a water solution where this macromolecule lost its stability after 2 days. Therefore, the opposite tendency of calcitonin stabilization in the hexagonal phase was detected, as compared to a water solution. Only after 27 days, the peptide stability decreased, as reflected by the decrease of the random coil content. This is a very promising result, indicating that calcitonin is stabilized as a function of time in the reverse hexagonal phase. Moreover, it was observed that at the acidic pH environment (pH 3-5) the random coil structure possesses the highest values, suggesting optimal stability of calcitonin. Hence, based on these promising results a delivery system for calcitonin were designed, offering controlled and sustained delivery of this important therapeutic agent.

Figure 33A:
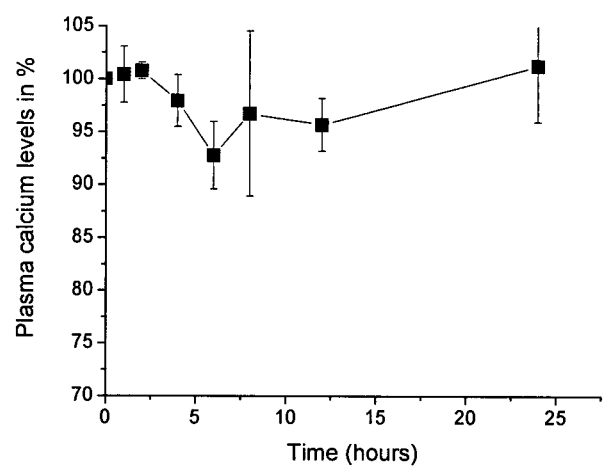
FIGS. 33a-b shows the plasma calcium levels of calcitonin via in vivo oral delivery in rats.
Figure 33B:
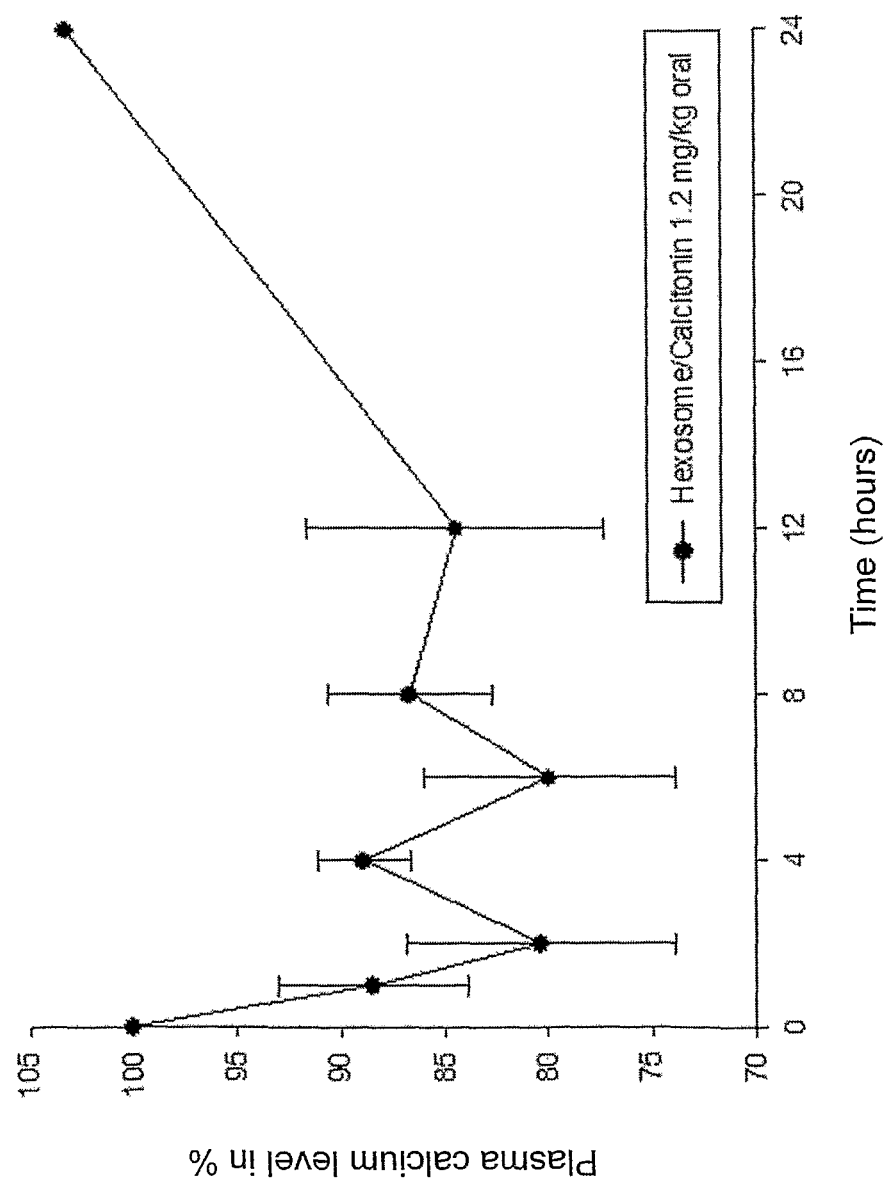

Using calcitonin solubilized in the hexagonal liquid crystals and/or their nano-dispersions (hexosomes), the plasma levels of calcium was significantly reduced, enabling efficient oral administration of calcitonin for the first time (FIG. 33).

Methods

Laboratory Animals

Male Sprague-Dawley rats (Orient Bio Inc, Korea), 7- to 8-weeks old, weighing 250-310 g, were used in the experiments. Animals were housed under a 12-h light-dark cycle, with food and water ad libitum. All animal handling was in accordance with the guidelines of Animal Care and Use Committee of the Korean Institute of Science and Technology.

Cannulation of the Jugular Vein and Arterial

The technique of cannulation of the jugular vein and arterial has been developed to allow serial blood sampling from an animal. After anesthesia with 0.4 ml/kg of intraperitoneally administered Rumpun/Zoletile [1:2 (v/v)], an incision was made in the skin just above the right clavicle. After preparation of the jugular vein, it was ligated at the distal side. A cannula filled with heparinized normal saline (10 units/ml) was inserted until the tip reached into the right atrium. Arterial cannulation was performed according to the same methods. The cannula was fixed to the vessel, tunneled to the head of the animal, fixed to the skin between the ears and further protected by a metal spring surrounded by polyvinyl chloride tubing. After cannulation, the animal was placed in a metabolic cage that allowed free movement of the animal. The experiment was started after a recovery period of a day from the operation. Blood samples of 200 μl were taken from cannulated animals at 0, 1, 2, 4, 6, 8, 12 and 24 h after administration, and this volume was replaced with drug-free heparinized rat blood obtained from donor rats. Blood samples were centrifuged (13000 g, 5 min, HANIL MICRO-12) and plasma samples were collected and stored at −70° C. until analysis.

Analytical Methods

Calcium concentration at time zero was normalized as the reference level. The rats were divided into three groups and treated separately with the different calcitonin route. The calcium level in plasma sample was determined using a commercial Calcium Colorimetric Assay Kit (K380-250, Biovision, Mountain View, Calif., USA). In short, plasma calcium was treated with o-cresolphthalein to form a purple colored complex which was measured at 575 nm. An aliquot of 10 μl of the plasma was used in each measurement.

In Vivo Study

Control—Untreated rats.

Intraveinous injection—5 μg of calcitonin was dissolved in 1 ml of a sterile 0.9% NaCl solution. SD rats received 5 μg/kg of intravenous calcitonin.

Hexosome mesophase/Calcitonin—SD rats were given Hexosome mesophase/Calcitonin (0.037 mg/kg or 0.2 mg/kg) p.o. by gavage.

The invention claimed is:

1. A delivery system for the delivery of a drug, said system comprising (i) a stable reverse hexagonal mesophase composition suitable for oral or transdermal administration of at least one drug or biomacromolecule, (ii) at least one drug or biomacromolecule contained within said mesophase composition, and (iii) a hydrolyzing agent adapted to cause degradation of said mesophase composition, thereby releasing the drug or biomacromolecule in a controlled manner over a period of time after administration, said hydrolyzing agent being an enzyme, said mesophase composition comprising, as components:

glycerol monooleate (GMO) in an amount ranging from about 58 wt % to about 85 wt %, and the remainder of the components comprising at least one phospholipid, at least one lipophilic compound, and water, the lipophilic compound being selected from the group consisting of vitamin E, tricaprylin, or a mixture of vitamin E and tricaprylin, wherein the relative amounts of said components are selected such that self-assembly of the components into the stable reverse hexagonal mesophase occurs in up to about a week, said mesophase composition being suitable for oral or transdermal administration of at least one drug or biomacromolecule.

2. The delivery system according to claim 1, wherein the mesophase composition is adapted to release the drug in a controlled manner over a period of time after administration.

3. The delivery system according to claim 1, wherein the mesophase composition is adapted for sustained release of the drug.

4. The delivery system according to claim 1, wherein, in said mesophase composition, said lipophilic compound is a mixture of vitamin E and tricaprylin.

5. The delivery system according to claim 1, wherein, in said mesophase composition, said at least one phospholipid is a glycerophospholipid.

6. The delivery system according to claim 5, wherein, in said mesophase composition, said glycerophospholipid is selected from the group consisting of mono-phosphatidyl glycerols, bis-phosphatidyl glycerols, and tris-phosphatidyl glycerols.

7. The delivery system according to claim 5, wherein, in said mesophase composition, said phospholipid is selected from the group consisting of phosphatidyl choline (PC), dipalmitoylphosphatidylcholine, phosphatidyl ethanolamine (cephalin), phosphatidyl inositol, phosphatidyl serine, cardiolipin, plasmalogen, lysophosphatidic acid, phosphatidylinositol (3,4)-bisphosphate, phosphatidylinositol (3,5)-bisphosphate, phosphatidylinositol (4,5)-bisphosphate, phosphatidylinositol 4-phosphate, phosphatidylinositol (3,4,5)-trisphosphate, and phosphatidylinositol 3-phosphate.

8. The delivery system according to claim 7, wherein, in said mesophase composition, said phospholipid is phosphatidyl choline (PC).

9. The delivery system according to claim 1, wherein the mesophase composition further comprises at least one alcohol.

10. The delivery system according to claim 9, wherein the mesophase composition is of the general form GMO/lipophilic compound other than vitamin E/vitamin E/phospholipid/alcohol/water.

11. The delivery system according to claim 9, wherein the mesophase composition is selected from the group consisting of:
GMO/tricaprylin/vitamin E/phospholipid/alcohol/water,
GMO/tricaprylin/vitamin E/PC/alcohol/water,
GMO/tricaprylin/vitamin E/PC/transcutol/water,
GMO/tricaprylin/vitamin E/PC/ethanol/water, and
GMO/tricaprolyn/vitamin E/PC/transcutol/water.

12. The delivery system according to claim 1, wherein, in said mesophase composition, said water is present in an amount of about 10 to about 25 wt % of the mesophase composition.

13. The delivery system according to claim 1, wherein, in said mesophase composition, the ratio between said glycerol monooleate to said at least one lipophilic compound is between 60:40 and 95:5 (wt %).

14. The delivery system of claim 1, being an oral delivery system of said at least one drug or biomacromolecule.

15. The delivery system of claim 1, being a transdermal delivery system of said at least one drug or biomolecule.

16. The delivery system according to claim 15, wherein the biomacromolecule or drug is insulin.

17. The delivery system according to claim 15, wherein said biomacromolecule or drug is selected from the group consisting of proteins, peptides, hormones, synthetic vaccines, monoclonal antibodies and nucleic acids.

* * * * *